(12) United States Patent
Cevc et al.

(10) Patent No.: US 7,927,622 B1
(45) Date of Patent: Apr. 19, 2011

(54) METHODS OF TRANSNASAL TRANSPORT/IMMUNIZATION WITH HIGHLY ADAPTABLE CARRIERS

(76) Inventors: Gregor Cevc, Gauting (DE); Amla Chopra, Walker, MI (US); Juliane Stieber, Munich (DE)

( * ) Notice: Subject to any disclaimer, the term of this patent is extended or adjusted under 35 U.S.C. 154(b) by 0 days.

(21) Appl. No.: 09/890,371

(22) PCT Filed: Jan. 26, 2000

(86) PCT No.: PCT/EP00/00598
§ 371 (c)(1),
(2), (4) Date: Apr. 8, 2002

(87) PCT Pub. No.: WO00/44350
PCT Pub. Date: Aug. 3, 2000

(30) Foreign Application Priority Data

Jan. 27, 1999 (EP) .................................... 99101480

(51) Int. Cl.
*A61K 9/127* (2006.01)
*A61K 38/54* (2006.01)
(52) U.S. Cl. ........................................ 424/450; 424/94.3
(58) Field of Classification Search .................... None
See application file for complete search history.

(56) References Cited

U.S. PATENT DOCUMENTS

| | | | |
|---|---|---|---|
| 4,036,953 A * | 7/1977 | Adam et al. ................ 435/170 |
| 4,095,596 A * | 6/1978 | Grayson ................. 128/203.21 |
| 4,185,100 A | 1/1980 | Rovee |
| 4,369,182 A | 1/1983 | Ghyczy et al. |
| 4,383,993 A * | 5/1983 | Hussain et al. ............... 514/177 |
| 4,619,794 A | 10/1986 | Hauser et al. |
| 4,666,747 A | 5/1987 | Quinn et al. |
| 4,731,210 A | 3/1988 | Weder et al. |
| 4,746,509 A | 5/1988 | Haggiage et al. |
| 4,783,450 A | 11/1988 | Fawzi et al. |
| 4,849,224 A | 7/1989 | Chang et al. |
| 4,897,269 A | 1/1990 | Mezei |
| 4,911,928 A | 3/1990 | Wallach |
| 4,921,706 A | 5/1990 | Roberts et al. |
| 4,937,078 A | 6/1990 | Mezei et al. |
| 4,937,254 A | 6/1990 | Sheffield et al. |
| RE33,273 E | 7/1990 | Speaker |
| 4,938,970 A | 7/1990 | Hustead |
| 4,944,948 A | 7/1990 | Uster et al. |
| 4,954,345 A | 9/1990 | Muller et al. |
| 4,983,395 A | 1/1991 | Chang et al. |
| 5,008,050 A | 4/1991 | Cullis |
| 5,043,165 A | 8/1991 | Radhakrishnan |
| 5,049,392 A | 9/1991 | Weiner |
| 5,104,661 A | 4/1992 | Lau |
| 5,145,684 A | 9/1992 | Liversidge et al. |
| 5,154,930 A | 10/1992 | Popescu et al. |
| 5,202,125 A | 4/1993 | Ebert et al. |
| 5,209,720 A | 5/1993 | Unger |
| 5,238,613 A | 8/1993 | Anderson |
| 5,244,678 A | 9/1993 | Legros et al. |
| 5,322,685 A | 6/1994 | Nakagawa et al. |
| 5,460,820 A | 10/1995 | Ebert et al. |
| 5,498,418 A | 3/1996 | Beutner et al. |
| 5,498,420 A | 3/1996 | Edgar |
| 5,510,118 A | 4/1996 | Bosch et al. |
| 5,552,160 A | 9/1996 | Liversidge et al. |
| 5,585,109 A | 12/1996 | Hayward et al. |
| 5,607,692 A | 3/1997 | Ribier et al. |
| 5,614,178 A | 3/1997 | Bloom et al. |
| 5,648,095 A | 7/1997 | Illum et al. |
| 5,653,987 A * | 8/1997 | Modi et al. ................... 424/400 |
| 5,654,337 A | 8/1997 | Roentsch et al. |
| 5,681,849 A | 10/1997 | Richter et al. |
| 5,716,526 A | 2/1998 | Keleman |
| 5,716,638 A | 2/1998 | Touitou et al. |
| 5,741,515 A | 4/1998 | Ciceri et al. |
| 5,763,422 A | 6/1998 | Lichtenberger et al. |
| 5,783,208 A | 7/1998 | Venkateshwaran et al. |
| 5,783,210 A | 7/1998 | Tremblay |
| 5,837,289 A | 11/1998 | Grasela et al. |
| 5,858,330 A | 1/1999 | Boltri et al. |
| 5,874,095 A | 2/1999 | Deckner et al. |
| 5,874,422 A | 2/1999 | Krause et al. |
| 5,891,472 A | 4/1999 | Russell |
| 5,958,379 A | 9/1999 | Regenold et al. |
| 5,985,860 A | 11/1999 | Toppo |
| 6,028,066 A | 2/2000 | Unger |
| 6,045,827 A | 4/2000 | Russell |
| 6,069,172 A | 5/2000 | Bertini et al. |
| 6,083,996 A | 7/2000 | Buyuktimkin et al. |
| 6,165,500 A | 12/2000 | Cevc et al. |
| 6,193,996 B1 | 2/2001 | Effing et al. |
| 6,200,598 B1 | 3/2001 | Needham |
| 6,214,386 B1 | 4/2001 | Santus et al. |
| 6,248,329 B1 | 6/2001 | Chandrashekar et al. |
| 6,248,353 B1 | 6/2001 | Singh |
| 6,261,559 B1 * | 7/2001 | Levitt et al. ................ 424/139.1 |

(Continued)

FOREIGN PATENT DOCUMENTS

AU      1740283      7/1983

(Continued)

OTHER PUBLICATIONS

Abstract searched from Derwent World Patents Index Latest, for EP 0102 324, Jul. 31, 2007.*

(Continued)

*Primary Examiner* — Robert Landsman
*Assistant Examiner* — Bruce D Hissong
(74) *Attorney, Agent, or Firm* — Neymeyer-Tynkov LLC; Valeria Neymeyer Tynkov

(57) ABSTRACT

The invention deals with the transport of preferably large molecules across nasal mucosa by means of specially designed, highly adaptable carriers loaded with said molecules. One of the purposes of making such formulations is to achieve non-invasive systemic delivery of therapeutic polypeptides, proteins and other macromolecules; the other intent is to overcome circumstantially the blood-brain barrier by exploiting the nasal cavity to enter the body and then to get access to the brain. A third intent is to achieve successful protective or tolerogenic immunization via nasal antigen or allergen administration.

56 Claims, 24 Drawing Sheets

U.S. PATENT DOCUMENTS

| | | |
|---|---|---|
| 6,276,598 B1 | 8/2001 | Cheng |
| 6,277,892 B1 | 8/2001 | Deckner et al. |
| 6,294,192 B1 | 9/2001 | Patel et al. |
| 6,303,141 B1 | 10/2001 | Fischer et al. |
| 6,333,044 B1 * | 12/2001 | Santus et al. ............ 424/434 |
| 6,387,383 B1 | 5/2002 | Dow et al. |
| 6,448,296 B2 | 9/2002 | Yasueda et al. |
| 6,451,339 B2 | 9/2002 | Patel et al. |
| 6,517,864 B1 | 2/2003 | Jacobsen |
| 6,562,370 B2 | 5/2003 | Luo et al. |
| 6,577,880 B1 | 6/2003 | Ishida et al. |
| 6,582,724 B2 | 6/2003 | Hsu et al. |
| 6,586,000 B2 | 7/2003 | Luo et al. |
| 6,645,520 B2 | 11/2003 | Hsu et al. |
| 6,645,529 B2 | 11/2003 | Gergely et al. |
| 6,673,363 B2 | 1/2004 | Luo |
| 6,726,598 B1 | 4/2004 | Jarvis et al. |
| 6,726,925 B1 | 4/2004 | Needham |
| 6,797,276 B1 | 9/2004 | Glenn et al. |
| 6,835,392 B2 | 12/2004 | Hsu et al. |
| 6,868,686 B2 | 3/2005 | Ueda et al. |
| 7,063,859 B1 | 6/2006 | Kanios |
| 7,175,850 B2 | 2/2007 | Cevc |
| 7,387,788 B1 | 6/2008 | Carrara |
| 7,459,171 B2 | 12/2008 | Cevc |
| 7,473,432 B2 | 1/2009 | Cevc |
| 7,591,949 B2 | 9/2009 | Cevc |
| 2001/0012849 A1 | 8/2001 | Wechter |
| 2002/0003179 A1 | 1/2002 | Verhoff et al. |
| 2002/0012680 A1 | 1/2002 | Patel et al. |
| 2002/0037877 A1 | 3/2002 | Singh |
| 2002/0048596 A1 | 4/2002 | Cevc et al. |
| 2002/0106345 A1 | 8/2002 | Uhrich et al. |
| 2002/0119188 A1 | 8/2002 | Niemiec et al. |
| 2002/0147238 A1 | 10/2002 | Jerussi et al. |
| 2003/0099694 A1 | 5/2003 | Cevc et al. |
| 2004/0071767 A1 | 4/2004 | Cevc et al. |
| 2004/0105881 A1 | 6/2004 | Cevc et al. |
| 2005/0123897 A1 | 6/2005 | Cevc et al. |
| 2007/0031483 A1 | 2/2007 | Cevc |
| 2007/0042030 A1 | 2/2007 | Cevc |
| 2007/0184114 A1 | 8/2007 | Cevc |
| 2007/0243203 A1 | 10/2007 | Abrecht |
| 2008/0095722 A1 | 4/2008 | Cevc |
| 2008/0279815 A1 | 11/2008 | Cevc |
| 2008/0311184 A1 | 12/2008 | Cevc |
| 2009/0042989 A1 | 2/2009 | Cevc |
| 2009/0060989 A1 | 3/2009 | Cevc |
| 2009/0060990 A1 | 3/2009 | Cevc |
| 2009/0155235 A1 | 6/2009 | Cevc |

FOREIGN PATENT DOCUMENTS

| | | |
|---|---|---|
| AU | 724218 | 9/2000 |
| CA | 1143656 | 3/1983 |
| CA | 1289420 | 9/1991 |
| CA | 2067754 | 2/1992 |
| CA | 2052164 | 9/1992 |
| CA | 2160775 | 11/1994 |
| DE | 3016976 | 11/1980 |
| DE | 3713494 | 10/1987 |
| DE | 40 26 834.9 | 8/1990 |
| EP | 0088046 | 9/1983 |
| EP | 0102324 | 3/1984 |
| EP | 0152379 | 8/1985 |
| EP | 0224837 | 11/1986 |
| EP | 0211647 | 2/1987 |
| EP | 0220797 | 5/1987 |
| EP | 0298280 | 6/1988 |
| EP | 0280492 | 8/1988 |
| EP | 0393707 | 10/1990 |
| EP | 0475160 | 3/1992 |
| EP | 0355095 | 8/1993 |
| EP | 0582239 | 2/1994 |
| EP | 0674913 | 4/1995 |
| EP | 0704206 | 4/1996 |
| EP | 0707847 | 4/1996 |
| EP | 0382716 | 1/1998 |
| EP | 0995435 | 4/2000 |
| EP | 1031347 | 4/2002 |
| EP | 1031346 | 5/2002 |
| JP | 61-271204 | 12/1986 |
| JP | 4-210925 A | 8/1992 |
| JP | 5-502042 A | 4/1993 |
| JP | 6-183954 A | 7/1994 |
| JP | 6-507420 A | 8/1994 |
| JP | 07-324029 | 12/1995 |
| JP | 8-183742 A | 7/1996 |
| WO | WO-87/01938 | 4/1987 |
| WO | WO-88/07362 | 10/1988 |
| WO | WO 90/09385 | 8/1990 |
| WO | WO-90/09782 | 9/1990 |
| WO | WO-90/11065 | 10/1990 |
| WO | WO-91/01146 | 2/1991 |
| WO | WO-91/01596 | 2/1991 |
| WO | WO-91/04013 | 4/1991 |
| WO | WO-92/03122 | 3/1992 |
| WO | WO 92/04009 | 3/1992 |
| WO | WO-92/05771 | 4/1992 |
| WO | WO-92/22292 | 12/1992 |
| WO | WO-93/19736 | 10/1993 |
| WO | WO-93/19737 | 10/1993 |
| WO | WO-94/26257 | 11/1994 |
| WO | WO-95/09831 | 4/1995 |
| WO | WO-95/35095 | 12/1995 |
| WO | WO-96/04526 | 2/1996 |
| WO | WO-96/19205 | 6/1996 |
| WO | WO-96/29999 | 10/1996 |
| WO | 97/35573 A2 | 10/1997 |
| WO | WO-98/05539 | 2/1998 |
| WO | WO-98/06750 | 2/1998 |
| WO | WO-98/07414 | 2/1998 |
| WO | WO-98/17255 | 4/1998 |
| WO | WO 98/17255 * | 4/1998 |
| WO | WO 00/24377 | 5/1998 |
| WO | WO-98/20734 | 5/1998 |
| WO | WO-98/24407 | 6/1998 |
| WO | WO-98/30215 | 7/1998 |
| WO | WO-98/33483 | 8/1998 |
| WO | WO-99/22703 | 5/1999 |
| WO | WO-00/00597 | 1/2000 |
| WO | WO-00/12060 | 3/2000 |
| WO | WO-00/13684 | 3/2000 |
| WO | WO-00/24377 | 5/2000 |
| WO | WO-00/25822 | 5/2000 |
| WO | WO-00/38653 | 7/2000 |
| WO | WO-00/44349 | 8/2000 |
| WO | WO-00/44350 | 8/2000 |
| WO | WO-00/50007 | 8/2000 |
| WO | WO-01/00247 | 1/2001 |
| WO | WO-01/01962 | 1/2001 |
| WO | WO-01/01963 | 1/2001 |
| WO | WO-01/12155 | 2/2001 |
| WO | WO-02/07767 | 1/2002 |
| WO | WO-02/11683 | 2/2002 |
| WO | WO-02/32398 | 4/2002 |
| WO | WO-02/058670 | 8/2002 |
| WO | WO-2004/032900 | 4/2004 |
| WO | WO-2005/063213 | 7/2005 |
| WO | WO-2006/050926 | 5/2006 |

OTHER PUBLICATIONS

Clark, J.M., Jr. "Experimental Biochemistry", Biochemistry Division, Department of Chemistry, University of Illinois, 1st Edition, pp. 47-48, Dec. 2, 1997.*

Karzel and R.K. Liedtke, "Mechanism Transkutaner Resorption", on Grandlagen/Basics, 1989, pp. 1487-1491.*

Patel, H.M., "Liposomes as a Controlled-release System", Biomedical Society Transactions, 1985, 609th Meeting, Lees, pp. 513-516.*

Price, C.E. "A Review of the Factors Influencing the Penetration of Pesticides Through Plant Leaves", on I.C.I Ltd., Plant Protection Division, Jealott's Hill Research Station, Bracknell, Berkshire, RG12 6EY, U.K., 1982, pp. 237-252.*

Siddiqui, O. et al. "Nonparenteral Administration of Peptide and Protein Drugs", CRC Critical Reviews in Therapeutic Drug Carrier Systems, 1987, vol. 3, Issue 3, pp. 195-208.*

Bibliographic page and claims granted in US Pat. 6,165,500, Dec. 26, 2000.*
Bibliographic page and granted claims of US Patent No. 7,473,423, Jan. 6, 2009.*
Bibliographic page and granted claims of US Patent No. 7,459,171, Dec. 2, 2008.*
Partial European Search Report issued in counterpart European Appln. No. 99101480 (granted as EPO Patent No. 1 031 347 B1), Apr. 4, 2000.*
Examination Reports issued in counterpart European Appln. No. 99101480 (granted as EPO Patent No. 1 031 347 B1), Sep. 15, 2000.*
Bibliographic page and English language claims of granted counterpart EPO Patent No. 1 031 347 B1 (counterpart of European Appln. No. 99101480), Jan. 27, 1999.*
Information Disclosure Statements submitted in U.S. Appl. No. 09/890,335, filed Dec. 30, 2003.*
Information Disclosure Statements submitted in U.S. Appl. No. 09/890,335, filed Jan. 30, 2004.*
Information Disclosure Statements submitted in U.S. Appl. No. 09/890,335, filed Oct. 27, 2006.*
Information Disclosure Statements submitted in U.S. Appl. No. 09/890,335, filed Jul. 17, 2009.*
Information Disclosure Statements submitted in U.S. Appl. No. 09/890,335, filed Jun. 6, 2010.*
English version of claims pending in U.S. Appl. No. 09/890,371's counterpart Japanese application as of date of issuance of Japanese Office Action, Aug. 3, 2001.*
Almeida, A.J., et al., Nasal delivery of vaccines, J. Drug Targeting, 3:455-467 (1996).
Bagnasco, M. et al, Absorption and distribution kinetics of the major Parietaria judaica allergen (Par j 1) administered by noninjectable routes in healthy human beings, J. Allergy Clin. Immunol (1997) 100: 122-9.
Biberoglu, K., et al., Treatment of estrogen-dependent gynecological disorders with the gonadotropin releasing hormone agonist buserelin, Gynecol. Endocrinol. 1991; 5: 109-22.
Bruins, J., et al., Effect of acute and chronic treatment with desglycinamide-[Arg$^8$]Vasopressin in young male and female volunteers. Peptides, 1995; 16: 179-86.
Cevc, G., et al., Drug delivery across the skin, Exp. Opin. Invest. Drugs (1997)6: 1887-1937.
Cevc, G., Transferosomes, liposomes and other lipid suspensions on the skin: Permeation enhancement, vesicle penetration, and transdermal drug delivery, Critical Reviews in Therapeutic Drug Carrier Systems, 13(3&4):257-388 (1996).
Cevc, G., et al., Ultraflexible vesicles, transfersomes, have an extremely low permeation resistance and transport therapeutic amounts of insulin across the intact mammalian skin. Biochim. Biophys. Acta 1998; 1368: 201-215.
Draghia, R., et al., Gene delivery into the central nervous system by nasal instillation in rats. Gene-Ther. 1995; 2: 418-23.
Drejer, K., et al., Intranasal administration of insulin with phospholipid as absorption enhancer: pharmacokinetics in normal subjects, Diab. Med. 1992, 9:335-340.
Flanagan, B., et al., A recombinant human adenovirus expressing the simian immunodeficiency virus Gag antigen can induce long-lived immune responses in mice, J. Gen. Virol. 1997; 78: 991-7.
Gizurarson, S., et al., Intranasal administration of insulin to humans. Diabetes Res. Clin. Pract. May 1991; 12: 71-84.
Ghigo, E.; et al., Short-term administration of intranasal or oral Hexarelin, a synthetic hexapeptide, does not desensitize the growth hormone responsiveness in human aging. Eur. J. Endocrinol. 1996; 135: 407-12.
Harris, AS, Review: clinical opportunities provided by the nasal administration of peptides. J. Drug Target. 1993; 1: 101-16.
Huneycutt, BS, et al., Distribution of vesicular stomatitis virus proteins in the brains of BALB/c mice following intranasal inoculation: an immunohistochemical analysis, Brain Res. 1994; 635: 81-95.
Hussain A., et al., Does increasing the lipophilicity of peptides enhance their nasal absorption? J. Pharm. Sci. 1991; 80: 11 80-1.
Ichikawa-M, et al., Anti-osteopenic effect of nasal salmon calcitonin in type 1 osteoporotic rats: comparison with subcutaneous dosing, Biol. Pharm. Bull. 1994; 17: 911-13.

Ilum, L., The nasal delivery of peptides and proteins. Trends Biotechnol. 1991; 9: 284-9.
Ilum, L.; et al., Intranasal insulin. Clinical pharmacokinetics. Clin. Pharmacokinet. Jul. 1992; 23: 30-41.
Invitti, C., et al., Effect of chronic treatment with octreotide nasal powder on serum levels of growth hormone, insulin-like growth factor I, insulin-like growth factor binding proteins 1 and 3 in acromegalic patients, J. Endocrinol. Invest. 1996; 19: 548-55.
Kida, S., et al., CSF drains directly from the subarachnoid space into nasal lymphatics in the rat. Anatomy, histology and immunological significance. Neuropathol. Appl. Neurobiol. 1993; 19: 480-448.
Laursen, T., et al., Bioavailability and bioactivity of three different doses of nasal growth hormone (GH) administered to GH-deficient patients: comparison with intravenous and subcutaneous administration, Eur. J. Endocrinol. 1996; 135: 309-15.
Machida, M., et al., Absorption of recombinant human granulocyte colony-stimulating factor (rhG-CSF) from rat nasal mucosa, Pharm. Res. 1993; 10(9): 1372-7.
Maejima, K.; et al., Comparison of the effects of various fine particles on IgE antibody production in mice inhaling Japanese cedar pollen allergens. J. Toxicol. Environ. Health. 1997; 52: 231-48.
Maitani, Y., et al., Influence of molecular weight and charge on nasal absorption of dextran and DEAE-dextran in rabbits, Int'l. J. Pharmaceut. 1989; 49: 23-27.
McMartin, C., et al., Analysis of structural requirements for the absorption of drugs and macromolecules from the nasal cavity, J. Pharm. Sci. 1987; 76: 535-540.
Mori, I., et al., Temperature-sensitive parainfluenza type 1 vaccine virus directly accesses the central nervous system by infecting olfactory neurons. J. Gen. Virol. 1996; 77: 2121-4.
Naumann, E., et al., Vasopressin and cognitive processes: two event-related potential studies. Peptides. 1991; 12: 1379-84.
Pasechnik, V., et al., Macromol cular drug delivery to the CNS with protein carriers Exp. Opin. Invest. Drugs 1996, 5:1255-1276.
Paul, A,. et al., Non-invasive Administration of Protein Antigens: Transdermal Immunization with Bovine Serum Albumine in Transfersomes. Vaccine Res. 1995; 4(3):145-164.
Perras, B., et al., Sleep and signs of attention during 3 months of intranasal vasopressin: a pilot study in two elderly subjects. Peptides. 1996; 17: 1253-55.
Pietrowsky, R., et al., Brain potential changes after intranasal vs. intravenous administration of vasopressin: Evidence for a direct nose-brain pathway for peptide effects in humans. Biol. Psychiatry. 1996; 39: 332-40.
Pihoker, C., et al., Diagnostic studies with intravenous and intranasal growth hormone-releasing peptide-2 in children of short stature. J. Clin. Endocrinol. Metab. 1995; 80(10): 2987-92.
Pohl, J., et al., Modulation of pain perception in man by a vasopressin analogue. Peptides. 1996; 17: 641-7.
Sarkar, MA, Drug metabolism in the nasal mucosa. Pharm-Res. 1992; 9: 1-9.
Shimoda, N., et al., Effects of dose, pH and osmolarity on intranasal absorption of recombinant human erythropoietin in rats, Biol. Pharm. Bull. 1995; 18(5): 734-9.
Sperber, S.J., et al., Otologic effects of interferon beta serine in experimental rhinovirus colds, Arch. Otolaryngol. Head. Neck. Surg. 1992; 118: 933-6.
Ting, T.Y., et al., Microparticles of polyvinyl alcohol for nasal delivery. I. Generation by spray-drying and spray-desolvation, Pharm. Res. 1992; 9: 1330-5.
Tsume, Y, et al., Quantitative evaluation of the gastrointestinal absorption of protein into the blood and lymph circulation, Biol. Pharm. Bull. 1996; 19(10): 1332-1337.
Watanabe, Y., et al., Absorption of recombinant human granulocyte colony-stimulating factor (rhG-CSF) and blood leukocyte dynamics following intranasal administration in rabbits, Biol. Pharm. Bull. 1993; 16: 93-5.
Watanabe, Y., et al., Pharmacokinetics and pharmacodynamics of recombinant human granulocyte colony-stimulating factor (rhG-CSF) following intranasal administration in rabbits, J. Drug Target. 1995; 3: 231-38.

Wearley, L.L., Recent progress in protein and peptide delivery by noninvasive routes, Crit. Rev. Ther. Drug Carrier Syst. 1991; 8: 331-94.

Westenberg, H.G., et al., Pharmacokinetics of DGAVP in plasma following intranasal and oral administration to healthy subjects, Peptides, 1994; 15: 1101-4

Van der Wiel, H.E., et al, Intranasal calcitonin suppresses increased bone resorption during short-term immobilization: A double-blind study of the effects of intranasal calcitonin on biochemical parameters of bone turnover. J. Bone Mineral Res. 1993; 8:1459-65.

U.S. Appl. No. 09/890,335, filed Jul. 26, 2001, Ceve et al.

Deng et al., "Sustainable Cutaneous Gene Delivery", Nature Biotechnology 15:1388-1390 (1997).

Ellis, R. "New Technologies for Making Vaccines", Vaccines 29:568-574 (1998).

Fries et al., "Evidence of Fibroblast Heterogeneity and the Role of Fibroblast Subpopulations in Fibrosis", Clin. Immunol. Immunopathol. 72(3):283-292 (1994).

Glenn et al., "Skin Immunization Made Possible by Cholera Toxin", Nature 391(6670):851 (1998).

Glenn et al., "Transcutaneous Immunization with Cholera Toxin Protects Mice Against Lethal Mucosal Toxin Challenge", J. Immunol. 161:3211-3214 (1998).

Kondo et al., "Epidermal Cytokines in Allergic Contact Dermatitis", J. Am. Acad. Dermatol. 33:786-800 (1995).

Lohoff et al., "The Th1/Th2 Paradigm and Experimental Murine Leishmaniasis", Int. Arch. Allergy Immunol. 115:191-202 (1998).

Luger et al., "The Role of Cytokines and Neuroendocrine Hormones in Cutaneous Immunity and Inflammation", Allergy 50:292-302 (1995).

Nasir et al., "Contact Dermatitis. Clinical Perspectives and Basic Mechanisms", Clin. Rev. Allergy and Immunol, 14:151-184 (1996).

Pastore et al., "Granulocyte Macrophage Colony Stimulating Factor is Overproduced by Keratinocytes in Atopic Dermatitis: Implications for Sustained Dendritic Cell Activation in the Skin", J. Clin. Invest. 99:3009-3017 (1997).

Paul et al., Transdermal Immunisation with Large Proteins by Means of Ultradeformable Drug Carriers, Eur. J. Immunol. 25:3521-3524 (1995).

Schatzlein et al., "Non-uniform Cellular Packing of the Stratum Corneum and Permeability Barrier Function of Intact Skin: a High Resolution Confocal Laser Scanning Microscopy Study Using Highly Deformable Vesicles (Transfersomes)", Br. J. Dermatol. 138:583-592 (1998).

Strange et al., "*Staphylococcal* Enterotoxin B Applied on Intact Normal and Intact ATopic Skin Induces Dermatoma", Arch. Dermatol. 132-27-33 (1996).

Wang et al., "Epicutaneous Exposure of Protein Antigen Induces a Predominant Th2-like Response with IgE Production in Mice" J. Immunol. 156:4079-4082 (1996).

Agerholm, C., et al. Epithelial Transport and Bioavailability of Intranasally Administered Human Growth Hormone Formulated with the Absorption Enhancers Didecanoyl-L-α-phosphatidylcholine and α-Cyclodextrin in Rabbits. J. of Pharmaceutical Sciences. vol. 83, No. 12, pp. 1706-1711. Dec. 1994.

Vinggaard, A.M., et al. Didecanoyl Phosphatidylcholine is a Superior Substrate for Assaying Mammalian Phospholipase D. Biochem. J. (1996) 319, 861-864.

Pierson et al., "Synthesis and biological evaluation of potent, selective, hexapeptide CCK-A agonist anorectic agents" J. Med. Chem. 40:4302-07 (1997).

Lee et al., "Intranasal bioavailability of insulin powder formulations: Effect of permeation enhancer-to-protein ratio" J. Pharm. Sci. 80(8):725-29 (1991).

Shao et al., "Cyclodextrins as nasal absorption promoters of insulin: Mechanistic evaluations" Pharm. Res. 9 (9):1157-63 (1992).

Illum et al., "Chitosan as a novel nasal delivery system for peptide drugs" Pharm. Res. 11(8):1186-89 (1994).

Lowell et al., "Proteosomes, emulsomes, and cholera toxin B improve nasal immunogenicity of human immunodeficiency virus gp160 in mice: Induction of serum, intestinal, vaginal, and lung IgA and IgG" J. Infect. Dis. 175:292-301 (1997).

Office Action issued on Jul. 29, 2009 in U.S. Appl. No. 09/890,335, currently pending.

Office Action issued in U.S. Appl. No. 11/667,325 on Jul. 13, 2009, currently pending.

Office Action issued in U.S. Appl. No. 09/284,683 on Jul. 23, 2009, currently pending.

Holum, Elements of General and Biological Chemistry: John Wiley & Sons, USA (1987), pp. 324, 325.

Stryer, Biochemistry: W.H. Freeman & Co., San Francisco, California, USA (1981), pp. 208, 209.

Matthews & van Holde, Biochemistry: The Benjamin/Cummings Publishing Co., Redwood City, California (1990), pp. 303, 304.

Office Actions and Interview Summaries issued Jan 26, 2009; May 1, 2008; Jan. 29, 2008, Jul. 18, 2007 and May 25, 2006 in U.S. Appl. No. 09/890,335, currently pending.

Claims pending on Jan. 26, 2009 and currently pending claims in U.S. Appl. No. 09/890,335.

Office Actions and Notices of Allowability issued on Jan. 3, 2006, Mar. 2, 2005, Jul. 2, 2001 in U.S. Appl. No. 09/621,574, abandoned.

Claims pending on Jan. 3, 2006 in U.S. Appl. No. 09/621,574.

Office Actions and Notices of Allowability issued on May 25, 1999, Jun. 24, 1998 and Dec. 19, 1997 in U.S. Appl. No. 07/844,664, granted as US Pat. 6,165,500.

Office Action issued on Mar. 27, 2007 in U.S. Appl. No. 11/481,804, abandoned.

Claims pending on Mar. 27, 2007 in U.S. Appl. No. 11/481,804.

Office Actions issued Aug. 10, 2006; Dec. 21 & Apr. 1, 2005; Mar. 23, 2004; May 20 & Jan. 9 (Advisory), 2003; Jun. 24, 2002; Sep. 25, 2001 in U.S. Appl. No. 09/555,986, abandoned.

Claims pending on Aug. 10, 2006 in U.S. Appl. 09/555,986.

Office Actions issued Nov. 25, 2008, Apr. 2, 2008, Nov. 29, 2007, Aug. 17, 2007, Mar. 12, 2007, Jul. 10, 2006 in U.S. Appl. No. 09/284,683, currently pending.

Office Actions issued Nov. 4, 2005, Apr. 15, 2005, Jun. 24, 2004, Mar. 18, 2004 (Advisory) in U.S. Appl. No. 09/284,683, currently pending.

Office Actions issued Oct. 7, 2003, Jun. 18, 2003 (Advisory), Jan. 3, 2003, Apr. 10, 2002, Jul. 6, 2001 (Advisory), Apr. 20, 2001, Aug. 22, 2000 in U.S. Appl. No. 09/284,683, currently pending.

Claims pending on Nov. 25, 2008 in U.S. Appl. No. 09/284,683.

Office Actions issued Dec. 30 and Nov. 28, 2008 in U.S. Appl. No. 11/667,325, currently pending.

Claims pending on Dec. 30, 2008 in U.S. Appl. No. 11/667,325.

Office Actions issued on May 26, 2009; Oct. 28 & Mar. 19, 2008; Aug. 2, 2007; and Dec. 28, 2006 in U.S. Appl. 10/357,618, currently pending.

Claims pending on May 26, 2009 in U.S. Appl. No. 10/357,618.

Office Actions & Notices of Allowability issued Oct. 16, 2008, Sep. 21 & Jan. 19, 2007, & May 30, 2006 in U.S. Appl. No. 10/357,617, granted as US Patent No. 7,473,432.

Office Actions and Notice of Allowance issued on May 29, 2009, May 16, 2007, Aug. 28, 2006 and Feb. 7, 2006 in U.S. Appl. 10/984,450, allowed.

Claims pending on May 29, 2009 in U.S. Appl. No. 10/984,450.

Office Actions, Notices of Allowability issued Aug. 21 & Jan. 9, 2008, Apr. 11, 2007, Sep. 20, 2006, Dec. 19 & Mar. 30, 2005, Apr. 21, 2004 Oct. 16, 2006 in U.S. Appl. No. 10/037,480, granted as US Patent 7,459,171, Office Actions issued Oct. 19, 2005, Feb. 2, 2005, May 27, 2004 (Advisory), Nov. 4, 2003, Jun. 17, 2003, Nov. 29, 2002, in US Appl. 09/887,493, granted (US 7,175,850).

Notice of Allowability dated Sep. 12, 2006 in U.S. Appl. No. 09/887,493, and bibliographic page and granted claims of US Patent No. 7,175,850.

Office Action issued Oct. 23, 2008 in U.S. Appl. No. 11/638,091, currently pending, Examiner Coe.

Claims pending on Oct. 23, 2008 in U.S. Appl. No. 11/638,091.

International Search Report issued in counterpart PCT Application No. PCT/EP00/00598 (published as WO 00/44350).

Written Opinion issued in counterpart PCT Application No. PCT/EP00/00598 (published as WO 00/44350).

International Preliminary Examination Report issued in counterpart PCT Application No. PCT/EP00/00598 (published as WO 00/44350).
"Itching" (2006) From Merck Manual Home Edition Online: www.merck.com/mmhe/pring/sec18/ch203/ch203b.html.
Almeida et al., "Nasal delivery of vaccines," Journal of Drug Targeting, vol. 3, No. 6, pp. 455-467 (1996).
Aungst et al., "Enhancement of Naloxone Penetration Through Human Skin In Vitro Using Fatty Acids, Fattty Alcohols, Surfactants, Sulfoxides and Amides," on Internaitonal Journal of Pharmaceutics, 33 (1986) pp. 225-234.
Benner, "The Human Body, The Wonderwork of the Human Body, Structure, Functions, Interactions, Processes and Mechanisms," Weltbild GmbH Augsburg (1995).
Berger, M. Oral insulin 1922-1992: The History of Continuous Ambition and Failure Heinrich-Heine-University, Dusseldorf, Germany.
Beyer, C. et al., "Micro Emulsions" Pharmazie in unserer Zeit, No. 2 (1983).
Blume, et al., "Drug-Carrier and Stability Properties of the Long-Lived Lipid Vesicles, Cryptosomes, In Vitro and In Vivo," Journal of Liposome Research, 2(3), 355-368 (1992).
Brendzel, A. et al., "Effects of Lipid-Soluble Substances on the Thermotropic Properties of Liposome Filtration," Biochimica et Biophysica Acta, 601 (1980) 260-270.
Burnette, R. et al., "Characterization of the Permselective Properties of Excised Human Skin During Lontophoresis," Journal of Pharmaceutical Sciences/ vol. 76, No. 10, Oct. 1987 pp. 765-773.
Byas-Smith et al., "Transdermal clonidine compared to placebo in painful diabetic neuropathy using two stage 'enriched enrollment' design," Pain, vol. 60, pp. 267-274 (1995).
Calpena, et al., "Influence of the Formulation on the In Vitro Transdermal Penetration of Sodium Diclofenac," Arzneim.-Forsch./Drug Res, 49(II), 1012-1017 (1999).
Carafa, M. et al. "Lidocaine-loaded Non-ionic Surfactant Vesicles: Characterization and In Vitro Permeation Studies," International Journal of Pharmaceuticals 231 (2002) 21-32.
Castillo et al., "Glucocorticoids Prolong Rat Sciatic Nerve Blockade In Vivo from Bupivacaine Microspheres," Anesthesiology, vol. 85, No. 5, pp. 1157-1166 (1996).
Cevc et al., "Phospholipids handbook", Marcel Dekker, Inc., New York, Basel, Hong Kong, pp. 375-376 and 404 (1993).
Cevc et al.: "Transdermal drug carriers: basic properties, optimization and transfer efficiency in the case of epicutaneously applied peptides," J. Contr. Rel., 36, pp. 3-16, 1995.
Cevc, "Transfersomes, Liposomes, and Other Lipid Suspensions on the Skin: Permeation Enhancement, Vesicle Penetration, and Transdermal Drug Delivery," Crit. Rev. Ther. Drug Carrier Syst., 13 (3&4), pp. 257-388, 1996.
Cevc, G. et al." New, Highly Efficient Formulation of Diclofenac for the Topical, Transdermal Administration in Ultradeformable Drug Carriers, Transfersomes," Biochimica et Biophysica Acta 1514 (2001) 191-205.
Cevc, G. et al., "The skin: a pathway for systemic treatment with patches and lipid-based agent carriers" Advanced Drug Delivery Reviews 18 pp. 349-378 (1996).
Cevc, G. et al., "Transfersomes-mediated transepidermal delivery improves the regio-specificity and biological activity of corticosteriods in vivo," Journal of Controlled Release, vol. 45, No. 3, 1997, pp. 211-226.
Cevc, G., "Material Transport Across Permeabilitiy Barriers by Means of Lipid Vesicles", *Handbook of Biological Physics*, vol. 1, pp. 465-490 (1995).
Claims (pending) filed Feb. 9, 2007, in connection with U.S. Appl. No. 09/555,986, under examination of the USPTO.
Claims (pending) filed May 8, 2007, in connection with U.S. Appl. No. 11/667,325.
Claims filed Feb. 26, 2007, in connection with U.S. Appl. No. 10/984,450 (U.S. Patent Publication No. US 2005/0123897 A1), under examination of the USPTO
Claims filed Jan. 22, 2007, in connection with U.S. Appl. No. 10/037,480 (U.S. Patent Publication No. US 2003/0099694 A1), under examination of the USPTO.
Claims filed Jul. 12, 2007, in connection with U.S. Appl. No. 09/284,683 (U.S. Patent Publication No. US 2002/0048596 A1), under examination of the USPTO.
Claims filed Jun. 20, 2007, in connection with U.S. Appl. No. 10/357,618 (U.S. Patent Publication No. US 2005/0105881 A1), under examination of the USPTO.
Claims filed Oct. 11, 2006, in connection with U.S. Appl. No. 11/545,904 (U.S. Patent Publication No. US 2007/0031483 A1), under examination of the USPTO.
Claims filed Oct. 20, 2006, in connection with U.S. Appl. No. 10/357,617 (U.S. Patent Publication No. US 2004/0071767 A1), under examination of the USPTO.
International Search Report for International Patent Application No. PCT/EP2005/011986. (Jul. 4, 2006).
Definition of Microbicide, Wikipedia, The Free Online encyclopedia (2007).
Edwards, et al., Effects of Triton X-100 on Sonicated Lecithin Vesicles, Langmuir, vol. 5, pp. 472-475 (1989).
Fieser, L. F. et al. "Organische Chemie," Hans Ruprecht Hensel, 2nd revised edition, Verlag Chemie GmbH, Weinheim/Bergstr. p. 1250 (1968).
Fluka Chemica-BioChemica, Katalog 16, pp. 204, 830 (1988/1989).
Foldvari, "Effect of Vehicle on Topical Liposomal Drug Delivery: Petrolatum Bases," J. Microencapsulation, 1996, vol. 13, No. 5, 589-600.
Foldvari, "In Vitro cutaneous and Percutaneous Delivery and in Vivo Efficacy of Tetracaine from Liposomal and Conventional Vehicles," Pharmaceutical Research, vol. 11, No. 11, 1994.
Foldvari, et al., "Dermal Drug Delivery by Liposome Encapsulation: Clinical and Electron Microscopic Studies," J. Microencapsulation, 1990, Vol. 7, No. 4, 479-489.
Frantzen et al., "Assessing the accuracy of routine Photon Correlation Spectroscopy Analysis of Heterogeneous Size Distributions," AAPS PharmSciTech, vol. 4, No. 3, Article 36, pp. 1-9 (2003).
Friedrich, I. et al., "Physicochemical Characterization of a Reverse Micellar Solution after Loading with Different Drugs," Pharmazie 55 (2000) 10, 755-758.
Gesztes, A. et al., Topical Anesthesia of the Skin by Liposome-Encasulated Tetracaine, Anesth Analg 1988 67 1079-1081.
Golden et al., "Role of Stratum Corneum Lipid Fluidity Transdermal Drug Flux," on Journal of Pharmaceutical Sciences vol. 76, No. 1, Jan. 1987, American Pharmaceuticals Association, pp. 25-28.
Grahame R, "Transdermal non-steroidal anti-inflammatory agents," BJCP, vol. 49, No. 1, pp. 33-35 (Jan.-Feb. 1995).
Green et al., "In Vitro and In Vivo Enhancement of Skin Permeation with Oleic and Lauric Acids," on International Journal of Pharmaeuticals, 48 (1988), pp. 103-111.
Helenius, et al.: "Solubilization of Membranes by Detergents," Biochimica et Biophysica Acta, 415 (1975) 29-79.
Henmi, T. et al., "Application of an Oily Gel Formed by Hydrogenated Soybean Phgospholipids as a Percutaneous Absorption-Type Ointment Base," Chem. Pharm. Bull. 42(3) 651-655 (1994).
Holzbach RT, "Detection of Vesicles in native and model Biles by Morphological and other structural Techniques: applications and limitations," Hepatology, Sep12 (3 Pt 2), pp. 106S-112S (1990).
Ito, Yoshimasa et al. "Percutaneous Absorption of Acemetacin from a Membrane Controlled Transdermal System and Prediction of the Disposition of the Drug in Rats." Biol. Pharm. Bull., 16(6):583-588. (1993).
Jackson, M. L. et al. "Solubilization of Phospatidylcholine Bilayers by Octyl Glucoside" Biochemistry, vol. 21, pp. 4576-4582 (1982).
Katoulis et al., "Efficacy of a New Needeless Insulin Delivery System Monitoring of Blood Glucose Fluctuations and Free Insulin Levels," on International Journal of Artificial Organs vol. 12, No. 5, 1989, pp. 333-338.
Kilbanov, et al., Activity of amphipathic poly(ethylene glycol) 5000 to prolong the circulation time of liposomes depends on the liposome size and is unfavorable for immunoliposome binding to target, BBA, 1062, pp. 141-148, 1991.
Knepp et al., "Controlled Drug Release From a Novel Liposomal Delivery System II. Transdermal Delivery Characteristics," Journal of Controlled Release 12 (Mar. 1990) No. 1, Amsterdam, NL, pp. 25-30.

Lasch, J. et al., "Interactions of external lipids (lipids vesicles) with the skin" Journal of Liposome Research 5(3) pp. 543-569 (1995).
Lehmann, J. et al. "Analgesic and anti-inflammatory efficacy of IDEA-070 in UVB-induced sunburn." Journal of the European Academy of Dermatology and Venereology, 18(S2):167-168. (Oct. 2004).
Litchenberg, D. et al., "Solubilization of Phospholipids by Detergents Structural and Kinetic Aspects" Biochemica et Biophysica Acta, 737 pp. 285-304 (1983).
Lobbecke, et al," Effects of Short-Chain Alcohols on the Phase Behavior and Interdigitation of Phospatidylcholine Bilayer Membranes," Biochimiea et Biophysica Aeta 1237 (1995) 59-69.
Mayer, L.D. et al., "Vesicles of variable sizes produced by a rapid extrusion procedure," Biochemica et Biophysica Acta, 858 pp. 161-165 (1986).
Merck Index: 10th Edition. 1983, pp. 779-780.
Mezei, "Liposomes as a Skin Drug Delivery System," 1985 Elsevier Science Publishers B.V. (Biomedical Division), pp. 345-358.
Ogiso, Taro et al. "Membrane-Controlled Transdermal Therapeutic System Containing Clonazepam and Anticonvulsant Activity after its Application." Chem. Pharm. Bull., 37(2):446-449. (1989).
Patel, H.M. et al., Oral Adimistration of Insulin by Encapsulation Within Liposomes,' Febs Letters, 62(1):60-63 (Feb. 1976).
Paul et al., "Transdermal immunisation with an integral membrane component, gap junction protein, by means of ultradeformable drug carriers, transfersomes," Vaccine, vol. 16, No. 2-3, pp. 188-195 (Jan. 1998).
Peters, et al., "Pharmacodynamics of a Liposomal Preparation for Local Anaesthesia," Arzneim.-Forsch./Dru Res. 45(II), Nr 12 (1995).
Planas, et al., "Noninvasive Percutaneous Induction of Topical Analgesia by a New Type of Drug Carrier, and Prolongation of Local Pain Insensitivity by Anesthetic Liposomes," Anesth Analg. 1992, 75 615-621.
Product Information, "Polysorbate 80 VG" (2004).
Product Information, "Tween 80 Pure" (2004).
Prof. Dr. K-U Benner, Der Korper des Menschen, Chapter 4, p. 49 (1995).
Ranade V., "Drug Delivery Systems.6. Transdermal Drug Delivery," J. Clin Pharmacol, vol. 31, pp. 401-418 (1991).
Roeding, J. "Liposomes and Niosomes in Pharmacy and Cosmetics State of Art Prospects, Techniques of Visualizing Vesicular Systems, Interaction of Liposomes with the Skin" Training Course No. 105 from May 14-16, 1990. Maritim Hotel Nurnberg, Frauentorgraben 11, 8500 Nurnberg.
Schramlova, J. et al., "The Effect of an Antiphlogisitc Incorporated in Liposomes on Experimentally Induced Inflammation," Fola Biologica (Praha) 43, 195-199 (1997).
Schreier, H. "Liposomes—A Novel Drug Carrier, I. Phospholipids; Production and Characterization of Liposomes; II. Destiny of liposomes in vivo; use in therapy," Pharmazie in unserer Zeit, No. 4 (1982).
SERVA Feinbiochemica, Katalog, pp. 201-202 (1986/1987).
Stoye, I. et al., Transformation of a Liposomal Dispersion Containing Ibuproen Lysinate and Phospholipids into Mixed Micelles—Physico-chemical Characterization and Influence on Drug Permeation through Excised Human Stratum Corneum, European Journal of Pharmaceuticals and Biopharmaceuticals 46 (1998) 191-200.
Swenson, E. Scott and William J. Curatolo. "Intestinal permability enhancement for proteins, peptides and other polar drugs: mechanisms and potential toxicity." Advanced Drug Delivery Reviews, 8:39-92. (1992).
Trotta, M. et al., "Deformable liposomes for dermal administration of methotrexate," International Journal of Pharmaceuticals (Kidlington), vol. 270, No. 1-2, Feb. 11, 2004, pp. 119-125.
Trotta, M. et al., "Elastic liposomes for skin delivery of dipotassium glycyrrhizinate," International Journal of Pharmaceuticals (Kidlington), vol. 241, No. 2, Jul. 25, 2002, pp. 319-327.
Valenta, C. et al., "Evalutation of Novel Soya-lecithin Formulations for Dermal use containing Ketoprofen as a Model Drug," Journal of Controlled Release 63 (2000) 165-173.
Vinson, P. et al., "Vesicle-Micelle Transition of Phosphatidylcholine Bilayers by Octyl Glucoside Elucidated by Cryo-Transmission Electron Microscopy," Biophys. J., Biophysical Society vol. 56, Oct. 1989 669-681.
Vyas et al., "Liposomally Encapsulated Diclofenac For Sonophoresis Induced Systemic Delivery," J. Microencapsulation, 1995, vol. 12, No. 2, 149-154.
Wess, L.: "All in the Family." Biocentury, The Bersntein Report on BioBusiness, vol. 12, No. 22, May 17, 2004, pp. A11-A12.
Yuan, et al., "Cationic Liposome and Gene Transfer," Progress in Physiological Science, 28(2), pp. 163-165, 1997.
Y. Aramaki et al., Activation of systemic and mucosal immune response following nasal administration of liposomes Vaccine 12(13):1241-1245 (1994).
Luger and Schwartz, "The role of cytokines and neuroendocrine hormones in cutaneous immunity and inflammation" Allergy 50:292-302 (1995).
Office Action (Restriction Requirement) issued Sep. 18, 2009 and Notice of Abandonment issued Apr. 15, 2010 in U.S. Appl. No. 11/638,091, abandoned.
Office Actions issued Nov. 18, 2009 and Jul. 23, 2008, in pending U.S. Appl. No. 09/284,683; along with claims pending when the Actions were issued and a Notice of References Cited issued with the Nov. 18, 2009 Action.
Office Action and Notice of References Cited issued Jul. 13, 2009 with claims pending when Action issued in pending U.S. Appl. No. 11/667,325.
Office Action and Notice of References Cited issued Feb. 18, 2010 with claims pending when Action issued in pending U.S. Appl. No. 10/357,618.
English Translation/Summary—Beyer C. et al. "Microemulsions" Pharmazie in unserer zeit, No. 2 (1983) (original German language document disclosed in IDS filed on Aug. 6, 2007).
English Translation/Summary—Fieser, L.F. et al.,"Organishe Chemie" Hans Ruprecht Hensel, 2nd revised edition, Verlag Chemie GmbH, WeinheimfBergstr. p. 1250 (1968) (original German language document disclosed in IDS filed on Aug. 6, 2007).
English Translation/Summary—Roeding, J. "Liposomes and niosomes in pharmacy and cosmetics: state of art prospects, techniques of visualizing vesicular systems, interaction of liposomes with the skin" Training course No. 105 from May 14-16, 1990. Maritim Hotel Nurnberg, Frauentrgraben 11, 8500. Nurnberg (original German language document disclosed in IDS filed on Aug. 6, 2007).
English Translation/Summary—Schreier H., "Liposomes—A novel drug carrier I. Phospholipids production; II. Destiny of liposomes in vivo; use in therapy" Pharmazei in unserer Zeit, No. 4 (1982) (original German language document disclosed in IDS filed on Aug. 6, 2007).
Office Action issued Jun. 17, 2010 with claims pending when Action issued in pending U.S. Appl. No. 11/545,904.
In U.S. Appl. No. 09/890,335, indicated as copending at p. 1 of present application: Office Action issued Jul. 29, 2001, claims pending as of Jul. 29, 2009, Examiner Interview Summary dated Dec. 18, 2009, Claims dated Jan. 29, 2010, Examiner Interview Summary dated Mar. 25, 2010, Claims dated Apr. 18, 2010, Claims filed Jul. 3, 2010.

* cited by examiner

Fig. 5

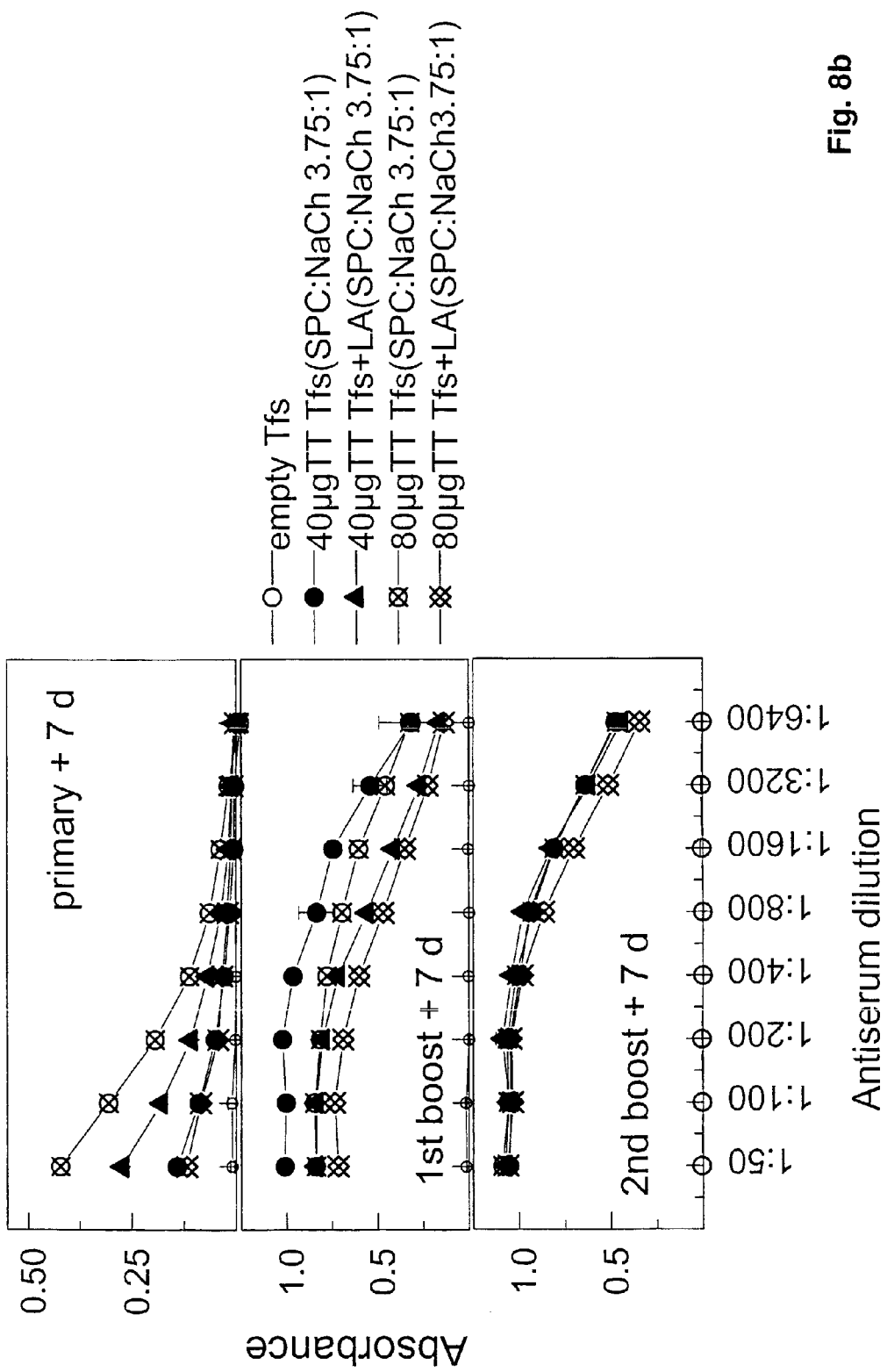

Adjuvant effect: of Heat Labile Toxin (LT) from E.coli

Fig. 14

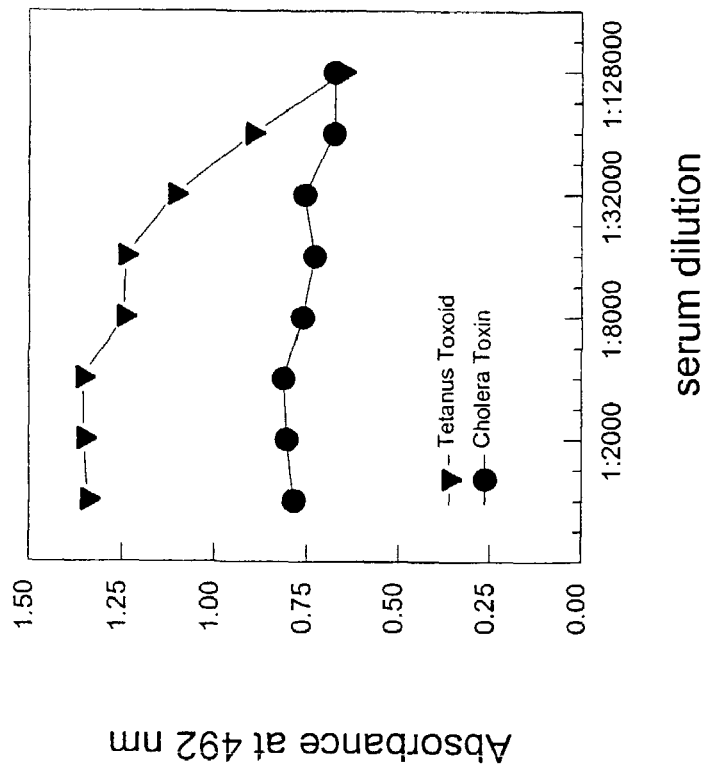
Bi-Valent Vaccines: Anti-Tetanus and -Cholera response to the antigens administration in Transfersomes in

METHODS OF TRANSNASAL TRANSPORT/IMMUNIZATION WITH HIGHLY ADAPTABLE CARRIERS

CROSS-REFERENCE TO RELATED APPLICATIONS

This application is a national stage entry of PCT Application No. PCT/EP00/00598, filed Jan. 26, 2000, which claims priority from European Patent Application No, EP 99101480.4, filed Jan. 27, 1999.

The invention deals with the transport of preferably large molecules across nasal mucosa by means of specially designed, highly adaptable carriers loaded with said molecules. One of the purposes of making such formulations is to achieve non-invasive systemic delivery of therapeutic polypeptides, proteins and other macromolecules; the other intent is to overcome circumstantially the blood-brain barrier by exploiting the nasal cavity to enter the body and then to get access to the brain. A third intent is to achieve successful protective or tolerogenic immunisation via nasal antigen or allergen administration.

Several documents are cited throughout the text of this specification. Each of the documents cited herein (including any manufacturer's specifications, instructions, etc.) are hereby incorporated by reference; however, there is no admission that any document cited is indeed prior art of the present invention. Further incorporated by reference is the complete disclosure content of the co-pending application filed in the name of IDEA AG and bearing the title "Noninvasive vaccination through skin" (U.S. application Ser. No. 09/890,335: published as WO 00/44349).

Nasal delivery has been explored extensively over the last decades and was discussed repeatedly as an alternative to the systemic delivery of drugs, especially peptides and proteins, which normally must be injected. Nasal delivery also attracted interest owing to the fact that it avoids the hepatic first-pass effect, the problem of degradation in nasal cavity notwithstanding, which creates a pseudo-first-pass effect (Sarkar, 1992). The latter difficulty prompted chemical or recombinant structural peptide or protein modifications to improve the stability and minimise the enzymatic cleavage of macromolecules in the nose (Wearley, 1991).

Some earlier reviewers (Illum, 1991; Wearley, 1991) expected that transnasal peptide delivery, supported by absorption enhancers, will provide a convenient, efficient means for the administration of protein and peptide therapeutics. More recent surveyors took less optimistic stance, however (Harris, 1993). Rapid metabolism and nonlinear pharmacokinetics of nasally delivered peptides (Wearley, 1991) are partly responsible for this. The other reasons are the anatomical and temporal barriers presented by the nasal mucosa (Sarkar, 1992), and especially the intolerable side effects of most, if not all, methods currently in use for nasal delivery. This holds also true for efforts to deliver compounds with the aim to generate a protective immune response transnasally, which would represent a more natural way of antigen presentation than encountered by conventional injection. The adverse side effects observed with transnasal immunisation experiments are mainly due to the presence of immunoadjuvants (such as Cholera toxin (CT) or its fragment B, heat labile protein from E. coli, keyhole limpet hemocyanin, or other substances with ADP-rybosilating activity, for example), and/or molecules with a permeation enhancing activity, in addition to the antigen in the formulation for nasal delivery. While the former may be toxic, the latter are irritating to the immunised subject. Selectivity of immune response, moreover, cannot be achieved with unspecific stimulatory agents. Moreover, there is substantial variability in the resulting immune response after nasal antigen administration, probably due to the difficulty of depositing the immunogen on the sites in the nasal cavity with the lowest transbarrier transport resistance.

The human nasal cavities with a total volume of 15 mL and a total surface area of 150 $cm^2$—which amounts to more than 1 $m^2$ if one allows for the surface corrugations—are covered by mucus and a mucosa 2 mm to 4 mm thick. Most of the cavity surface is lined by a respiratory epithelium, comprised of columnar cells, goblet cells, and ciliary cuboidal cells. The resulting permeability barrier is related to that of the oral cavity, with which it communicates and which is covered by a keratinised barrier tissue. In either case, the cells in the barrier are tightly packed and often sealed with the specialised intercellular lipid arrangements. Moreover, in either case, the permeability barrier is lowered by the topical use of substances which compromise the quality and packing of such lipidic seals and/or which increase the probability for molecular partitioning into the barrier. Deviant from the situation encountered in the mouth, from the nose foreign substances are cleared into the nasopharynx by the cilia, with an average speed of 5 mm/min. An exception is the upper region of nasal cavity, which contains no cilia but is covered by a pseudo-stratified olfactory neuroepithelium. The nasal subepithelum contains a dense vascular network and the venous blood from the nose passes directly into the systemic circulation.

Nasal route of delivery has been relatively unsuccessful to date when used for high molecular weight substances. Use of permeation enhancers did not improve the situation sufficiently, largely due to the fact that such substances are generally poorly tolerated and of limited usefulness. The pharmacodynamics resulting from nasal drug delivery is also highly variable. Major reasons for this are the inconsistency in the site of deposition or in the delivery details, as well as changes in the mucous secretion and mucociliary clearance; the latter are compounded especially by the presence of allergy, hay fever, and the common cold in treated subjects (Harris, 1993). Protein degradation in mucosa is important as well (Sarkar, 1992). Despite this, numerous studies were done with buserelin, vasopressin, cholecystokinin, calcitonin, growth hormone and related substances (e.g. GHRH), erythropoietin, G-CSF, interferon, insulin, gonadotropin hormone releasing hormones (GnRH), and vasopressin analogues, the results of which are reviewed briefly in the following.

Systemic Delivery of Large Drugs Through the Nose

Hexarelin (GH analogue; MW≈800). The GH response to the intranasal hexarelin administration (about 18 μg/kg) was not significantly higher than that induced by an injection of 1 μg GHRH/kg (Ghigo et al., 1996). On the other hand, the former kind of treatment did not significantly modify IGF-I but increased IGFBP-3 levels. Both IGF-I and IGFBP-3 levels were slightly but significantly increased by oral treatment with the drug as well (Ghigo et al., 1996).

Intranasal treatment with octreotide nasal powder, a somatostatin analogue (up to 2 mg TID, corresponding to a mean GH value below 5 μg/L during 8 daytime hours), was well tolerated, with only mild side effects and no significant changes in the nasal mucosa. An improvement of the clinical picture was registered in all patients after a few days of octreotide nasal powder administration. Positive correlation was found between GH and IGF-I, GH and IGFBP-3, IGF-I and IGFBP-3, insulin and IGFBP-3 and insulin and IGF-I during chronic (3-6 months) treatment (Invitti et al., 1996).

Cholecystokinin (MW≈1050). The carboxy terminal octapeptide of cholecystokinin (CCK-8) has similar functions as native cholecystokinin (CCK), but lacks receptor selectivity and metabolic stability. Mediation of satiety via the A-receptor subtype can be used for management of obesity. This was also shown after intranasal administration of Hpa(SO3H)-Nle-Gly-Trp-Nle-MeAsp-Phe-NH2, the result of moving the N-methyl group from Phe to Asp, which inhibited feeding in beagle dogs (Pierson et al., 1997).

After intranasal (10 µg) and intravenous (0.25 µg and 2.5 µg) administration of an octapeptide derivative of cholecystokinin, the substance CCK-8 was shown to affect the auditory event related potential (AERP) in 20 healthy subjects. The effect was stronger in women than in men (Pietrowsky et al., 1996). Plasma CCK-8 concentrations after intranasal administration of 10 µg CCK-8 were comparable to those of 0.25 µg CCK-8 given i.v., but were substantially lower than those elicited by 2.5 µg CCK-8 (Pietrowsky et al., 1996).

Vasopressin (MW=1054). Vasopressin DGAVP (2 mg) was administered intranasally and orally to healthy subjects for 1 week. Peak levels were always observed at 15 min. The mean absorption and elimination half-life (around 8 min and 35-38 thin, respectively) were similar for the two tested routes of administration, but the latter only had 0.7% relative bioavailability (Westenberg et al., 1994).

In a double-blind, crossover study, subjects received on three different occasions 20 IU of (arginine)vasopressin (AVP) intranasally (IN), or 1.5 IU of AVP and saline solution i.v. Evoked potentials (ERPs) were recorded during the subject's performance on a auditory attention task. Plasma concentrations of vasopressin during task performance were enhanced after AVP, with the increase after i.v. administration of AVP exceeding 2000-fold that after AVP i.v. Intranasal administration of AVP substantially increased the P3 component of the ERP in contrast to the injection (Pietrowsky et al., 1996).

Acute (2 mg) and chronic, 2 weeks treatment (1 mg/day) with nasal DGAVP revealed an improved short-term memory for abstract words in males but not in females, with no positive effect on learning concrete words. Chronic, but not acute, treatment with DGAVP reduced the reaction time for scanning of digits in a memory comparison task (Sternberg paradigm) in both sexes (Bruins et al., 1995). In a different human study, arginine-vasopressin (AVP: 3×10 IU) enhanced memory performance after nasal administration. The late positive complex (LPC) elicited by oddball stimuli was not affected whereas the structural encoding task revealed an effect of the drug. In both studies, AVP intake resulted in a marked change of the scalp distribution of the P3 component, which is a prominent part of the LPC. Vasopressin was thus concluded to influence the central nervous processing of the emotional content of stimuli (Naumann et al., 1991).

Subchronic treatment with vasopressin (40 IU/day) was shown to enhance nocturnal slow-wave sleep in 2 elderly subjects (Perras et al., 1996). However, the intranasal administration of vasopressin (DDAVP: 30 or 60 micrograms) had no general effect on pain perception in humans, but some other effects were observed (Pohl et al., 1996).

Buserelin (MW=1239). Treatment of 40 women with endometriosis and 10 women with uterine leiomyoma by using GnRH agonist buserelin (200 µg, 3× daily, 6 months, intranasally) reduced AFS mean pelvic score from 24 to 7 and the size of the fibroids decreased by 69% (Biberoglu et al., 1991).

Calcitonin (MW=3432). Ichikawa et al. (1994) concluded that nasal (5, 10, 20 and 40 U/rat) and subcutaneous (5, 10 and 20 U/kg) administration of Salmon calcitonin on alternate days for 3 weeks, starting a week after ovarectomy, prevented the osteopenic changes, the invasive method being approximately 2-times more effective.

In a double-blind trial, the effect of intranasal administration of Salmon calcitonin on biochemical parameters of bone turnover in 32 patients immobilised for a prolapsed intervertebral disk was investigated (van der Wiel et al., 1993). Calcitonin in a dose of two times 200 IU/day inhibited by 40% the increase in the fasting 2 h urinary hydroxyproline/creatinine ratio (OHPr/Cr) and lowered by 80% the increase in calcium/creatinine ratio (Ca/Cr). The decrease in serum 1,25-dihydroxyvitamin D after 10 days of immobilization was significantly less in the calcitonin-treated group than in the placebo group (14 versus 29%, respectively; $P<0.05$). However, intranasal calcitonin, which was well tolerated, did not influence the pain scores as measured with a visual analog scale (van der Wiel et al., 1993).

Growth hormone (GH) releasing factor/s (MW=5040). The current mode of growth hormone replacement therapy is daily subcutaneous (s.c.) injections given in the evening. This schedule is unable to mimic the endogenous pulsatile pattern of GH secretion, which might be of importance for the induction of growth and other GH actions (Laursen et al., 1996).

To simulate endogenous production of growth hormone the protein was administered on three occasions intranasally in doses of 0.05, 0.10 and 0.20 IU/kg, using didecanoyl-L-α-phosphatidylcholine as an enhancer (Laursen et al., 1996). On the other two occasions the patients received an s.c. injection (0.10 IU/kg) and an i.v. injection (0.015 IU/kg) of GH, respectively. The nasal doses and the s.c. injection were given in random order in a crossover design. Intravenous administration produced a short-lived serum GH peak value of 128 µg/L. Peak levels were around 14 µg/L after s.c. injection (50% bioavailability) and between 3 µg/L and 8 µg/L, respectively, after the three nasal doses (bioavailability between 4% and 9%). Serum insulin-like growth factor I (IGF-I) levels increased significantly after s.c. administration only. However, the data revealed that a closer imitation of the physiological GH pulses was achieved via the nose. Despite this the authors of the study concluded that GH administration is of limited importance for the induction of a metabolic response to GH (Laursen et al., 1996).

GHRP-2 is one of the most potent members of the GHRP family, which exerts its biological activity after oral, intranasal and i.v. administration. For example, the children who had a robust response to the injected GH-releasing factors also received intranasal GHRP-2, with significant, but not quantitated, response over a dose range of 5-20 µg/kg per dose (Pihoker et al., 1995).

Insulin (MW=5808). The problem of low bioavailability of insulin solutions given through the nasal mucosa was improved by using absorption enhancers or bioadhesive microspheres (Gizurarson & Bechgaard, 1991; Illum & Davis, 1992). Bioavailability greater than 10% was measured but to date no corresponding formulation has found its way into the late clinical trials. The chief reason for this appears to be the severe damage to nasal mucosa caused by the commonly used permeation enhancers.

For example, following the administration of powder formulations comprising insulin and the permeation enhancer sodium tauro-24,25-dihydrofusidate (STDHF), the hypoglycaemic response and the serum insulin levels in sheep increased with STDHF/insulin molar ratio in the range 0 to 16.8 (Lee et al., 1991). The reason for this is increased mucosal permeability as well as reduced insulin aggregate size. The bioavailability ranges from 2.9% to 37.8% for the powder, and was reported to be 15.7% and 37.4%, respectively for the drops or spray containing STDHF/insulin=8.4/1 mixture, and roughly proportionally to the enhancer concentration (Lee et al., 1991). To achieve a high bioavailability major changes in nasal mucosa had to be tolerated, however.

In humans, the 200 U insulin/mL formulation containing a blend of enhancers (didecanoyl-phosphatidylcholine (2 w-%), glycerol (1.6 w-%), 0.4 w-% fractionated coconut oil) and 0.2 w-% cholesterol resulted in appr. 8% bioavailability, the highest values having been measured for the high dose (2×3 sprays of 50 µL each), which also was most irritant (Drejer et al., 1991).

Cyclodextrins dissociate insulin hexamers into smaller aggregates, in dependence on structure and concentration. Hexamer dissociation was therefore speculated to be the reason for higher nasal absorption of the polypeptide (Shao et al., 1992). The relative effectiveness of various cyclodextrins for this purpose was reported to decrease from dimethyl-β-cyclodextrin (DM-β-CD)>α-cyclodextrin (α-CD)>β-cyclodextrin (β-CD), hydroxypropyl-β-cyclodextrin (HP-β-CD) >γ-cyclodextrin (gamma-CD). A direct relationship between absorption promotion and nasal membrane protein and lipid release was invoked to explain such sequence (Shao et al., 1992).

It is less clear why cationic chitosan enhances the absorption of insulin across the nasal mucosa of rat and sheep in a concentration dependent fashion, with optimum concentrations higher than 0.2% and 0.5% in rats and sheep, respectively, but overall efficiency of this procedure is only around 10% (Illum et al., 1994). Using didecanoyl-L-α-phosphatidylcholine as an enhancer results in 4% to 9% of nasal insulin bioavailability (Laursen et al., 1996).

G-CSF (MW=19600). The relative bioavailability of rhG-CSF administered nasally in the rat was approximately 2%, compared to an s.c. injection, as evaluated from the immunologically active rhG-CSF concentration in rat plasma and the area under the curve (AUC) at t=8 h. Leukocyte stimulation counts suggested 5-10% availability at t=48 h. Relative bioavailability and pharmacological availability were increased 23 times and 3 times, respectively, by polyoxyethylene 9-lauryl ether (Laureth-9), but no increase in availability occurred with sodium glycocholate (Machida et al., 1993).

Absorption of dissolved recombinant human granulocyte colony-stimulating factors (rhG-CSF at pH 4)) through the nose of rabbits was investigated with dimethyl-β-cyclodextrin added or without such excipient, which acts as barrier permeation enhancer. The proteins were absorbed and the total leukocyte numbers in peripheral blood increased in either case, but excipients improved the absorption of rhG-CSF appreciably (Watanabe et al., 1993). A subsequent pharmacokinetic and pharmacodynamic study (Watanabe et al., 1995) revealed that protein is absorbed through the nasal cavity from a solution, especially in the presence of alpha-cyclodextrin (α-CyD), which can act as carrier in the membrane. Good correlation was found between the logarithm of the area under the serum G-CSF concentration-time curve (AUC) and the area under the increased total blood leukocyte count-time curve (Watanabe et al., 1995).

Interferon (MW=23000). Treatment of experimental rhinovirus colds in 38 adults by intranasal administration of recombinant interferon beta serine (MW=18500) had no effect on illness rate or severity, but did decrease the frequency of virus shedding by the factor of 2 (on day 4) to 3 (on day 6). The course of middle-ear dysfunction associated with experimental colds was also positively affected by the drug (Sperber et al., 1992).

Erythropoietin (MW=30400). The pharmacological availability of rh-EPO after intranasal administration without enhancers was compared to that of intravenous injections. The pharmacological activity was enhanced in low pH and hypotonic mannitol solution, which both compromise the barrier quality. This resulted in relative bioavailability of nasally applied drug between 7% and 4%, when estimated by different reticulocyte counting methods. (Shimoda et al., 1995).

Labelled dextrane (MW=4100, 9000, 17500), applied nasally at the dose of 6.5 mg, was seen to pass mucosa in the presence of glycocholate (3 mg) and found in the blood in concentration range between 6 ng/mL and 21 ng/mL, which corresponds to app. 0.05%, 0.02%, and 0.01% for the three molecular sizes, respectively (Maitani et al., 1989).

In summary, the combined teachings of the prior art demonstrated that the likelihood of large molecules to pass nasal mucosa decreases strongly with increasing molecular weight. To date, the size of molecules administered successfully through the nose is typically <1300 Da, and always below 3500 Da. Significant transport is achieved only with supporting permeation promotors and is, in a certain concentration range at least, proportional to the enhancer concentration. Enhancer concentration in the percentile range can ensure up to 30% drug (or label) bioavailability but more often values below 10% and typically of a few percent are obtained. High transfer efficiency is accompanied with strong local tissue damage. This causes unpleasant acute side effects and may, first, abrogate the nasal permeability barrier and, upon repeated use, provoke extensive keratinisation of the epithelium that finally reduces transnasal transport efficiency.

The success of transnasal transport is believed to rely on the loosening of ciliated-goblet, goblet-goblet, or ciliated-ciliated cell contacts, which also opens passages for the motion of water (McMartin et al., 1987). Procedures or substances which support the process either osmotically (as in the case of polysaccharide addition), physico/chemically (as in the case of surfactant addition) or biologically (as in the case of molecules which affect the cell biochemistry, including many drugs, cell adhesion or trans- and epicellular transport), can therefore improve drug delivery across the nasal mucosa. Translocation through the cells is possible, but probably rare, except, maybe, in the cases of some viral infections or applications. Materials, such as polymers of polyelectrolytes, which prolong the retention time of and increase the proximity between the molecules to be transported and cellular membranes, are useful for the purpose as well. The limit to this latter effect is set by ciliary motion, which tends to clear mucosal surface approximately every 30 min and transports the superficial material into the throat, and thus towards the gastrointestinal tract. Transport mediated by certain particles was contended to rely on this effect.

Particle Delivery Through the Nose

Inhaled fine particles (Kanto loam dust, fly ash, carbon black, diesel exhaust particles (DEP), and aluminium hydroxide (alum)) appear to act as adjuvants, and accelerate the production of IgE antibody against pollen in female BDF1 mice; however, the nature of the particles, their capacity to adsorb antigens, and/or their size seem to play only minor role in the process (Maejima et al., 1997).

Hollow spheres, according to Ting et al. (1992), are unsuitable for nasal delivery, owing to their rapid clearance and variable deposition pattern. Polyvinyl alcohol microparticles in the form of collapsed, solid spheres with the desired size for nasal deposition (10-200 µm) were therefore produced by spray-drying and spray-desolvation (Ting et al., 1992).

The above observation notwithstanding, several kinds of particulate suspensions were used in the nose, typically to elicit antibodies against the particle-associated antigens.

This includes so-called proteosomes comprising gp160 (Lowell et al., 1997) or influenza virus proteins. Another example are particles made from polymerised carbohydrates coated with a lipid (bi)layer.

It is important to realise, however, that in any nasal uptake study one should consider and allow for secondary redistribution. For example, the biodistribution of radioactivity from the purified major *Parietaria judaica* allergen after sublingual, oral, and intranasal administration in healthy human volunteers is similar. This is indicative of test material swallowing and absorption in the gastrointestinal tract (Bagnasco et al., 1997). In the intranasal case, transport to the pharynx by mucociliary clearance plays an important role as well, but a relevant fraction of the tracer is retained on the nasal mucosa for up to 48 hours after administration (Bagnasco et al., 1997).

Oral Spill-Over and the Danger of False Positive Results

Proteins are absorbed in the gastrointestinal tract, albeit in small quantities. For example, ovalbumin (OVA) is absorbed in the stomach as well as from the GI tract into the blood and lymph circulation at levels of 0.007-0.008% and 0.0007-0.002% of applied dose; a higher dose in the latter case leads to relatively higher absorption (Tsume et al., 1996). Stomach absorption supplies nearly exclusively the blood, suggesting different mechanisms and/or routes of absorption between the stomach and the small intestine. OVA association with liposomes can improve the uptake about 2 to 3-fold, possibly owing to slower enzymatic degradation of OVA.

Often, the result of nasal and oral immunisation are very similar, suggesting that part of the effect of the former may be due to the spill over of the antigen into gastro-intestinal tract. Data obtained with human adenovirus type 5, used as a vector for heterologous DNA sequences, illustrate this (Flanagan et al., 1997).

Transnasal Delivery into the Central Nervous Tissue (CNS)

The access of substances to the brain is of paramount importance for the treatment of psychiatric and neurologic diseases. Transnasal route of delivery into the CNS was therefore tested for a few selected bioactive molecules.

To date, drug delivery into the CNS tissue by nasal administration has received little attention (Pesechnik & Price, 1996). Wheat-germ agglutinin coupled to horseradish peroxidase was demonstrated to be taken up by the cells of olfactory nerve, resulting in concentration in the olfactory bulb around 0.1% of applied concentration; the underlying principle is probably receptor-mediated endocytosis of WGA and subsequent trans-synaptic, retrograde transfer towards the brain. A similar mechanism is also possible in the case of viral infections in the nose.

For example, an intranasal instillation of vesicular stomatitis virus (VSV), a negative-sense RNA virus, may result in a lethal infection of murine and rat brain (Huneycutt et al, 1994). Within 12 h following intranasal inoculation of VSV, this antigen can be detected in the olfactory nerve layer of the ipsilateral olfactory bulb. Within 3-4 days post-inoculation (p.i.), VSV had disseminated into the glomeruli of the olfactory bulb as well as the anterior olfactory nuclei, ipsilateral to the VSV instillation. Within the glomeruli, VSV antigen is more prevalent in the granule cells than in the mitral cells. Correspondingly, the lateral olfactory tract, where axons of mitral cells course, remain VSV negative throughout 7 days p.i. By 7 days p.i., viral proteins are detected in several additional regions extending to the brainstem. The pattern of VSV immunoreactivity supports the picture of initial infection of the olfactory bulb glomeruli, with subsequent spreads via both ventricular surfaces and retrograde transport within axons of neuromodulatory transmitter systems enervating the olfactory bulb (Huneycutt et al, 1994).

Draghia et al. (1995) have demonstrated that it is possible to transfer the *Escherichia coli* lacZ gene in vivo into the central nervous system structures of rats after nasal instillation of replication-defective adenoviral vector AdRSV beta gal. Mitral cells from the olfactory bulb, neurons from the anterior olfactory nucleus, locus coeruleus and area postrema expressed beta-galactosidase for at least 12 days (Draghia et al., 1995). Parainfluenza type 1 vaccine virus also directly accesses the central nervous system by infecting olfactory neurons (Mori et al., 1996).

However, it would be highly desirable to have a convenient and reliable transnasal transport system for the compounds that are capable of and intended to generate a protective immune response without simultaneously generating a variety of adverse side effects. Common types of non-invasive applications, including oral immunisation, often do not elicit the desired immune response. Many injectable vaccines also do not provide optimum antibody isotype pattern, mainly due to the unnatural route of antigen entry into the body. Transnasal immunisation remains problematic owing to the large size of typical immunogen which is subject to similar restrictions as the transport of pharmaceutically active compounds across the nasal mucosa.

In conclusion, although the prior art has tested various approaches to transnasal delivery it has hitherto failed to provide a convincing principle for convenient and well tolerated transfer of compounds, such as pharmaceutically active substances, immunogens/antigens or allergens, through the nasal barrier, in particular if said compounds are large. The solution to said technical problem, i.e. the provision of a suitable system, is provided by the embodiments characterised in the claims.

Accordingly, the present invention relates to use of a penetrant, suspended or dispersed in a solvent, in the form of a minute fluid droplet surrounded by a membrane-like coating of one or several layers of at least two different substances or two different forms of a substance with the tendency to aggregate, said substances or forms of a substance differing by at least the factor of 10 in solubility in a preferably aqueous liquid medium, such that the average diameter of homo-aggregates of the more soluble substance or form of the substance or the average diameter of the hetero-aggregates consisting of both said substances or forms of said substance is smaller than the average diameter of homo-aggregates of the less soluble substance or form of the substance and/or wherein the more soluble component tends to solubilise the penetrating droplet and wherein the content of such component amounts to up to 99 mol-% of the concentration required to solubilise the droplet or else corresponds to up to 99 mol-% of the saturating concentration in the un-solubilised droplet, whichever is higher, and/or wherein the elastic deformation energy of the droplet surrounding the membrane-like coating is at least 5× lower, more preferably is at least 10× lower and ideally is more than 10× lower than that of the red blood cells or of the phospholipid bilayers with fluid aliphatic chains, such droplets then acting as carriers, for the transnasal administration of pharmaceutically active compounds, antigens, allergens, mixture of antigens and/or mixture of allergens.

These compounds, antigens or allergens do not cross the nasal mucosa in a practically meaningful quantity on their own without causing inacceptable side effects.

As regards the above recited values of up to 99%, it is to be noted that values below 50% of the former relative concentration are particularly useful, with values below 40 rel-% or even around and below 30 rel-% being even more advantageous, whereas in the case of droplets which cannot be solubilised by the more soluble component relative concentrations which exceed the above mentioned relative concentrations by the factor of up to 2 are most preferred.

Formulations including the above-referenced penetrants are described in detail in DE 41 07 152, PCT/EP91/01596 (published as WO/1992/003122 and equivalent to U.S. Pat. No. 6,165,500 A), PCT/EP96/04526 published as WO/1998/17255 and equivalent to U.S. Publication No. 2002/048596). and DE 44 47 287, which are incorporated herewith by reference. Relevant information useful for penetrant manufacturing and loading with various macromolecular actives, which are too big to permeate through the barrier, is given in patent application PCT/EP98/06750 (published as WO 00/24377 and equivalent to U.S. Publication No. 2008/279815), also incorporated herewith by reference.

More general information on lipid suspensions can be found in the handbook dealing with 'Liposomes' (Gregoriadis, G., ed., CRC Press, Boca Raton, Fla., Vols 1-3, 1987), in the book 'Liposomes as drug carriers' (Gregoriadis, G., ed., John Wiley & Sons, New York, 1988), or in the laboratory manual 'Liposomes. A Practical Approach' (New, R., Oxford-Press, 1989). The properties of phospholipids, which can be used conveniently to prepare bio-compatible immunopenetrants, are reviewed in 'Phospholipids Handbook' (Cevc, G., ed., Dekker, New York, 1995).

The manufacturing temperature for said penetrants is normally chosen in the 0° C. to 95° C. range. Preferably, one works in the temperature range 10-70° C., most frequently at temperatures between 15° C. and 45° C., under all circumstances below the temperature at which any important formulation ingredient would undergo an irreversible change in the composition or physical state. These temperatures can be determined by the person skilled in the art using his common general knowledge and the teachings of the various documents cited in this specification. (For reference: the skin temperature is normally around 32° C.) Other temperature ranges are possible, most notably for the systems containing freezable or non-volatile components, cryo- or heat-stabilised formulations, etc.

If required to maintain the integrity and the desired properties of individual system components, carrier formulations can be stored in the cold (e.g. at 4° C.), with or without associated active agents. It is also possible, and sometimes sensible, to manufacture and store the preparation under an inert atmosphere, e.g. under nitrogen. The shelf-life of carrier formulation, moreover, can be extended by using substances with a small number of double bonds, that is, by a low degree of unsaturation, by choosing peroxide-arm ingredients, by including antioxidants, chelators, and other stabilising agents, or by preparing the agent loaded penetrants ad hoc or in situ, e.g. from a freeze dried or dry mixture.

The term "two forms of a substance" in connection with this invention means two ionization states or salt forms of the same substance, or two different complexes of such substance.

"Non-invasive administration" or "non-invasive delivery" in this specification denotes application on or transport through the nasal mucosa.

"Nasal administration", in the context of this document, refers to applications of test material, whether by direct intranasal intubation, spontaneous sniff of a drop of the test fluid, or an inhalation of the sprayed test-fluid into the nose, independent of precise site of impact or deposition.

The term "penetration" in this application describes non-diffusive motion of large entities across a barrier. This process is believed to involve penetrant adaptation to the otherwise confining pores in the barrier, perhaps in association with a transient, selective, and reversible decrease in the barrier resistance.

The term "permeation" refers to a diffusion across the semipermeable barrier and is typically driven by the permeant concentration gradient across the barrier.

A penetrant, consequently, is an entity comprising a single molecule or an arrangement of molecules too big to permeate through a barrier but capable to cross the barrier owing to the penetrants adaptability to the shape and/or diameter of the otherwise confining passages (pores) of a barrier. This adaptability is seen from the fact, for example, that penetrants more than twice bigger than the pore diameter will cross the bilayer without being fragmented down to the pore size. A permeant, on the other hand, is an entity that can permeate through the semi-permeable barrier, such as the skin. A penetrant in an external field experiences a driving force proportional to the nominal penetrant size and to the applied field, which may occur naturally. Such a force, which on the intact, non-occluded skin is believed to originate from the water concentration gradient across the stratum corneum, can result in a penetrant motion through the barrier, including the skin, if the force is strong enough either to deform the penetrant or else to widen the passages in the barrier sufficiently to elude the problem of size exclusion, or both.

A permeant, on the other hand, is a molecule diffusing, or at least capable of diffusion, across the semi-permeable barrier.

The above-referenced penetrant is typically an ultra-adaptable entity comprising several components. Said penetrant, in the widest sense of the word, is a supra-macromolecular body that can pass spontaneously through the permeability barrier with pores much smaller than the penetrant diameter, and thus transport material from the application to the destination site on either side of the barrier. In order to meet this goal, the penetrant must adjust its properties, most notably its deformability, to the shape and size of the pores in a barrier. This typically occurs under the influence of a strong driving force or a pressure acting on all molecules in the penetrant. Gradients which do not depend on the penetrant concentration, such as hydration or external electric potential difference across the barrier, were shown to serve this purpose.

Lipid aggregates in (quasi)metastable state, and of the nature described above in connection with the invention, most often behave as highly adaptable penetrants, especially when they have the form of a tiny droplet surrounded by one or a few membranes (bilayers) (Cevc et al., 1997; Cevc et al., 1998). Owing to membrane metastability, unusually high local bilayer curvature can develop at the sites of transient, local membrane destabilisation without compromising the overall aggregate integrity. From the composition point of view, such ultra-adaptable and self-regulating vesicles typically consist of a suitably chosen lipid mixture. In order to change conventional lipid vesicles, liposomes, into the optimised vesicles (Transfersomes) one can add, for example, suitable edge-activators into the aggregate membrane (Cevc et al., 1998). Alternatively, molecules which change the system deformability after complexation with or binding to the basic aggregate ingredient can be used. Often, but not necessarily, the activators belong to the class of surfactants below the saturation or solubilization concentration, which in the latter case gives rise to mixed micelles formation. This is important as solubilised lipids, in the form of mixed lipid micelles, can cross the pores sufficiently wider than the micelle diameter but are incapable of enforcing channel opening in the biological tissues, which can be widened and trespassed by the mixed lipid vesicles, however. The postulated reason for this—to which the applicant does not wish to be bound—is the much greater aggregation number, of the latter kind of aggregate which translates into the greater sensitivity to external, transport-driving gradients, such as the water activity gradient, and which is then capable of paying the energetic price for the pore or channel opening in the barrier.

The present invention is, in view of the prior art, particularly surprising since ultradeformable lipid vesicles would seem unsuitable for the purpose of transnasal delivery taken that they were reported to date to cross barriers, such as skin, only under non-occlusive conditions, that is, in the presence of a strong trans-barrier water concentration gradient (Cevc et al. 1995; Paul and Cevc, 1995), which is believed not to exist in the strongly hydrated nasal mucosa.

It was unexpectedly found that macromolecules in association with highly adaptable penetrants, typically in the form of mixed lipid vesicles, are transported across nasal mucosa despite the high water content in this mucosa and in the exhaled air saturated with humidity. Concluding from the fact that several successfully tested formulations of such carriers caused no irritation in the nose it is inferred that the aforementioned transport does not rely on damaging the barrier, such damage being the reason for more conventional transport of macromolecules from a solution across the nasal mucosa. Rather than this, it is reasoned (wherein the applicant does not wish to be bound by theory) that said transport relies on the carrier penetration through the barrier, which should not occur in a very humid surrounding.

It is furthermore taught in accordance with the invention that increasing the concentration of the surface active molecules, which can act as permeation enhancers, decreases the efficiency of corresponding protein transport across the nasal mucosa, at least when the solubilisation point of the carriers has been reached. This finding is unexpected in view of the fact that the art teaches that the bioavailability of nasally administered macromolecules typically gets higher with increasing permeation enhancer concentration.

A third unexpected finding is that carrier-mediated delivery of macromolecules across the nasal mucosa can mediate a relatively efficient transport of large molecules into the central nervous system (CNS). The influx is seen relatively soon after the drug administration into the nasal cavity when the large molecules are associated with the carriers. This could be due to the transport of carrier-associated drugs across the nasal mucosa and subsequent uptake of drug-laden carriers into the olfactory nerve, through which the drug could be carried towards and into the CNS by the retrograde transport; such transport has already been postulated and was tested with individual molecules (Pasechnik-V; Price-J. Exp. Opin. Invest. Drugs; 5: 1255-1276); the approach was not used, to the best of the applicant's knowledge, in combination with particulates to date. An alternative explanation would involve the carrier-mediated macromolecular delivery into the peri-nasal lymphatic system, which has been reported to communicate with the central nervous system (Kida-S; Pantazis-A; Weller-R O. Neuropathol. Appl. Neurobiol. 1993; 19: 480-448).

A fourth surprising result achieved in accordance with the present invention is that the referenced penetrants allow a successful and preferably protective transnasal immunisation with large immunogens. The use of highly adaptable antigen- or immunogen-carriers for the purposes of immunotherapy is expected to or has been shown in accordance with the present invention to provide all the benefits of more conventional nasal vaccinations in addition to the safety and robustness of administration. Improved safety would reflect the choice of the non-toxic and non-irritating carrier ingredients. Better reproducibility could result from the greater ability of the specially designed carriers, compared to that of the antigens or immunoadjuvants used alone to overcome the nose barrier. Taken the expectation that different carrier populations loaded with the individual antigens could be combined into a final multi-valent vaccine formulation the capability of invented technology to meet the trend in immunotherapy is given.

It stands to reason that non-toxic and "gentle" formulations containing merely bio-compatible or natural, body-like ingredients, which protect the body faster and/or better than the corresponding antigen injections, would be preferred to the latter and would have a substantial commercial value.

In accordance with the present invention it is recommended to choose the penetrant characteristics, especially the deformability, concentration, or composition of the mixed lipid aggregates, so as to control the rate or the efficiency of penetrant-mediated transport.

In the process of optimisation of the formulation and/or administration it may be convenient to determine the flux of drug or agent loaded penetrants through the pores in a well-defined barrier as a function of suitable driving force or pressure, which act across the barrier, and then to describe the data by a convenient characteristic curve which, in turn, is employed to optimise the formulation or application further.

The pharmaceutically acceptable form of the agent may be given in a variety of final formulations, optionally, and depending on the purpose of the administration, in combination with diverse secondary agents. Such agents will be explained in more detail later in the text and may be, for example, bacterial compounds or other immunomodulations.

Furthermore, the present invention relates to the use of a penetrant, suspended or dispersed in a solvent, in the form of a minute fluid droplet surrounded by a membrane-like coating of one or several layers of at least two different substances or two different forms of a substance with the tendency to aggregate, said substances or forms of a substance differing by at least the factor of 10 in solubility in a preferably aqueous, liquid medium, such that the average diameter of homo-aggregates of the more soluble substance or form of the substance or the average diameter of the hetero-aggregates consisting of both said substances or forms of said substance is smaller than the average diameter of homo-aggregates of the less soluble substance or form of the substance and/or wherein the more soluble component tends to solubilise the penetrating droplet and wherein the content of such component amounts to up to 99 mol-% of the concentration required to solubilise the droplet or else corresponds to up to 99 mol-% of the saturating concentration in the un-solubilised droplet, whichever is higher, and/or wherein the elastic deformation energy of the droplet surrounding the membrane-like coating is at least 5× lower, more preferably is at least 10× lower and ideally is more than 10× lower than that of the red blood cells or of the phospholipid bilayers with fluid aliphatic chains as a carrier for the preparation of a pharmaceutical, preferably a vaccine composition for transnasal administration. It is preferred that these molecules used on their own do not cross the nasal mucosa in practically useful quantity without causing inacceptable side effects.

The carrier is combined with the pharmaceutically active ingredient prior to the administration, e.g. when formulating said pharmaceutical composition. As regards the further explanations, description of advantages etc., of this and the following embodiments, reference is made to the respective description in connection with the first embodiment described herein above. It is further to be understood in accordance with the present invention that more than one type of antigen, allergen or pharmaceutically active ingredient or combinations thereof may be formulated into said pharmaceutical composition.

Additionally, the present invention relates to the use of a penetrant, suspended or dispersed in a solvent, in the form of a minute fluid droplet surrounded by a membrane-like coating of one or several layers of at least two different substances or two different forms of a substance with the tendency to aggregate, said substances or forms of a substance differing by at least the factor of 10 in solubility in a preferably aqueous, liquid medium, such that the average diameter of homo-aggregates of the more soluble substance or form of the substance or the average diameter of the hetero-aggregates consisting of both said substances or forms of said substance is smaller than the average diameter of homo-aggregates of the less soluble substance or form of the substance and/or wherein the more soluble component tends to solubilise the penetrating droplet and wherein the content of such component amounts to up to 99 mol-% of the concentration required to solubilise the droplet or else corresponds to up to 99 mol-% of the saturating concentration in the un-solubilised droplet, whichever is higher, and/or wherein the elastic deformation energy of the droplet surrounding membrane-like coating is at least 5× lower, more preferably is at least 10× lower and ideally is more than 10× lower than that of the red blood cells or of the phospholipid bilayers with fluid aliphatic chains in combination with a pharmaceutically active ingredient or an allergen or an antigen for the preparation of a transnasally administerable pharmaceutical composition for the treatment of infective diseases, endocrine disorders, preferably hypopituitarism, diabetes, hyperthyroidism, thyroiditis, most preferably Hashimoto's thyroiditis, subacute thyroiditis; adrenal disorders, preferably Addison's disease, secondary adrenal insufficiency, Cushing's syndrome; gastrointestinal disorders, preferably Crohn's disease, colitis; hemorrhagic diseases, preferably hemophilia, leukopenia, hypereosinophilic syndrome; musculoskeletal and connective tissue disorders, preferably rheumatoid arthritis, Sjögren's syndrome, Bechet's syndrome, lupus, scleroderma, polymyositis/dermatomyositis, polymyalgia rheumatica and temporal arthritis, polyarteriosis nodosa, Wegener's granulomatosis, mixed connective tissue disorder, ankylosing spondylitis, psoriatic arthritis, osteoarthritis, Paget's disease, sciatica, bursitis, tendonitis or tenosynovitis, epicondylitis, fibromyalgia, eosinophilic faciitis; neurological disorders, preferably pain, singultus, vertigo, seizure disorders, sleep disorders, transient ischemic attacks, spinal cord injury, demyelinating diseases, nerve root disorders, myasthenia gravis; psychiatric disorders, preferably drug dependence, neuroses, mood disorders, schizophrenic disorders, delusional disorders; for oncological purposes and/or for treatment in the field of gynecology, preferably for the treatment of dysmenorrhea, menopause, chronic anovulation, premature ovarian failure, endometriosis, infertility; and/or for treatment in the field of immunology, preferably transplant rejection, hyposensitation, allergen immunotherapy or prophylactic vaccination.

The term "allergen" is used in this invention to describe materials of endogenous or xenogenic, e.g. animal or plant, origin which result in an undesired immune response of the body exposed to such an allergen, often resulting in an acute hypersensitivity reaction. Allergising microbes or parts thereof (e.g. of mite), parts of plants (e.g. pollen) or animal (e.g. hair and skin debris), but also man made and inorganic substances belong to this group. On the other hand, nearly any part of the human body, if incorrectly processed by or exposed to the body's immune system, can result in an auto-immune response and lead to the allergic reaction to such a substance.

In the narrower interpretation, used when so stated, an allergen is a substance, a group, or an arrangement of substances causing immediate hypersensitivity reactions in the body that could be diminished, or even eliminated, by an immunotherapy, whether done non-invasively through the nasal mucosa or not.

An "antigen" is a part of a pathogen or an allergen in its natural form or after fragmentation or derivatisation. More generally, the word antigen denotes a macromolecule or a fragment thereof, any haptenic moiety (for example, a simple carbohydrate, complex carbohydrate, polysaccharide, deoxyribonucleic acid), in short, any molecule recognized by a body's antibody repertoire and possibly capable of antibody induction when administered in the system. A macromolecular antigen is defined as an antigen that is known to or believed to cross spontaneously the nasal barrier only in quantity too small for the desired practical purpose. Thus, macromolecules are molecules that, on their own, do not cross the nasal mucosa in practically useful quantity without causing inacceptable side effects.

The term "a mixture of antigens" or "a mixture of allergens" means, in accordance with the present invention, the combination of at least two antigens and/or allergens. It is envisaged that also mixtures of antigens and allergens can be used according to the present invention.

Furthermore, the present invention relates to a pharmaceutical composition for transnasal administration comprising a carrier which is a penetrant, suspended or dispersed in a solvent, in the form of a minute fluid droplet surrounded by a membrane-like coating of one or several layers of at least two different substances or two different forms of a substance with the tendency to aggregate, said substances or forms of a substance differing by at least the factor of 10 in solubility in a preferably aqueous, liquid medium, such that the average diameter of homo-aggregates of the more soluble substance or form of the substance or the average diameter of the hetero-aggregates consisting of both said substances or forms of said substance is smaller than the average diameter of homo-aggregates of the less soluble substance or form of the substance and/or wherein the more soluble component tends to solubilise the penetrating droplet and wherein the content of such component amounts to up to 99 mol-% of the concentration required to solubilise the droplet or else corresponds to up to 99 mol-% of the saturating concentration in the un-solubilised droplet, whichever is higher, and/or wherein the elastic deformation energy of the droplet surrounding the membrane-like coating is at least 5× lower, more preferably is at least 10× lower and ideally is more than 10× lower than that of the red blood cells or of the phospholipid bilayers with fluid aliphatic chains and a pharmaceutically active ingredient.

In a preferred embodiment of the use or the pharmaceutical composition of the present invention the pharmaceutically active ingredient is an adrenocorticostaticum, an adrenolyticum, an androgen or antiandrogen, an antiparasiticum, an anabolicum, an anaestheticum or analgesicum, an analepticum, an antiallergicum, antiarrhythmicum, antiarterosceroticum, antiasthmaticum and/or bronchospasmolyticum, an antibioticum, an anti-infective agent, an antidepressivum and/or antipsychoticum, an antidiabeticum, an antidot, an antiemeticum, antiepilepticum, antifibrinolyticum, anticonvulsivum or anticholinergicum, an enzyme, a coenzyme or the corresponding enzyme inhibitor, an antihistaminicum (and combinations thereof) or antihypertonicum, an antihypotonicum, an anticoagulant, antimycoticum, antimyasthenicum, an agent against Morbus Alzheimer or Morbus Parkinson, an agent for ACS therapy, an antiphlogisticum, antipyreticum, antirheumaticum, antisepticum, a respiratory analepticum or a respiratory stimulant, a broncholyticum, cardiotonicum, chemotherapeuticum, a coronary dilatator, a cytostaticum, a diureticum, a ganglium-blocker, a glucocorticoid, an anti-flew agent, a haemostaticum, hypnoticum, an immunoglobuline or its fragment or any other immunologically active substance, such as an immunomodulator, a bioactive carbohydrate (derivative), a contraceptive, an anti-migraine agent, a corticosteroid, a muscle relaxant, a narcoticum, a neurotherapeuticum, a (poly)nucleotide, a neuroleptecum, a neurotransmitter, a (poly)peptide (derivative), an opiate, an opthalmicum, (para)-sympaticomimeticum or (para)sympathicolyticum, a protein(derivative), a psoriasis/neurodermitis drug, a mydriaticum, a psychostimulant, rhinologicum, a sleep-inducing agent, a sedating agent, a spasmolyticum, tuberculostaticum, an urologicum, a vasoconstrictor or vasodilatator, a virustaticum, a wound-healing substance, an alcohol abuse preparation, an anticonvulsant, an antineoplastic, an antirheumatic, an appetite suppressant, a biological response modifier, a blood modifier, a bone metabolism regulator, a cardioprotective agent, a cardiovascular agent, a central nervous system stimulant, an enzyme, an agent for erectile dysfunction therapy, a fertility agent, a gastrointestinal agent, a gout preparation, a hormone, an agent for hypercalcemia management, an agent for hypocalcemia management, an immunosuppressive, a migraine preparation, a motion sickness product, an agent for multiple sclerosis management, a muscle relaxant, a nutritional, an ophthalmic preparation, an osteoporosis preparation, an otic preparation, a parasympatholytic, a parasympathomimetic, a prostaglandin, a psychotherapeutic agent, a respiratory agent, a sedative & hypnotic, a skin & mucous membrane agent, a smoking cessation aid, a sympatholytic, a tremor preparation, a urinary tract agent, a vaginal preparation, a vertigo agent, an inhibitor (antagonist), or any other immunologically active substance (such as an immunomodulator, e.g., bacterial extracts or cell wall components like cholera toxin, heat labile toxin, monophosphoryllipid A, or cytokine inducing agents or hormones like thymosin, thymulin, thymopoietin, or phytoimmunostimulants like extracts from Echinacea root, wild indigo root, white cedar leave tips, or synthetic immunomodulators like quinoline derivatives, synthetic peptides, pyrimidine, lipopeptides, or cytokines or immunosuppressants, and signal transduction inhibitors like cyclosporin A, FK506, FTY720, rapamycin), or a promotor (agonist) of the activity of any of above mentioned agents, or any combination of said active substances. It is preferred that said active ingredient does not itself cross the nasal mucosa in practically meaningful quantity without inacceptable side effects.

In another preferred embodiment of the use or the pharmaceutical composition of the present invention the antigen is derived from a pathogen.

In the context of this invention, the term "pathogen" refers to an entity which through its presence in or on the body leads to or promotes a pathological state which, in principle, is amenable to or could profit from a preventive, curative or adjuvant immunotherapy.

In a most preferred embodiment of the use or the pharmaceutical composition of the invention said pathogen belongs to the class of extracellular bacteria, including pus-forming cocci, such as *Staphylococcus* and *Streptococcus*, gram-negative bacteria, such as *Meningococcus* and *Gonococcus* species, species of *Neisseria*, gram negative bacteria, including enteric organisms such as *E. coli, Salmonella, Shigella, Pseudomonas, Diptheria, Bordetella Pertussis*, and gram-positive bacteria (e.g. *Bacillus pestis*, BCG), particularly anaerobes, such as the *Clostridium* species (e.g. *Clostridium tetani, Clostridium perfringens, Clostridium novyi,*

*Clostridium septicum*), bacteria and viruses, which survive and replicate within host cells, comprising mycobacteria (e.g. *M. tuberculosis*) and *Listeria monocytogenes*, retro- and adenoviruses, including hepatitis virus, (human) immunodeficiency virus, herpex viruses, small-pox (chicken-pox), influenza, measles, mumps and polio viruses, cytomegalovirus, rhinovirus, etc., and fungi prospering inside host cells, parasites including animal parasites, such as protozoa and helminths, and ectoparasites, such as ticks and mites, or *Brucella* species (e.g. *B. melitensis, B. abortus, B. suis, B. canis, B. neotomae, B. ovis*), the causative agent for cholera (e.g. *Vibrio cholerae*), *Haemophilus* species like *H. actinomycentemcomitans, H. pleuropneumoniae*, as well as pathogens triggering paratyphoid, plague, rabies, tetanus and rubella diseases; eukaryotic cells or their parts that cause various neoplasiae, auto-immune diseases and other pathological states of the animal or human body, which do not necessarily result from microbial infections, also belong in this group.

It is most preferred that the antigen, preferably the pathogen, is used in a purified, or even better in a pure form.

Pathogens causing major infective diseases such as hepatitis virus, (human) immunodeficiency virus, herpex viruses, small-pox (chicken-pox), influenza, measles, mumps and polio viruses, cytomegalovirus, rhinovirus, etc., and fungi prospering inside host cells, a parasite including animal parasites, such as protozoa and helminths, and ectoparasites, such as ticks and mites, or *Brucella* species, or the causative agent for cholera, *Haemophilus* species, as well as pathogens triggering paratyphoid, plague, rabies, tetanus and rubella diseases are particularly preferred as are eukaryotic cells or their parts that cause various neoplasiae, auto-immune diseases and other pathological states of the animal or human body, which do not necessarily result from microbial infections.

In another preferred embodiment of the use or the pharmaceutical composition of the invention the allergen is of xenogenic or endogenic origin, derived from a microorganism, an animal or a plant, or belonging to the group of man made and/or irritating inorganic substances, or to such parts or components of the human body which were incorrectly processed by or exposed to the body immune system.

In further preferred embodiment of the use or the pharmaceutical composition of the present invention the allergen belongs to the class of the inhalation allergens, including but not limited to various pollen, spores, bits of animal hair, skin, feather, natural and synthetic textiles, wheat, (house) dust, including mite; furthermore, food and drug allergens; contact allergens; injection, invasion or depot allergens, such as various (gastrointestine-resident) worms, echinococci, trichines, etc., or is a part of implantation material.

In an additional preferred embodiment of the use or the pharmaceutical composition of the present invention said pharmaceutical composition comprises a compound which releases or induces cytokine or anti-cytokine activity or exerts such an activity itself.

The term "cytokine", as used in the present invention, denotes cytokines, such as IL-1, IL-2, IL-3, IL4, IL-5, IL-6, IL-7, IL-8, IL-9, IL-10, IL-11, IL-12, IL-13, IL-14, IL-15, IL-16, IL-17, IL-18, with all subtypes, such as IL-1α and IL-1β, tumour necrosis factor (TNF), transforming growth factor (TGF-β and -α), Type I and II interferons (IFN-α1, IFN-α2, (IFN-ω), IFN-β, IFN-γ), migration inhibitory factor, MIF, c-kit ligand, granulocyte macrophage colony stimulating factor (GM-CSF), monocyte macrophage colony stimulating factor (M-CSF), granulocyte colony stimulating factor (G-CSF), chemokines, etc., as well as all functional derivatives of any of these molecules.

Cytokines that mediate natural immunity particularly well include type I interferons (IFN-α and IFN-β), tumour necrosis factor (TNF), interleukin-1 (IL-1α and IL-1β), interleukin-6 (IL-6) and leukocytes attracting and activating chemokines. Antiproliferative (e.g. with IFN-s), pro-inflammatory (e.g. with TNF, IL-1) or co-stimulatory (e.g. with IL-6) action, amongst other, may be generated by transnasal administration of the pharmaceutical composition described in accordance with the present invention. Cytokines which best mediate lymphocyte activation, growth and differentiation include interleukin 2 (IL-2), interleukin-4 (IL-4) and transforming growth factor (TGF). Such cytokines, consequently, not only can affect target growth but, moreover, influence the activation of, and thus the production of other cytokines by, the cells which finally may play a role in therapeutic or prophylactic action.

Cytokines that mediate the immune-mediated inflammation which heavily relies on the cell-mediated response are interferon-gamma (IFN-γ), lymphotoxin (TNF-β), interleukin-10 (IL-10), interleukin-5 (IL-5), interleukin-12 (IL-12) and, probably, migration inhibition factor. Leukocyte growth and differentiation are most affected by interleukin-3 (IL-3), c-kit ligand, granulocyte-macrophage colony stimulating factor (GM-CSF), macrophage or granulocyte colony stimulating factor (M-CSF or G-CSF) and interleukin-7 (IL-7).

It is preferred to select the compound displaying cytokine activity amongst IL-4, IL-2, TGF, IL-6, TNF, IL-1α and IL-1β, a type I interferon, amongst which IFN-alpha or IFN-13 are most preferred, IL-12, IFN-γ, TNF-β, IL-5 or IL-10.

In another preferred embodiment said compound with anticytokine activity is an anti-cytokine antibody or the corresponding active fragment, a derivative, or an analogue thereof.

In another preferred embodiment of the use or of the pharmaceutical composition of the present invention, the compound displaying or inducing cytokine or anti-cytokine activity and the pharmaceutically active ingredient or antigen or allergen are associated with the penetrant, e.g. in the form of a complex, hetero-aggregate, via encapsulation etc.

In an additional preferred embodiment of the use or of the pharmaceutical composition of the present invention the less soluble self-aggregating molecule is a lipid, preferably a polar lipid, and the more soluble component is a surfactant or some more soluble form of the polar/basic lipid. The former ingredient, typically, stems from a biological source or is a corresponding synthetic lipid or any of its modifications. Such lipid often belongs to the class of phospholipids with the chemical formula

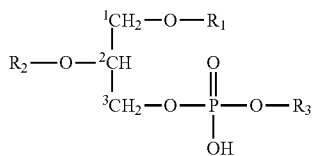

where $R_1$ and $R_2$ is an aliphatic chain, typically a $C_{10-20}$-acyl, or -alkyl or a partly unsaturated fatty acid residue, in particular, an oleoyl-, palmitoeloyl-, linoleyl-, linolenyl-, linolenoyl-, arachidoyl-, vaccinyl-, lauroyl-, myristoyl-, palmitoyl-, or stearoyl chain, and where $R_3$ is hydrogen, 2-trimethylamino-1-ethyl, 2-amino-1-ethyl, $C_{1-4}$-alkyl, $C_{1-5}$-alkyl substituted with carboxy, $C_{2-5}$-alkyl substituted with hydroxy, $C_{2-5}$-alkyl substituted with carboxy and hydroxy, or $C_{2-5}$-alkyl substituted with carboxy and amino, inositol, sphingosine, or salts of said substances, said lipid comprising also glycerides, isoprenoid lipids, steroids, sterines or sterols, of sulphur- or carbohydrate-containing lipids, or any other bilayer forming lipids, and preferably is selected from the group of phosphatidylcholines, phosphatidylethanolamines, phosphatidylglycerols, phosphatidylinositols, phosphatidic acids, phosphatidylserines, sphingomyelins or other sphingophospholipids, glycosphingolipids (including cerebrosides, ceramidepolyhexosides, sulphatides, sphingoplasmalogens), gangliosides or other glycolipids or synthetic lipids, in particular with corresponding sphingosine derivatives, or any other glycolipids, whereby two similar or different chains can be esterified to the backbone (as in diacyl and dialkenoyl compound) or be attached to the backbone with ether bonds, as in dialkyl-lipids, or belong to the backbone as in sphingolipids.

The surfactant used, normally, is nonionic, zwitterionic, anionic or cationic, especially a fatty-acid or -alcohol, an alkyl-tri/di/methyl-ammonium salt, an alkylsulphate salt, a monovalent salt of cholate, deoxycholate, glycocholate, glycodeoxycholate, taurodeoxycholate, taurocholate, etc., an acyl- or alkanoyl-dimethyl-aminoxide, esp. a dodecyl-dimethyl-aminoxide, an alkyl- or alkanoyl-N-methylglucamide, N-alkyl-N,N-dimethylglycine, 3-(acyldimethylammonio)-alkanesulphonate, N-acyl-sulphobetaine, a polyethyleneglycol-octylphenyl ether, esp. a nonaethylene-glycol-octylphenyl ether, a polyethylene-acyl ether, esp. a nonaethylen-dodecyl ether, a polyethylene-glycol-isoacyl ether, esp. a octaethylene-glycol-isotridecyl ether, polyethylene-acyl ether, esp. octaethylenedodecyl ether, polyethyleneglycol-sorbitane-acyl ester, such as polyethylenglykol-20-monolaurate (Tween 20) or polyethylenglykol-20-sorbitan-monooleate (Tween 80), a polyhydroxyethylene-acyl ether, esp. polyhydroxyethylene-lauryl, -myristoyl, -cetylstearyl, or -oleoyl ether, as in polyhydroxyethylene-4 or 6 or 8 or 10 or 12, etc., -lauryl ether (as in Brij series), or in the corresponding ester, e.g. of polyhydroxyethylen-8-stearate (Myrj 45), myristate-, -laurate, linoleate-, linolenate-, palmitoleate- or -oleate type, or in polyethoxylated castor oil 40, a sorbitane-monoalkylate, esp. sorbitane-monolaurate, -myristate, -linoleate, -linolenate-, -palmitoleate- or -oleate, an acyl- or alkanoyl-N-methylglucamide, esp. in or decanoyl- or dodecanoyl-N-methylglucamide, an alkyl-sulphate (salt), e.g. in lauryl-, myristoyl, palmitoyl, oleoyl-, palmitoleoyl-, linolenyl-, linoleoyl-, vaccinyl-, or elaidoyl-sulphate, sodium deoxycholate, sodium glycodeoxycholate, sodium oleate, sodium taurate, a fatty acid salt, with similar preference for aliphatic chains as given above, a lysophospholipid, such as n-octadecylene(=Oleoyl)-glycerophosphatidic acid, -phosphorylglycerol, or -phosphorylserine, n-acyl-, e.g. lauryl, myristoyl, palmitoyl, oleoyl-, palmitoleoyl-, elaidyl-, vaccinyl-, linoleyl-, linolenyl-glycero-phosphatidic acid, -phosphorylglycerol, or -phosphorylserine, or a corresponding short, double chain phospholipid, such as dodecyl-phosphatidylcholine, or else is a surface-active polypeptide. It is important to realise, however, that complexes of polar lipids with other amphipats often can take the role of surfactants in the coating of a carrier and that different ionisation or salt forms of the polar lipids may differ widely in their properties. It therefore stands to reason that two different physicochemical states of the same (polar) lipid mixed together in a membrane may produce a highly deformable carrier satisfying the conditions of this invention.

In an additional preferred embodiment of the use or of the pharmaceutical composition of the present invention, the more soluble component is an agent to be transported across the barrier, said agent having a tendency to form common large structures with the less soluble component(s) of the penetrant, typically in the form of a physical or a chemical complex.

In a further preferred use or pharmaceutical composition of the invention, the more soluble component tends to solubilise the penetrating droplet and is present in concentration not exceeding 99 mol % of the concentration required to disintegrate the droplet or, alternatively, not exceeding 99 mol % of the saturating concentration in the unsolubilised droplet, whichever is higher, values below 50% of the former relative concentration being particularly useful, with values below 40 rel-% or even around and below 30 rel-% being even more advantageous, whereas in the case of droplets which cannot be solubilised by the more soluble component relative concentrations which exceed the above mentioned relative concentrations by the factor of up to 2 are most preferred.

In a different preferred embodiment of the use or of the pharmaceutical composition of the invention, the less soluble penetrant component is a lipid, preferably a polar lipid and the more soluble component is a surfactant or a surfactant-like molecule or else such form of polar lipid which is sufficiently soluble for the purpose of this invention.

In another preferred embodiment of the use or of the pharmaceutical composition of the present invention, the average penetrant diameter is between 25 nm and 500 nm, preferably between 30 nm and 250 nm, even more preferably between 35 nm and 200 nm and particularly preferably between 40 nm and 150 nm.

In a different preferred embodiment of the use or of the pharmaceutical composition of the present invention the penetrant concentration in the formulation for the use in the human or animal nose is 0.001 weight-% (w-%) to 20 w-% of total dry mass in the formulation, in particular between 0.01 w-% and 15 w-%, more preferably between 0.1 w-% and 12.5 w-% and most preferred between 0.5 w-% and 10 w-%.

In a further preferred embodiment of the use or of the pharmaceutical composition of the present invention the supporting medium, e.g. a buffer, is selected to be a biocompatible solution with an osmotic activity similar to that of a monovalent electrolyte with a concentration range between 1 mM and 500 mM, more preferably between 10 mM and 400 mM, even more preferably between 50 mM and 300 mM, and most preferably between 100 mM and 200 mM or else such solution that affords practically sufficient penetrant stability combined with practically sufficient transport rate across the barrier. The term "practically sufficient penetrant stability" means that the penetrant stability meets the reasonable product quality criteria. The term "practically sufficient transport rate" means that enough drug is transported through the barrier without using unreasonably large application volume or time. Said sufficient penetrant stability combined with sufficient transport rate across the barrier can be determined by the person skilled in the art without undue experimentation.

In another preferred embodiment of the use or of the pharmaceutical composition of the present invention, the relative drug or agent concentration is between 0.001 w-% and 40 w-% of total penetrant mass, in particular between 0.01 w-% and 30 w-%, even better between 0.1 w-% and 25 w-% and most preferably between 0.5 w-% and 15 w-%.

In one further preferred embodiment of the use or of the pharmaceutical composition of the present invention the medium supporting the drugs and carriers is a biocompatible buffer with pH value between 4 and 10, more frequently between 5 and 9 and most often between 6 and 8.

In another preferred embodiment of the use or of the pharmaceutical composition of the present invention additives are included in said composition to reduce the system sensitivity to chemical, biological or ambient stress, including anti-oxidants, antagonists of undesired enzyme action, cryo-preservants, microbicides, etc., or else modulators of physically important system properties, such as formulation viscosity, etc.

In a different preferred embodiment of the use or of the pharmaceutical composition of the present invention the relative drug or agent dose to be administered non-invasively through the nose by means of highly adaptable carriers is chosen to be between 0.1× and 500×, more often between 0.5× and 250×, and even more preferably between 1× and 100× different from the corresponding drug or agent dose that would have to be injected to achieve the desired biological effects. Again, the latter dose can be determined by the person skilled in the art without undue experimentation and on the basis of his common general knowledge.

In another preferred embodiment of the use or of the pharmaceutical composition of the present invention the applied penetrant dose is between 0.01 mg and 15 mg per nostril, even more often is in the range 0.1 mg and 10 mg per nostril, and preferably is between 0.5 mg and 5 mg per nostril.

The efficiency of administration and the biological effects of the agent or drug chosen, consequently, can be controlled by using different application volumes. Various metered delivery devices can be used for the purpose.

Accordingly, in an additional preferred embodiment of the use or of the pharmaceutical composition of the present invention said formulation is administered using a metered delivery device.

In one further preferred embodiment of the use or of the pharmaceutical composition of the present invention different application volumes are selected to control the efficiency of administration and the biological effects of the chosen agent or drug.

In a different preferred embodiment of the use or of the pharmaceutical composition of the present invention the penetrants in suspension are loaded with the drugs or agents within 24 hours prior to the formulation administration, preferably 360 min, more preferably 60 min and even more preferably 30 min before the resulting formulation is administrated in the nose. This embodiment is expected to improve the formulation stability, loading efficiency, the release kinetics, ease of use, compliance, etc.

In another preferred embodiment of the use or of the pharmaceutical composition of the present invention the delivery device is loaded at the treatment site.

In a further preferred embodiment of the use or of the pharmaceutical composition of the present invention the delivery device is loaded separately with penetrants and the molecules, particularly biological agents, to be associated therewith.

In one further preferred embodiment of the use of the present invention wherein the pharmaceutically active ingredient is for administration to the nervous system.

The term "administration" in connection with this embodiment means that the pharmaceutical composition is transnasally applied, but the target site of the active ingredient is the nervous system, preferably the CNS and most preferably the brain. The possibility to use nasal application of the highly adaptable, drug-loaded penetrants in the nose to mediate a practically useful transfer of the drug across the barrier can thus be exploited to transport a meaningful amount of the drug, and to create a significant concentration of such drug, in the central nervous system or some other adjacent tissue, such as the eye.

In another preferred embodiment of the invention, the pharmaceutical composition of the invention is a vaccine.

Said vaccine can be used for therapeutic or prophylactic vaccination.

The term "(therapeutic) vaccination" in the context of this invention describes any kind of therapeutic immunisation, whether done after the disease has been already established, to improve a clinical situation, or else for the purpose of preventing a disease. Such a vaccination can involve single or repeated administration(s) of the vaccine of the invention. Therapeutic vaccination will either prevent a pathological situation and/or improve a clinical situation. When applied as a preventive agent, it will generally result in a protective immune response.

Immunisation denotes any kind of provoking an immune response, irrespective of whether said response is therapeutic or non-therapeutic.

An "antibody" or an "immunoglobulin" denotes an IgA, IgD, IgE, IgG, or IgM, including all subtypes, such as IgA1 and IgA2, IgG1, IgG2, IgG3, IgG4. Their "derivatives" include chemical, biochemical and otherwise obtainable derivatives, such as genetically engineered antibody derivatives. Fragments include e.g. single chain fragments, Fc-, Fab-F(ab')$_2$- and other parts of Ig-s, independent of whether they are of endogenous, xenogenic, (semi)synthetic or recombinant origin. Also comprised by the invention are complexes of two or more of the above-recited antibodies, derivatives or fragments.

The term "immunogen" denotes a hapten coupled to an immunological carrier or an antigen, free or associated with a carrier, which is capable of inducing an immune response.

"Immuno-tolerance" denotes the lack or, more generally, the reduction of an undesired immune response to an antigen.

Th1 (T-helper cell type I) related antibodies include IgG2a, IgG2b and IgG3.

Th2 (T-helper cell type II) related antibodies comprise the classes of IgG1, IgG4 and IgE.

As has been indicated above, the successful immunisation with the vaccine of the invention through the nose is a significant step forward in the design of conveniently administrable vaccines that (a) are highly efficient over a wide range of immunogens of varying size and properties; (b) can be formulated together with certain cytokines, compounds that mediate cytokine activity or compounds that antagonize cytokine activity in order to specifically direct the corresponding immune response or to augment or suppress the same as may be desired; (c) do not depend on the perturbing injection by a needle; and (d) cause no irritating side effects. In addition, with the vaccine of the invention, successful tolerogenisation may be achieved.

It has inter alia been found in accordance with the present invention that
- Tween-SPC micelles give protection significantly below that of the vaccine of the present invention, suggesting that the small size of the carrier or the presence of surfactants alone does not suffice for a successful immunisation;
- orally administered immuno-carriers create lower specific antibody titers than the transnasally administered vaccine of the invention, as determined on the basis of absorbance measurements;
- the transnasal vaccine of the invention gives rise to higher specific IgG1 and IgG2 titers in the blood and to comparable IgG2a and IgM titers as compared to mixed micelles; all titers were, on top of this, higher than those generated by immunisation with SPC:cholesterol (1:1) liposomes.

When the transnasal vaccine of the invention is formulated together with a cytokine or an immunoadjuvant it is advantageous to use (blends of) bacterial extracts. Specific examples given in this application include monophosphoryl lipid A (MPL) and IL-12 or GM-CSF and IL-4. In principle, however, the vaccine of the invention may be formulated or applied together with any of the compounds mediating, inducing or displaying cytokine activity or with antagonists thereto that have been recited herein above.

It is preferred that the vaccine of the invention further comprises a pathogen extract or a compound from a pathogen or a fragment or a derivative thereof.

Most preferably, said pathogen extract or compound is selected from hepatitis virus, (human) immunodeficiency virus, herpex viruses, small-pox (chicken-pox), influenza, measles, mumps or polio viruses, cytomegalovirus, rhinovirus, etc., or fungi prospering inside host cells, a parasite including animal parasites, such as protozoa and helminths, and ectoparasites, such as ticks and mites, or *Brucella* species, including the causative agent for cholera (e.g. *Vibrio cholerae*), *Haemophilus* species, as well as pathogens triggering paratyphoid, plague, rabies, tetanus or rubella diseases.

It is additionally preferred that said vaccine further comprises an adjuvant.

The term "adjuvant" is used here to describe any substance which supports, augments, stimulates, activates, potentiates or modulates the desired immune response of either cellular or humoral type, specifically in the case of a prophylactic treatment by increasing the antigen specific immune response of any kind and in the case of therapeutic treatment often by supporting cell-mediated immunity. This can be achieved by the addition of suitable cytokines, their blends or suitable agonists and antagonists. The class of immunoadjuvants which indirectly contribute to the useful cytokine pool includes small chemical entities with an allergenic potential, such as certain allergenic (metal) ions, including but not limited to LiCl, HgCl$_2$, molibdenum, acids, bases and other irritating compounds, such as dicyclohexylmethane-4,4'-diisocyanate, ditrocarb (diethyldithiocarbamate), 2,4-dinitrochlorobenzene, isoprinosine, isophorone-diisocyanate, levamisole, (phenyl)oxazolone and alike, Swansonine, sizofran, phthalic anhydride, thymopentin, (fatty) alcohols, (fatty) amines, (fatty) ethers, ricin, or other suitable amphiphiles, many surfactants and chemical permeation enhancers, as well as derivatives or combinations thereof; furthermore, (low molecular weight) fragments of or derivatives from microbes, including lipopolysaccharides (such as LPS), cord-factor (trehalose-dimycolate) and other (poly)saccharides or (poly)peptides attached to membranes, used in sufficient quantity, acetylmuramyl-alanyl-isoglutamin, and larger fragments of microbes, including bacterial exo- and endotoxins, or enterotoxins, such as cholera toxin and the heat labile toxin of *E. coli*, and their macromolecular fragments, such as A-chain derivatives, most, if not all, of which seem to posses ADP-ribosylating activity, the high potency immunoadjuvant LT holotoxin, etc., cell-wall skeleton, attenuated bacteria, such as BCG, etc. Less established examples include clostridial toxin, purified protein derivative of *M. tuberculosis*, LT-R192G, Fibronectin-binding protein I of *Streptococcus pyrogenes*, outer membrane protein of group B *Neisseria meningitidis* (GBOMP), various other peptidoglycanes, etc. Immunoadjuvants, in other words, include molecules that alter the uptake or presentation of antigens, activate or increase the proliferation of antigen specific lymphocytes, or interfere with the dominant control mechanism in the immune response, not just in the nose but also in the other immunocompetent tissues. (The mucosal adjuvant activity of ADP-ribosylating bacterial enterotoxins is a well established and known example for this.) On the other hand, molecules which change the (relative) concentrations of cytokines or other immunoadjuvants, such as anti-immunoadjuvant antibodies or other agonists or antagonists of immunoadjuvants, also are immunoadjuvants in the sense of this invention. The same is true for molecules which affect lymphocyte homing, such as various selectins (LECAMS, e.g. various CD62-s), GlyCAM-1, MadCAM-1, VCAM-1, ICAM-1, hyaluronate, etc., and other chemokines, such as RANTES or MCP-1. Endogenous group of immunoadjuvants furthermore comprises histamines, transfer factor, tuftsin, etc. As many of the above mentioned immunoadjuvants do not have sufficient potency to ensure the desired effect after the non-invasive immunisation at too low, and sometimes too high, concentration or on their own, the functional definition of an adjuvant used in this work includes a fortiory sufficient and such modulation of cytokine concentration and distribution pattern in the body that results in mounting the desired therapeutic or prophylactic immune response. If required to gain clarity said modulation and its extent must be determined in a dedicated experiment, in which the specific cytokine levels are determined, using methods known to the person skilled in the field.

In a further preferred embodiment of the vaccine of the invention, said adjuvant is lipopolysaccharide, such as lipid A or a derivative or modification thereof, such as monophosphoryl lipid A, or its analogue, such as a fatty derivative of saccharose, cord-factor (trehalose-dimycolate), muramyl dipeptide, or another (poly)saccharide or (poly)peptide identical to or resembling an immunologically active part of a membrane of a microorganism; an extract of a microorganism, including bacterial exo- and endotoxins, preferably cholera toxin or the heat labile toxin of *E. coli*, an A-chain derivative, a component with an ADP-ribosylating activity, a peptidoglycane, a clostridial toxin, an LT halotoxin, purified protein derivative of *M. tuberculosis*, LT-R192G, Fibronectin-binding protein I of *Streptococcus pyrogenes*, or outer membrane protein of group B *Neisseria meningitidis* (GBOMP), bacterial or viral nucleic acids, such as oligonucleotides comprising unmethylated CpG dinucleotides.

It is most preferred that the vaccine of the invention comprises a blend of MPL and IL-12 or GM-CSF and IL-4, when pure cytokines and their inducers are used.

In a different preferred embodiment of the vaccine of the present invention the relative immunogen/antigen dose to be administered non-invasively through the nose by means of highly adaptable carriers is chosen to be between 0.01× and 100×, more often between 0.05× and 75×, and even more preferably between 0.1× and 50× different from the corresponding immunogen/antigen that would have to be injected to achieve the desired biological effect. Again, the latter dose can be determined by the person skilled in the art without undue experimentation and on the basis of his common general knowledge.

It is further preferred in accordance with the invention that in said vaccine the concentration of the transnasally administered adjuvant is between 10× lower and up to 1000× higher than used with the corresponding subcutaneously injected formulations employing similar antigen, the transnasally administered immunoadjuvant concentration more often differing from the injected immunoadjuvant concentration by the factor between 0.5 and 100, or better, by the factor between 1 and 50, and best between 2 and 25.

The invention also relates to a container comprising the pharmaceutical composition recited herein-above. The unit dosage may be determined according to the desired application.

Furthermore, the invention additionally relates to a package comprising at least one container comprising the pharmaceutical composition as described above. The package of the invention can comprise one, two, three, four or more vials/units of the pharmaceutical composition of the invention.

The invention finally relates to methods of treating a patient in need thereof comprising transnasally administering any of the above recited pharmaceutical compositions.

The present invention further relates to a method for generating a protective or tolerogenic immune response on a mammal by vaccinating said mammal with a vaccine as described above.

In a preferred embodiment of the method according to the present invention different administration volumes are selected to control the applied immunogen dose and the outcome of vaccination. Various metered devices can be used for the purpose.

In one more preferred embodiment of the method according to the present invention a suspension of antigen-free penetrants is loaded with the antigen to be associated therewith during the day prior to an administration, preferably 360 min, more preferably 60 min and even more preferably 30 min before administering the resulting formulation in the nose.

In another preferred embodiment of the method according to the present invention at least one dose of vaccine is administered.

This embodiment of the method of the invention includes the repeated administration of the vaccine of the invention. Repeated administration includes repeated administration in the nose or one or more administrations in the nose in combination with conventional, e.g. parenteral administrations. In this connection, the kit of the invention may be advantageously made to comprise one or more containers, ampules or other kind of units comprising the vaccine of the invention.

In a particularly preferred embodiment of the method according to the present invention the time interval between the subsequent vaccinations is chosen to be between 2 weeks and 5 years, often between 1 month and up to 3 years, more frequently between 2 months and 1.5 years.

In a further preferred embodiment, repeated immunogen administration is advocated to maximise the final effect of a therapeutic vaccination. It is proposed to use between 2 and 10, often between 2 and 7, more typically up to 5 and most preferred up to 3 immunisations, when a non-allergenic antigen is used, or such a number of times, in the case of allergens, as is required either to achieve the desired immuno-tolerance, determined as described above or by some other suitable assessment method, or else to deem the effort as having failed. The time interval between subsequent vaccinations should preferably be between 2 weeks and 5 years, often between 1 month and up to 3 years, more frequently between 2 months and 1.5 years, when a subject is being immunised for the first time. Rodents, such as mice and rabbits are advantageously immunised in 2 weeks interval, primates, e.g. monkeys and often humans, need a booster vaccination in 3-6 months interval.

In another preferred embodiment of the method according to the present invention the flux of penetrants that carry an immunogen through the various pores in a well-defined barrier is determined as a function of the suitable driving force or a pressure acting across the barrier and the data are then conveniently described by a characteristic curve which, in turn, is employed to optimise the formulation or application further.

The disclosure content of the documents cited throughout this specification are herewith incorporated by reference. Further incorporated by reference is the complete disclosure content of the co-pending application filed in the name of IDEA AG and bearing the title "Noninvasive vaccination through the skin" (U.S. application Ser. No. 09/890,335: published as WO 00/44349).

The figures show:

Figure 3A:
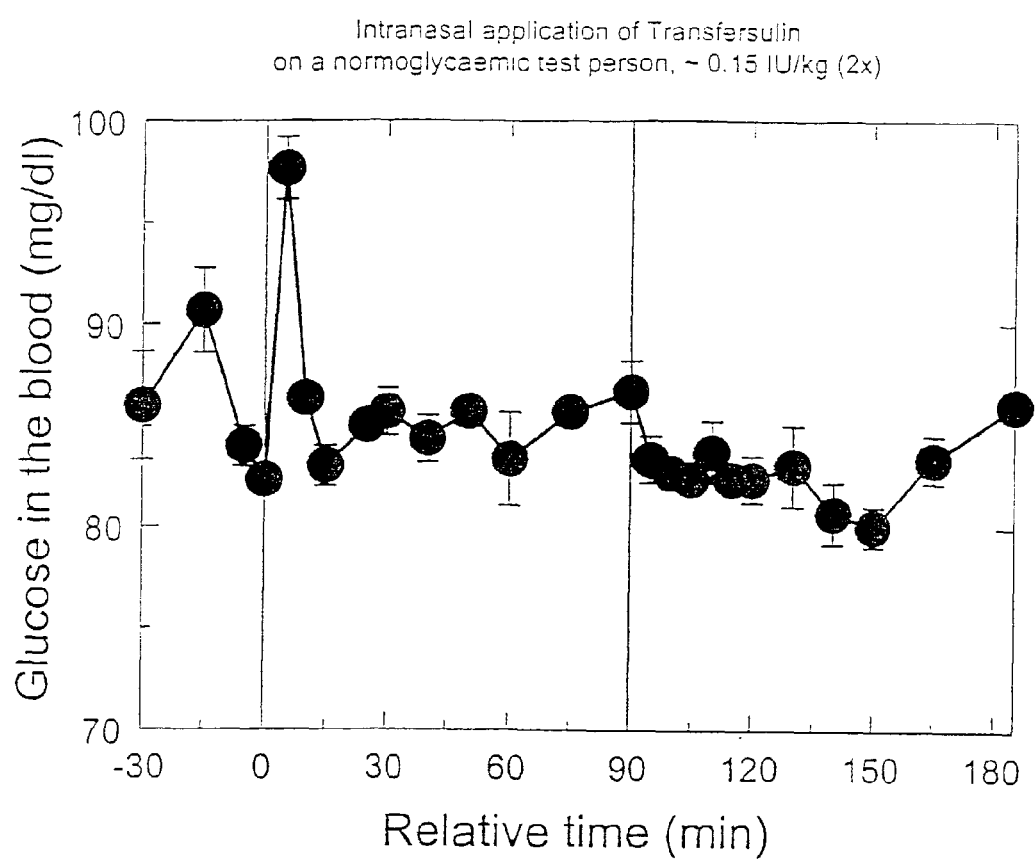
Figure 3B:
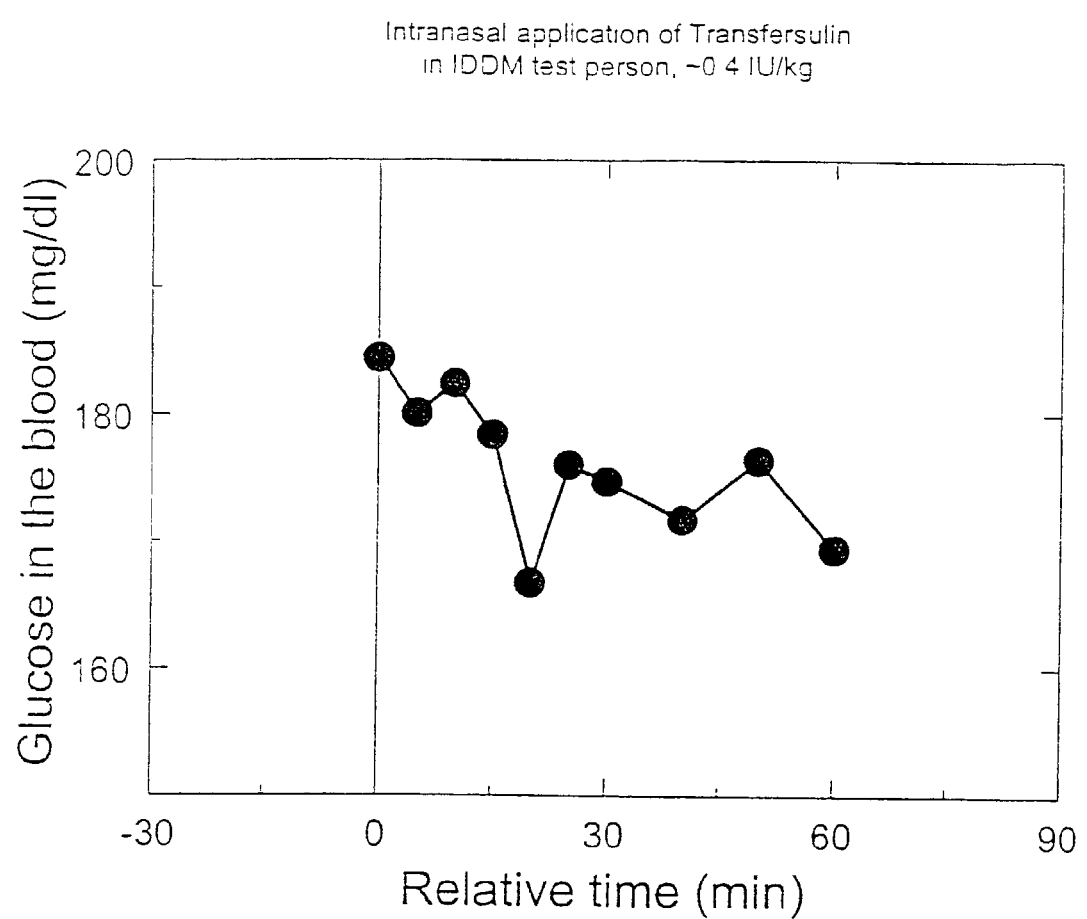

FIGS. 3a and 3b provide further examples measured with a healthy volunteer (FIG. 3a) and an insulin-dependent diabetes mellitus patient (FIG. 3b) following intranasal administration of insulin formulations with inferior characteristics, believed to be due to too slow drug release from the carrier.

Figure 4:
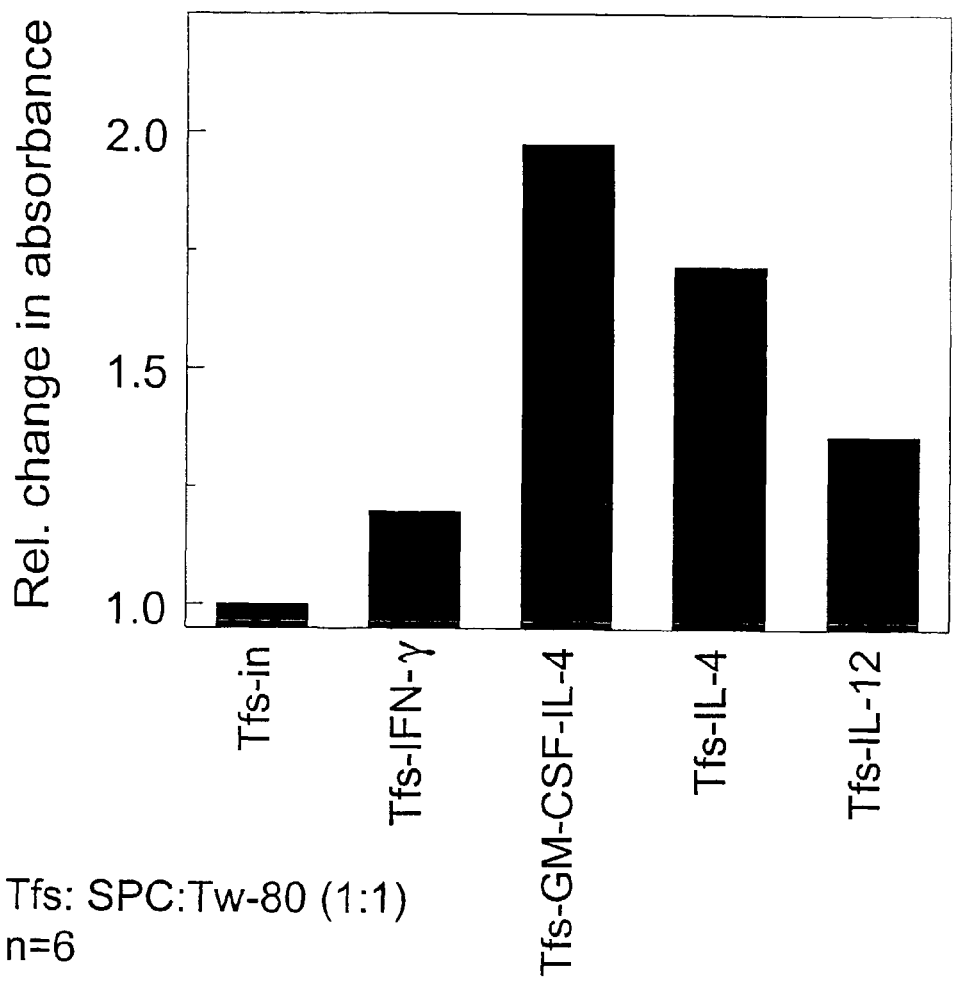

FIG. 4 illustrates the capability of nasally administered cytokines, associated with Transfersomes, to affect the outcome of transnasal immunisation with tetanus toxoid.

Figure 5:
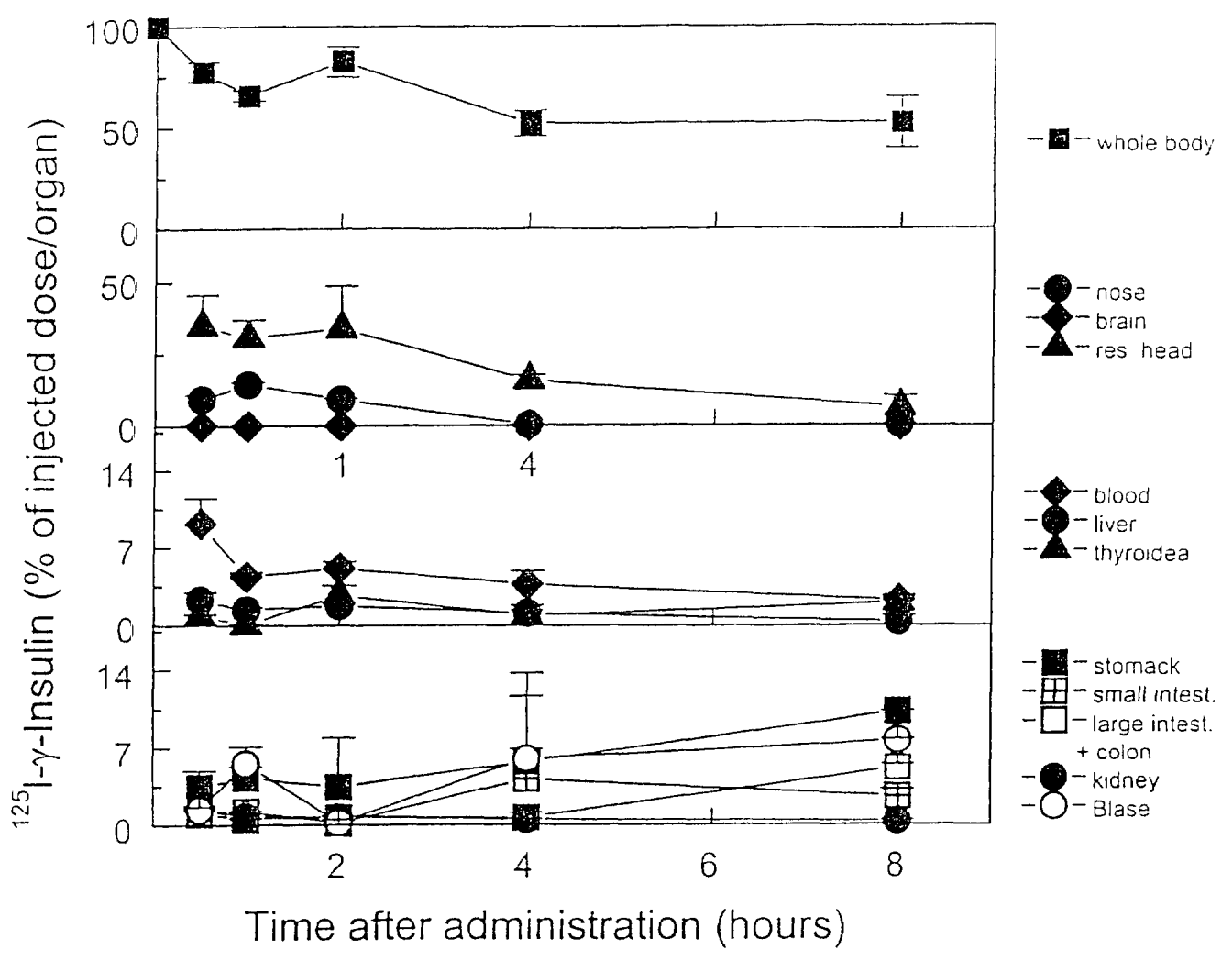

FIG. 5 illustrates the biodistribution of insulin-derived radioactivity in mice following nasal administration of the agent in transfersomes.

Figure 6:
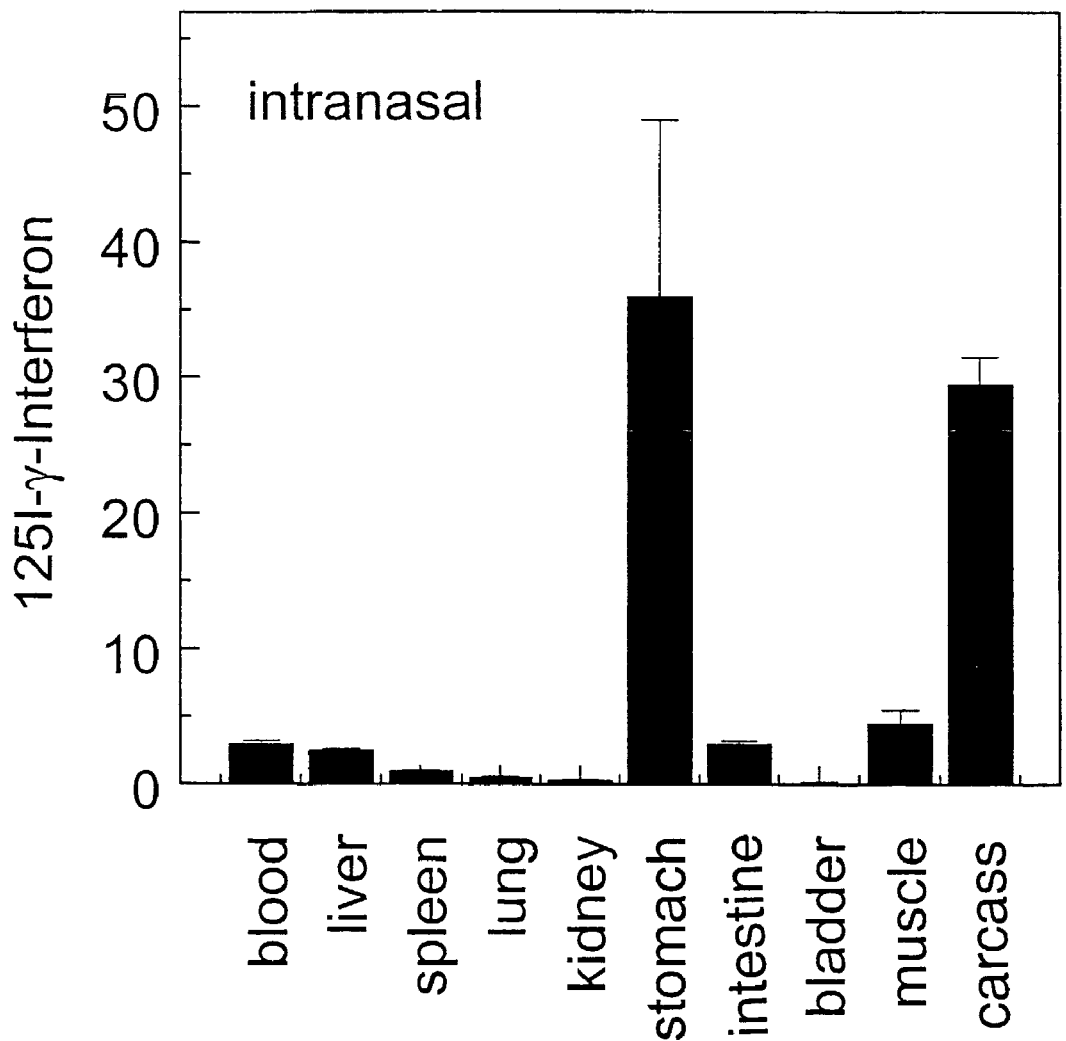

FIG. 6 gives the corresponding results for interferon, as measured in mice.

Figure 7A:
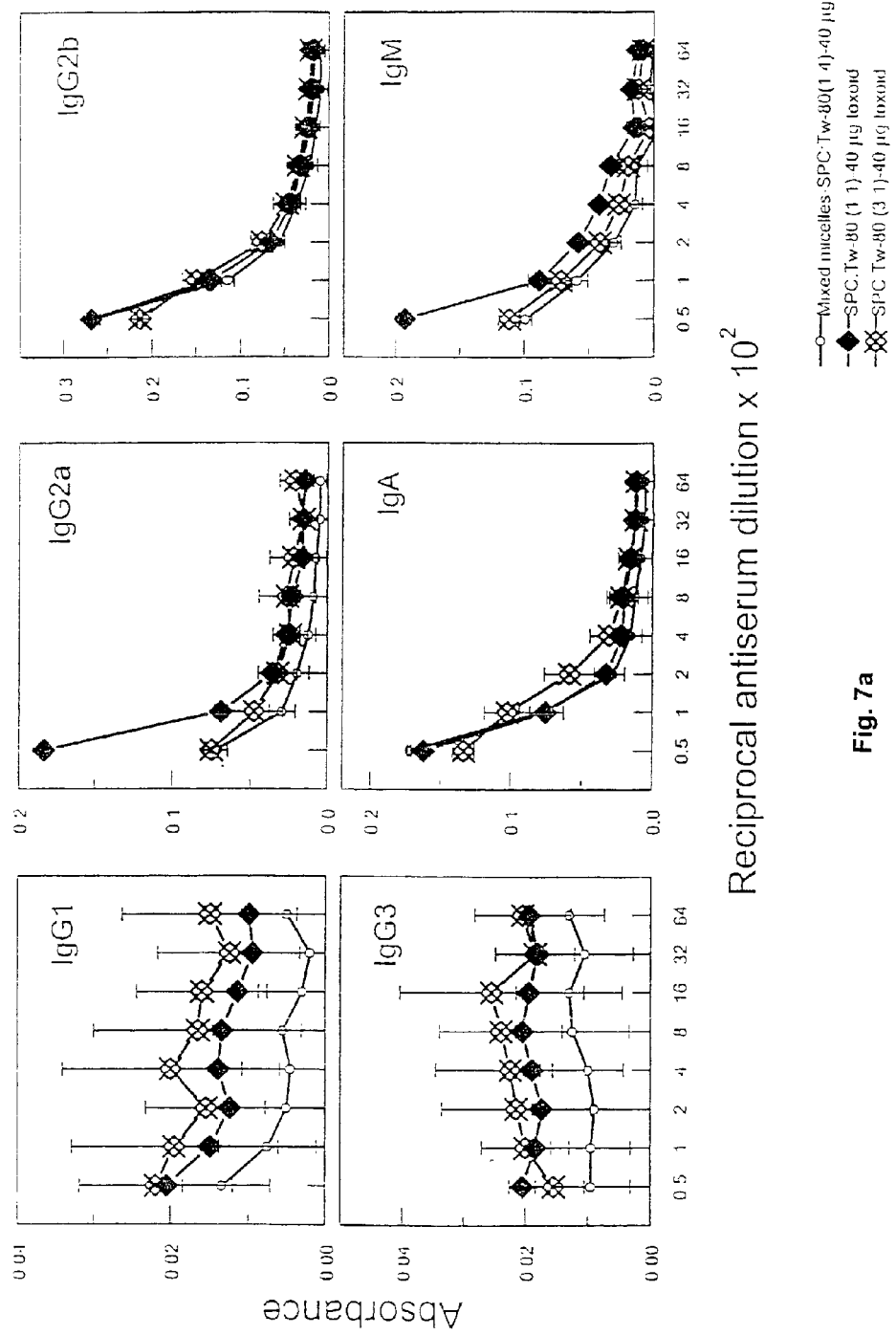
Figure 7B:
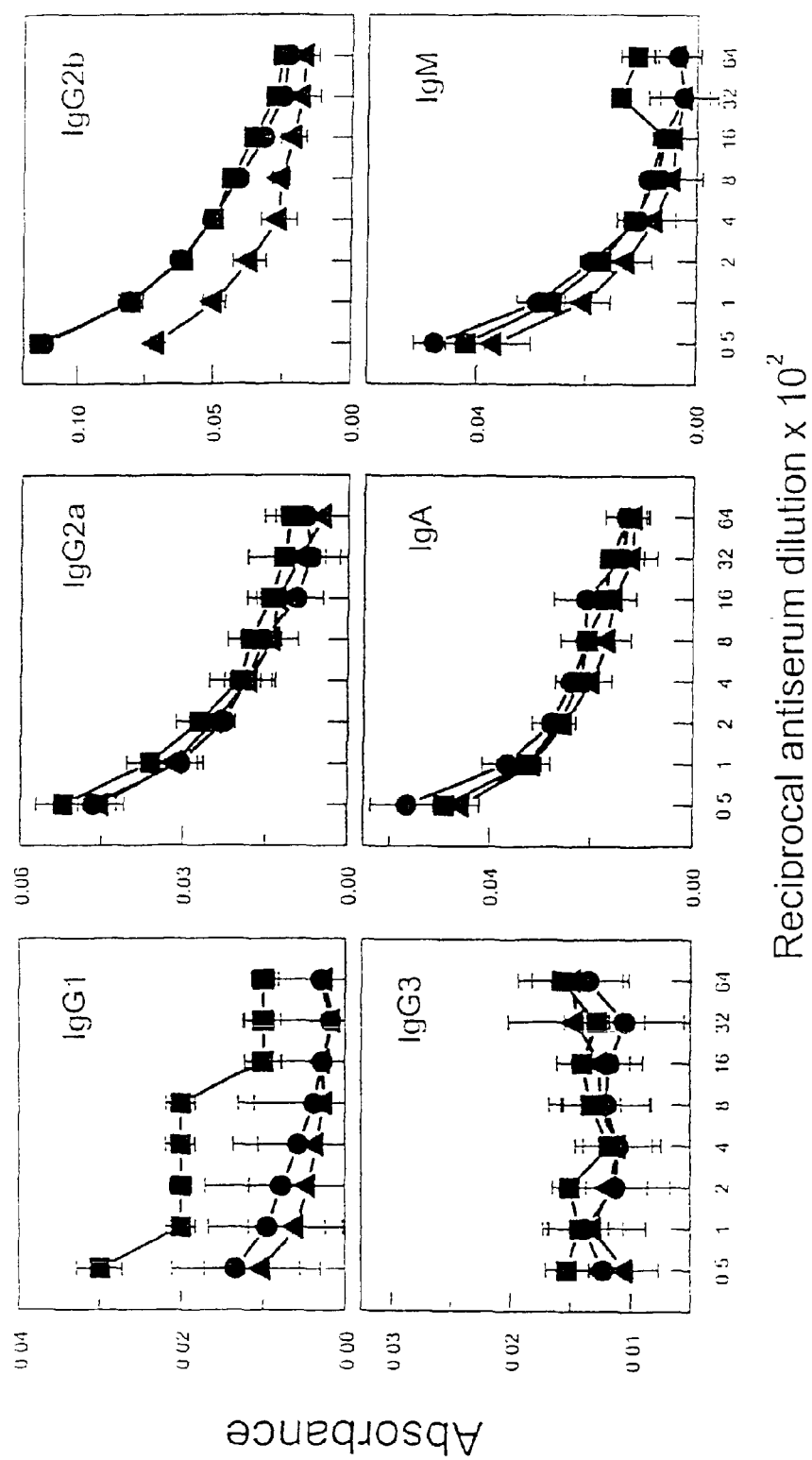
Figure 7C:
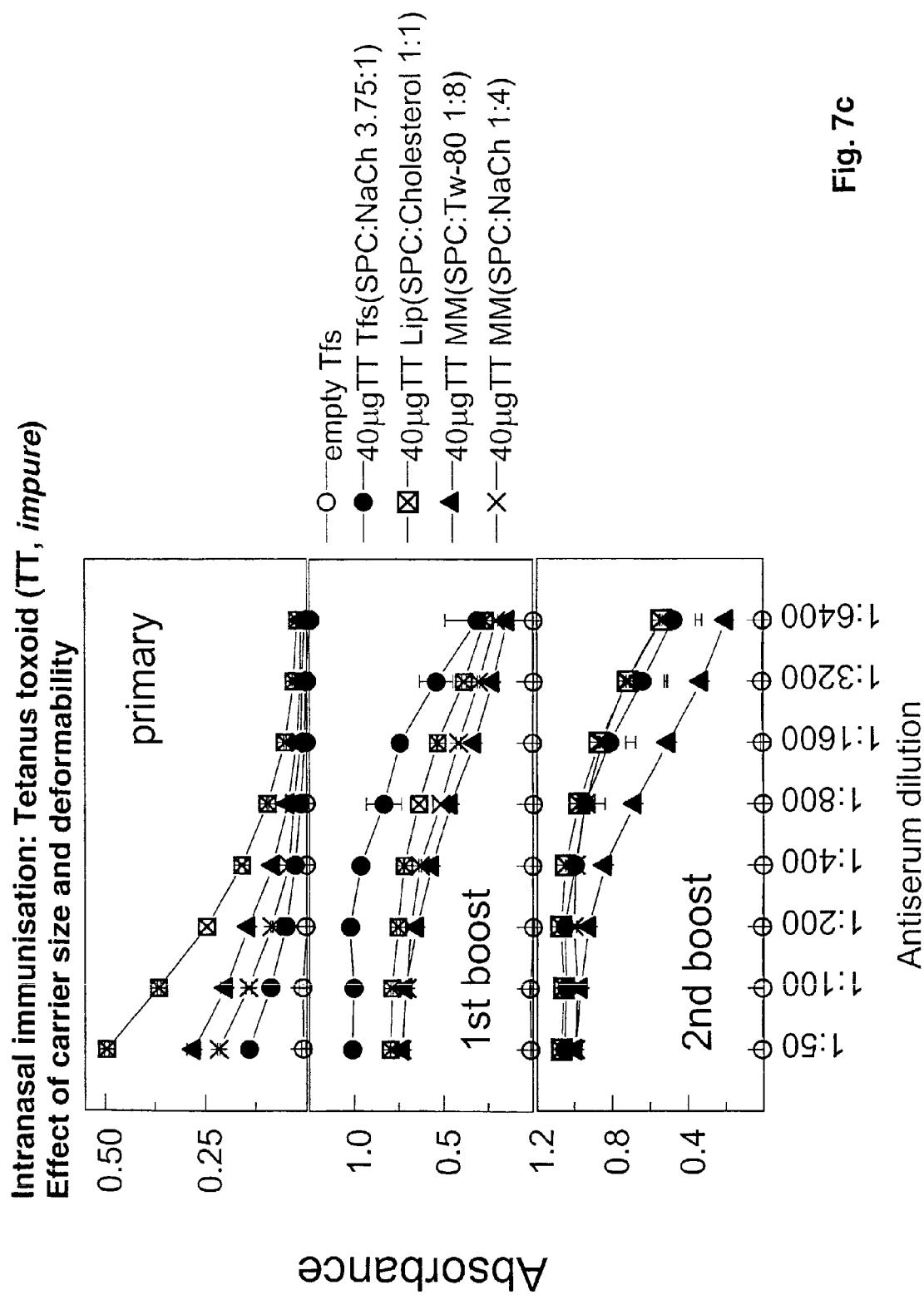

FIGS. 7a, 7b and 7c illustrate the effect of changing aggregate size and/or deformability TT specific immune response in mice treated with various mixed micelles, Transfersomes or liposomes loaded with TT. Panels a and b show antibody isotype patterns, and in panel c the total antibody titre, as expressed in absorbency change is given.

Figure 8A:
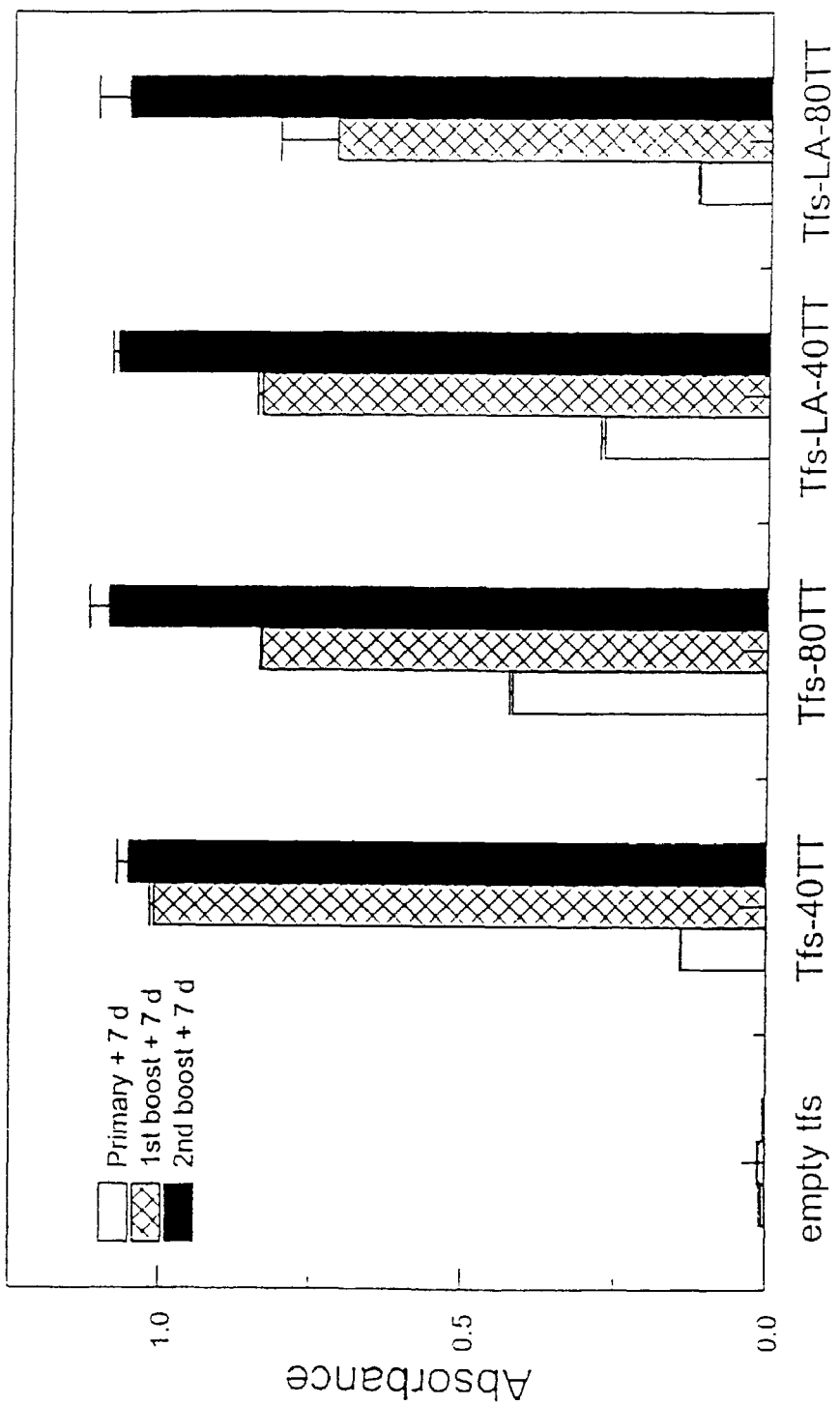
Figure 8C:
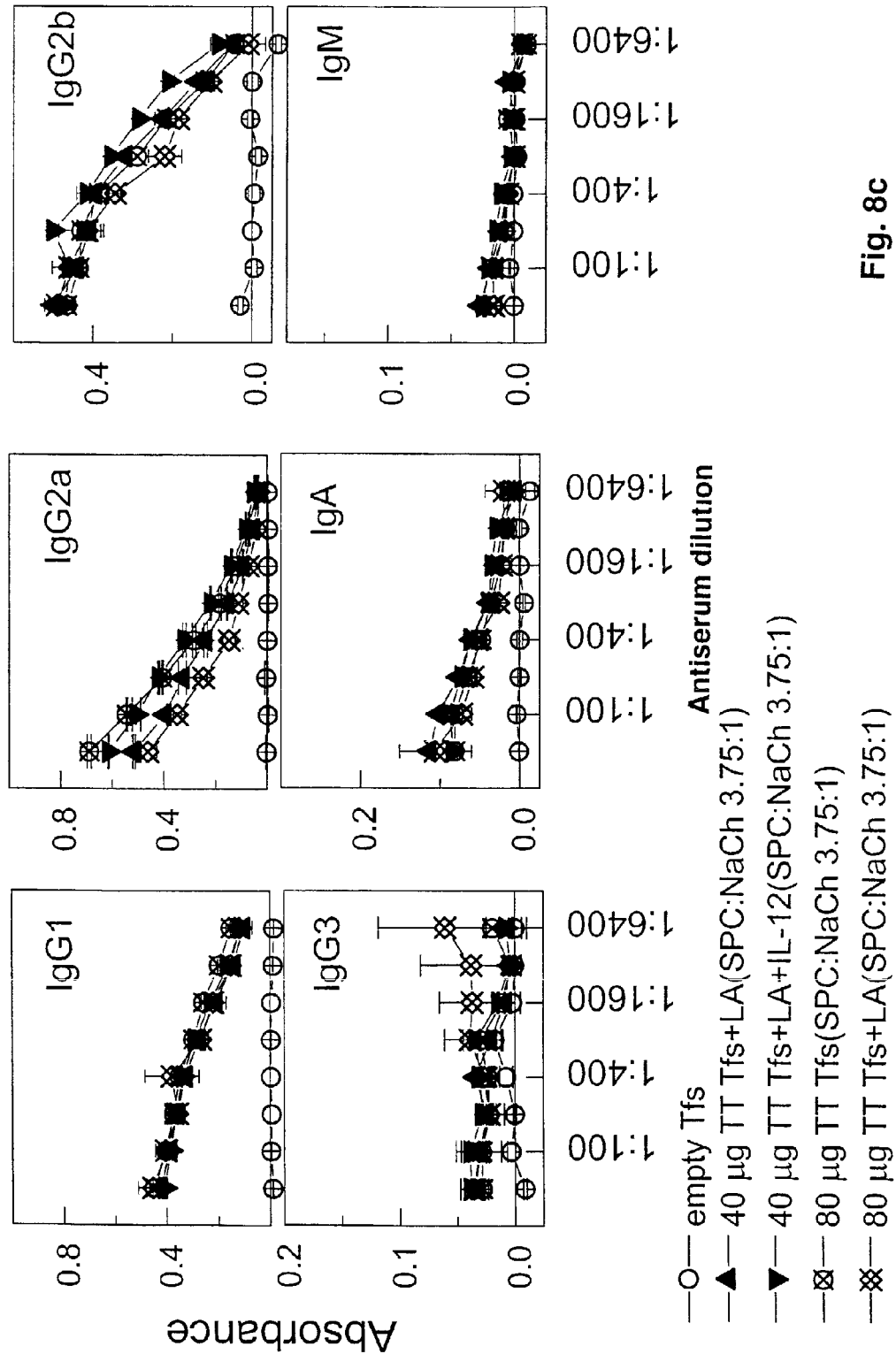

FIG. 8a, 8b and 8c highlight the (small) effect of changing antigen dose (in the high dosage range) on transnasal immunization of mice with TT by means of Transfersomes with or without lipid A derivative as an immunoadjuvant. In panel a, the results of total absorbance measurements are given, panel b shows the corresponding titration curves, and panel c gives the relevant antibody isotypes.

Figure 9A:
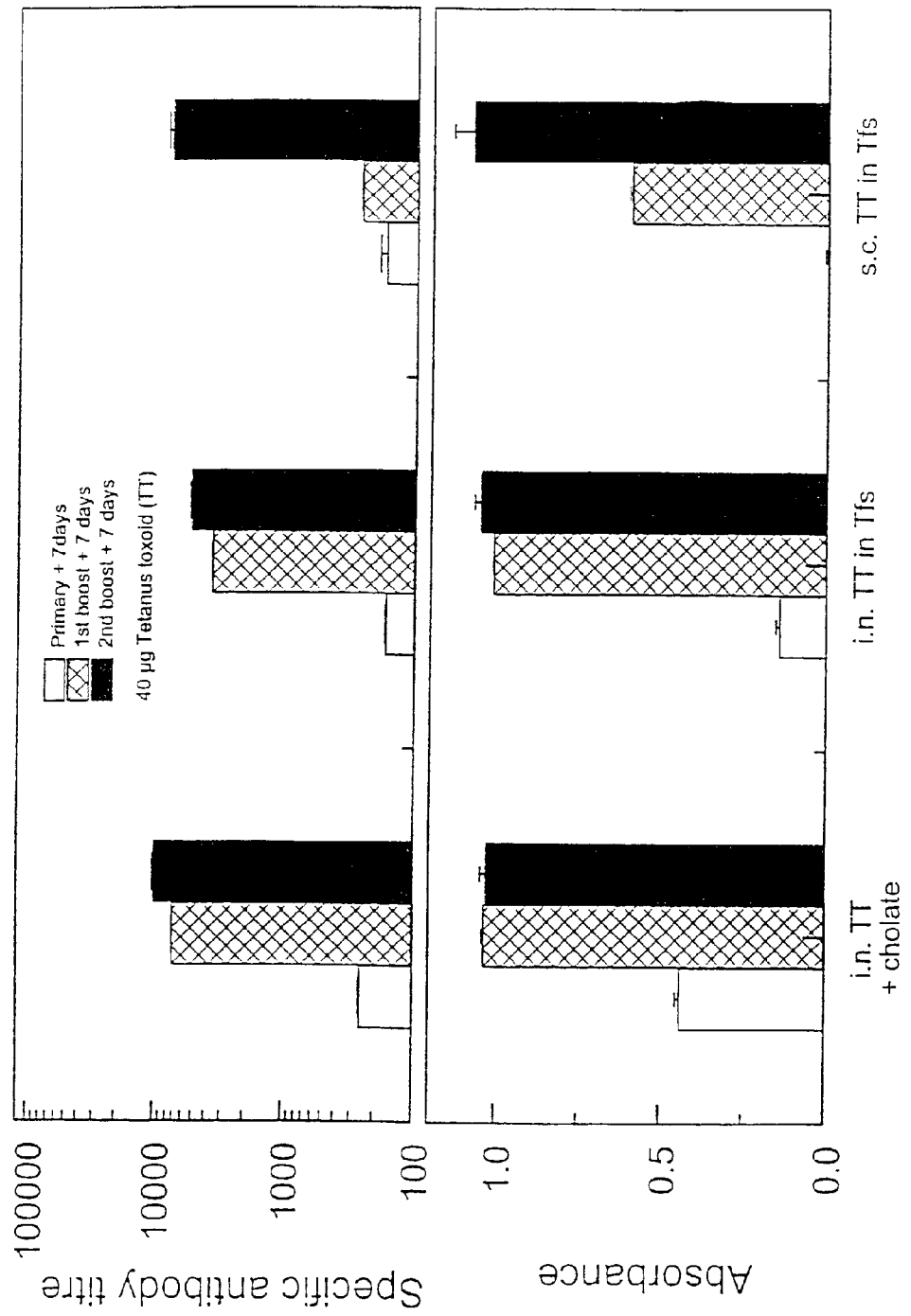
Figure 9B:
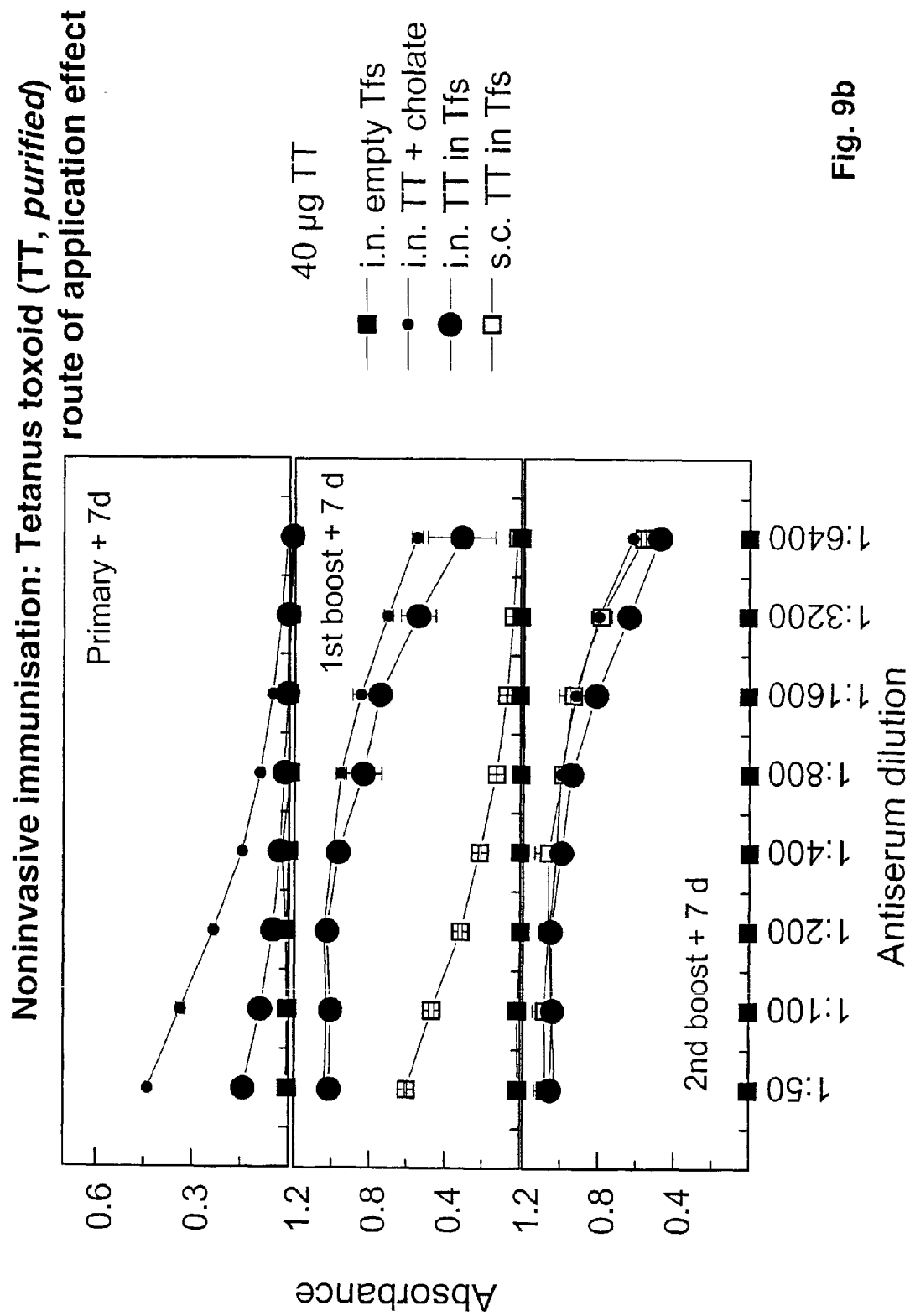
Figure 9C:
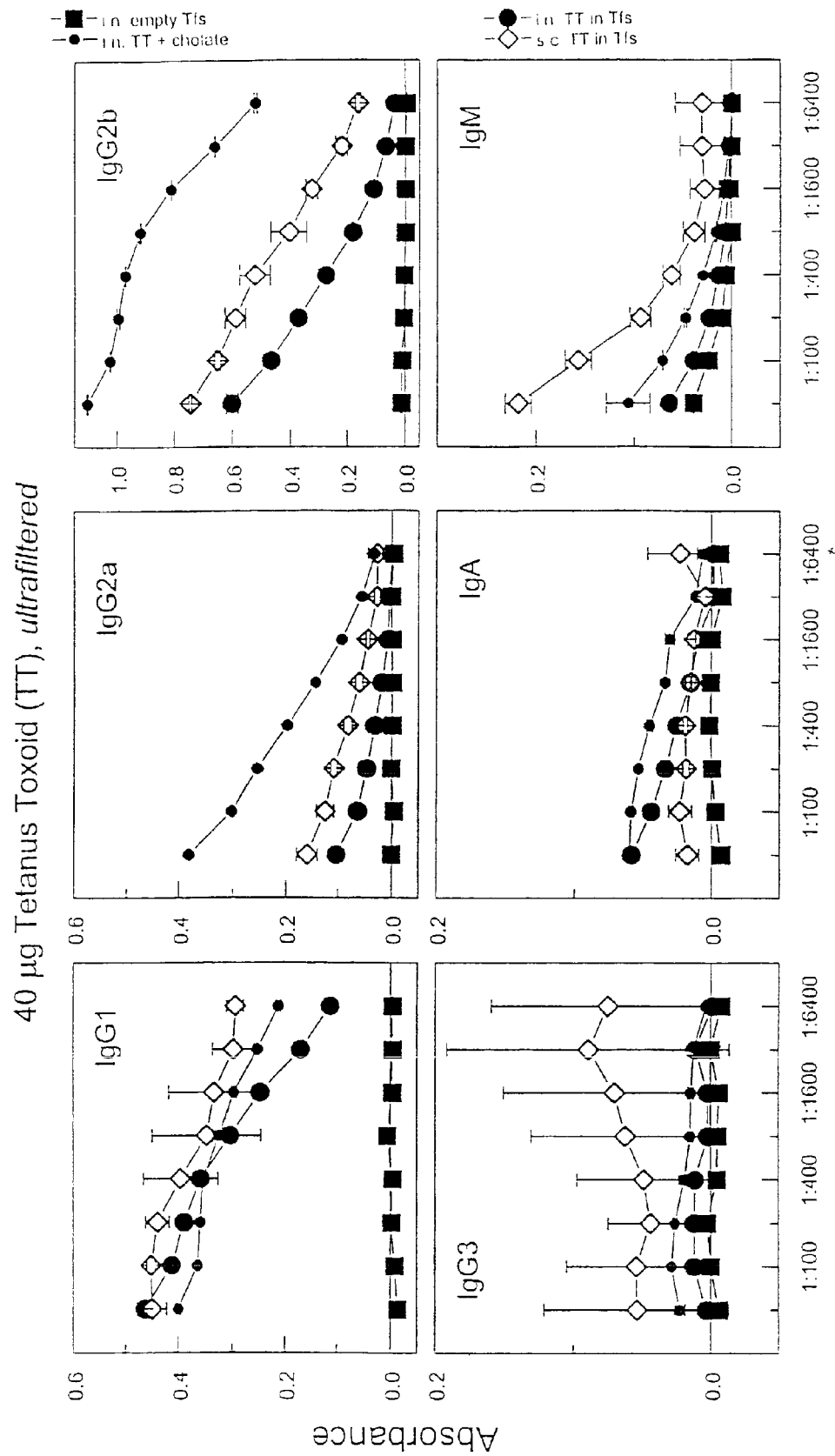

FIGS. 9d, 9b and 9c are organized in similar fashion to compare the outcome of intranasal, oral or subcutaneous TT administration using different antigen doses and purity.

Figure 10A:
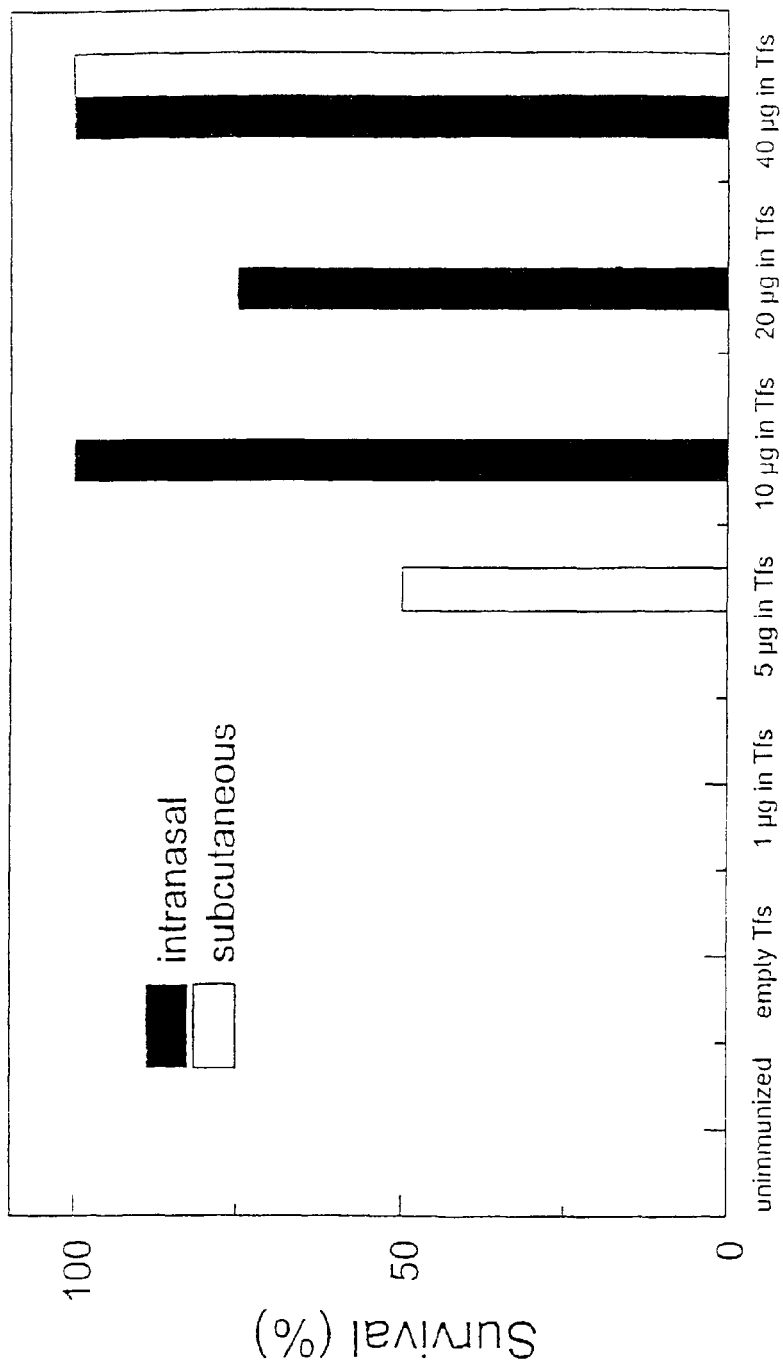
Figure 10B:
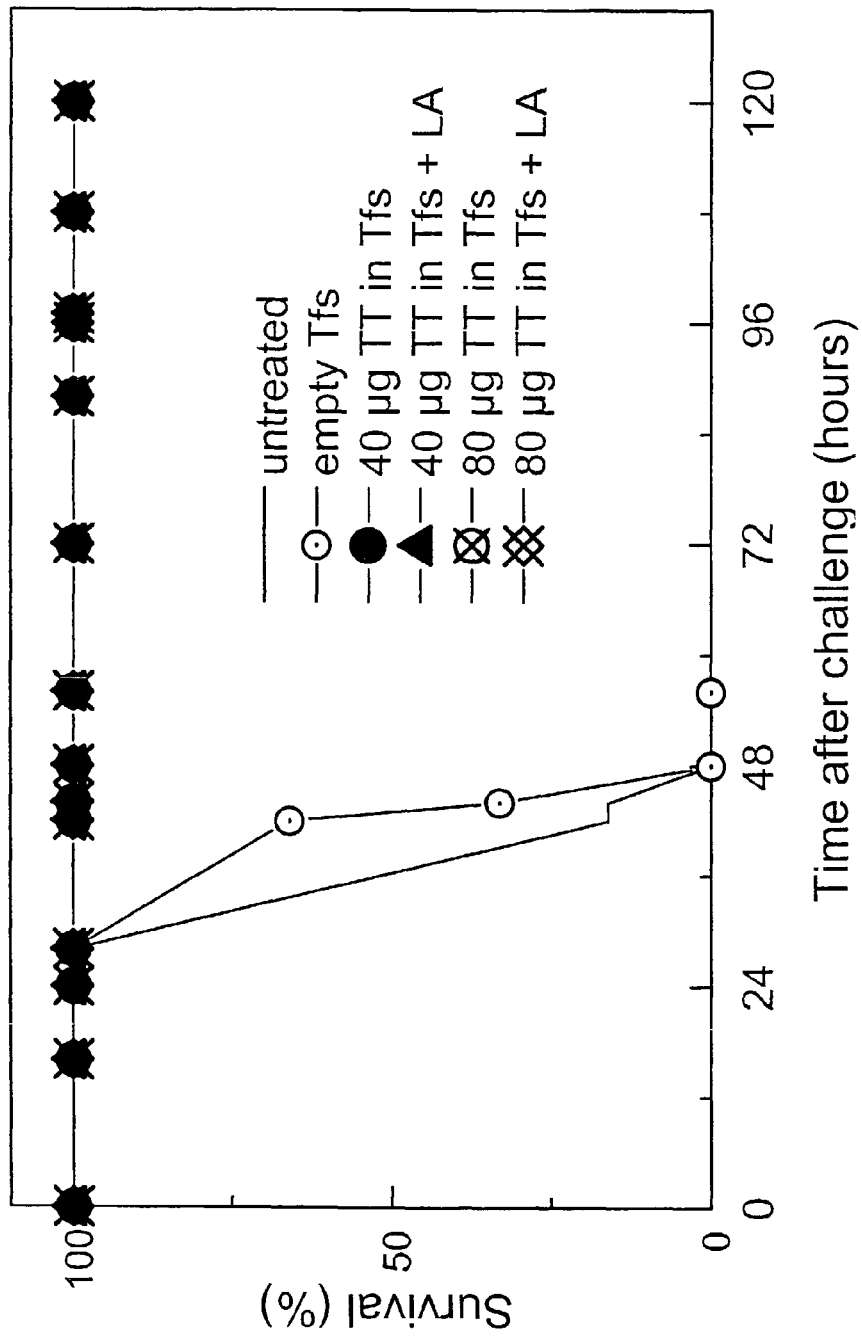

FIGS. 10a and 10b: For comparison, animal protection (survival) data are given for the experiments in which several doses and administration routes were compared.

Figure 11A:
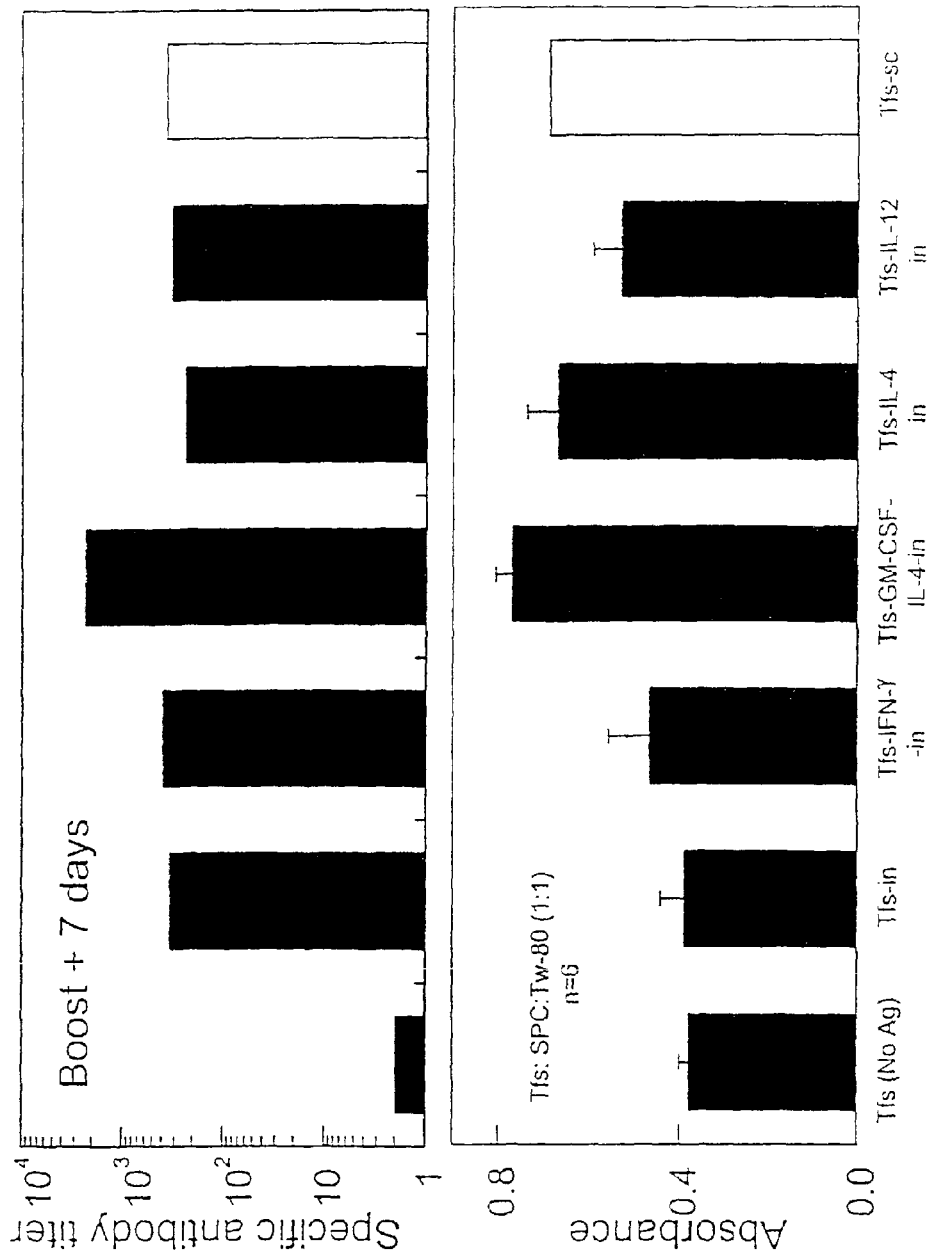
Figure 11B:
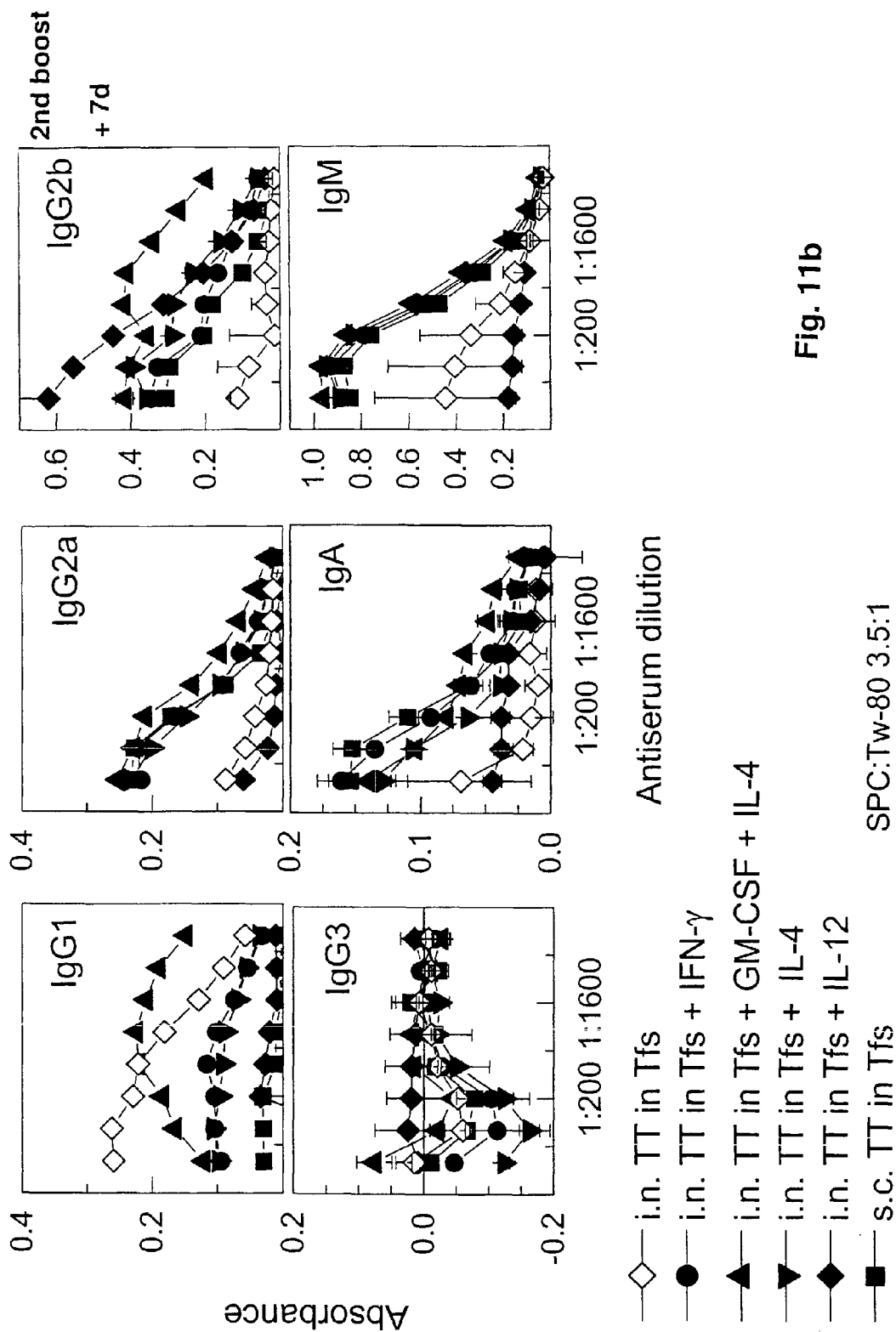

FIGS. 11a and 11b present a set of data on the effect of various cytokines, or their combination, on the murine immune response to TT administered into the nose by means of transfersomes, with s.c. data given for comparison. Panel a gives the absorbance and titre data and panel b contains the isotype distribution results.

Figure 12:
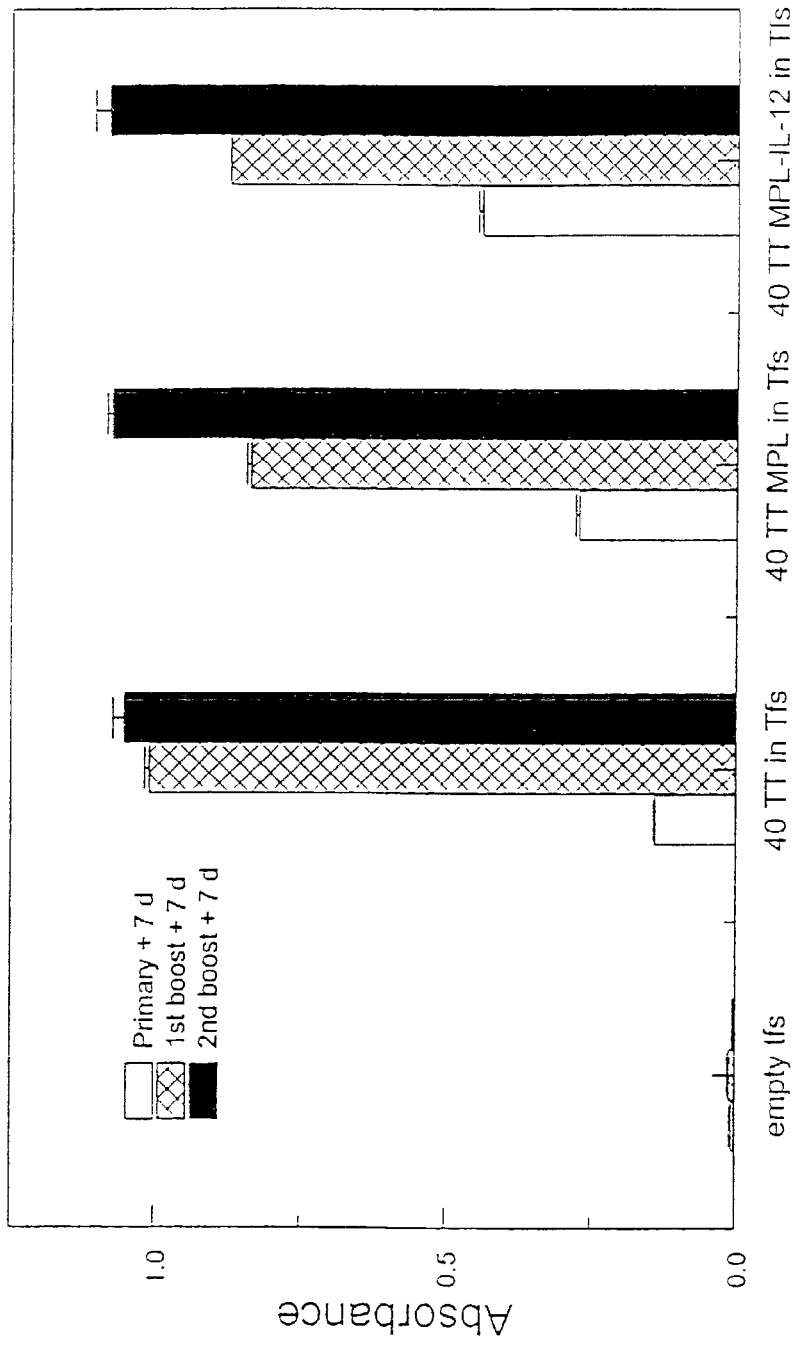

FIG. 12 deals with the effects of combining low and high molecular weight immuno-adjuvants (lipid a analogue and interleukin-12).

Figure 13:
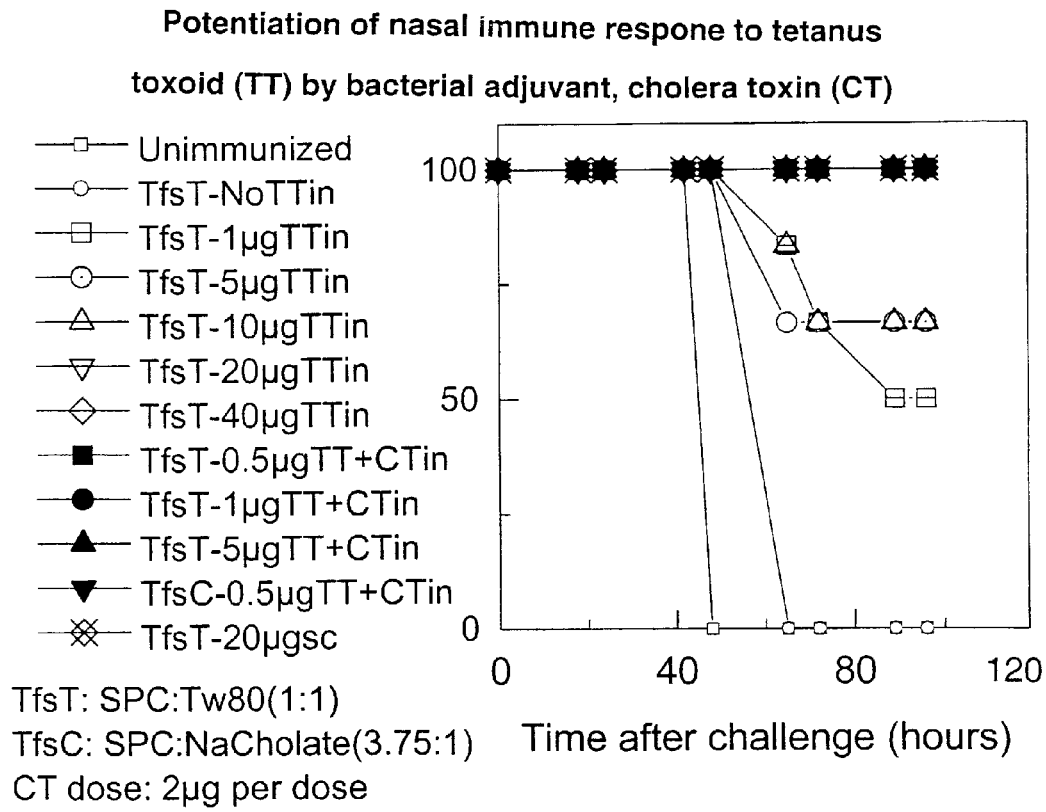
Figure 13:
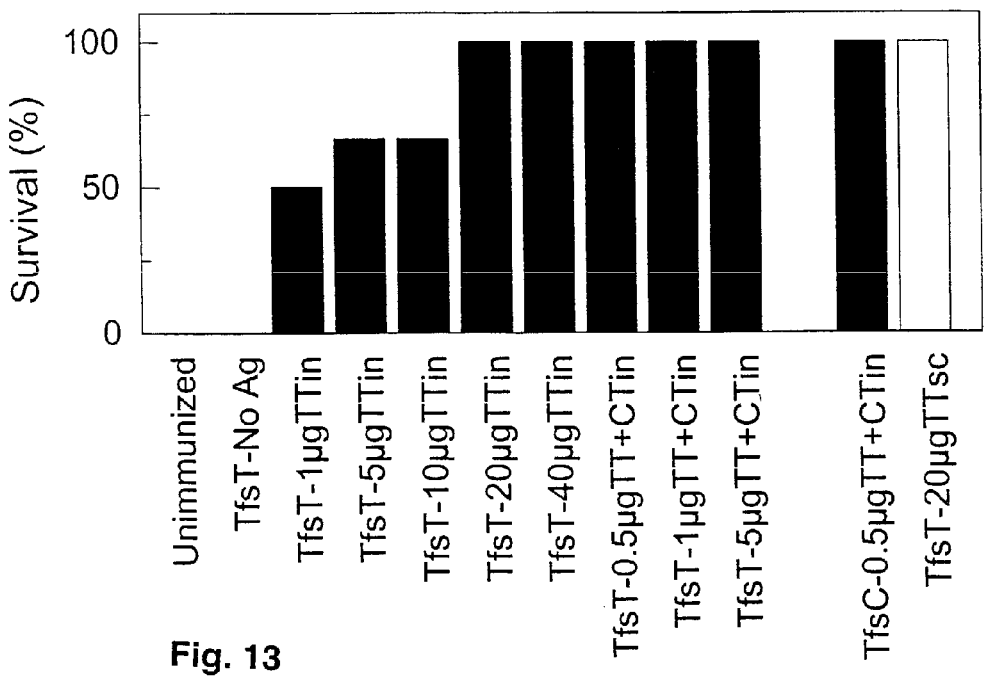

FIG. 13 illustrates the effect of specific cytokine inducers of microbial origin. Cholera toxin (CT) is used for the purpose.

Figure 14:
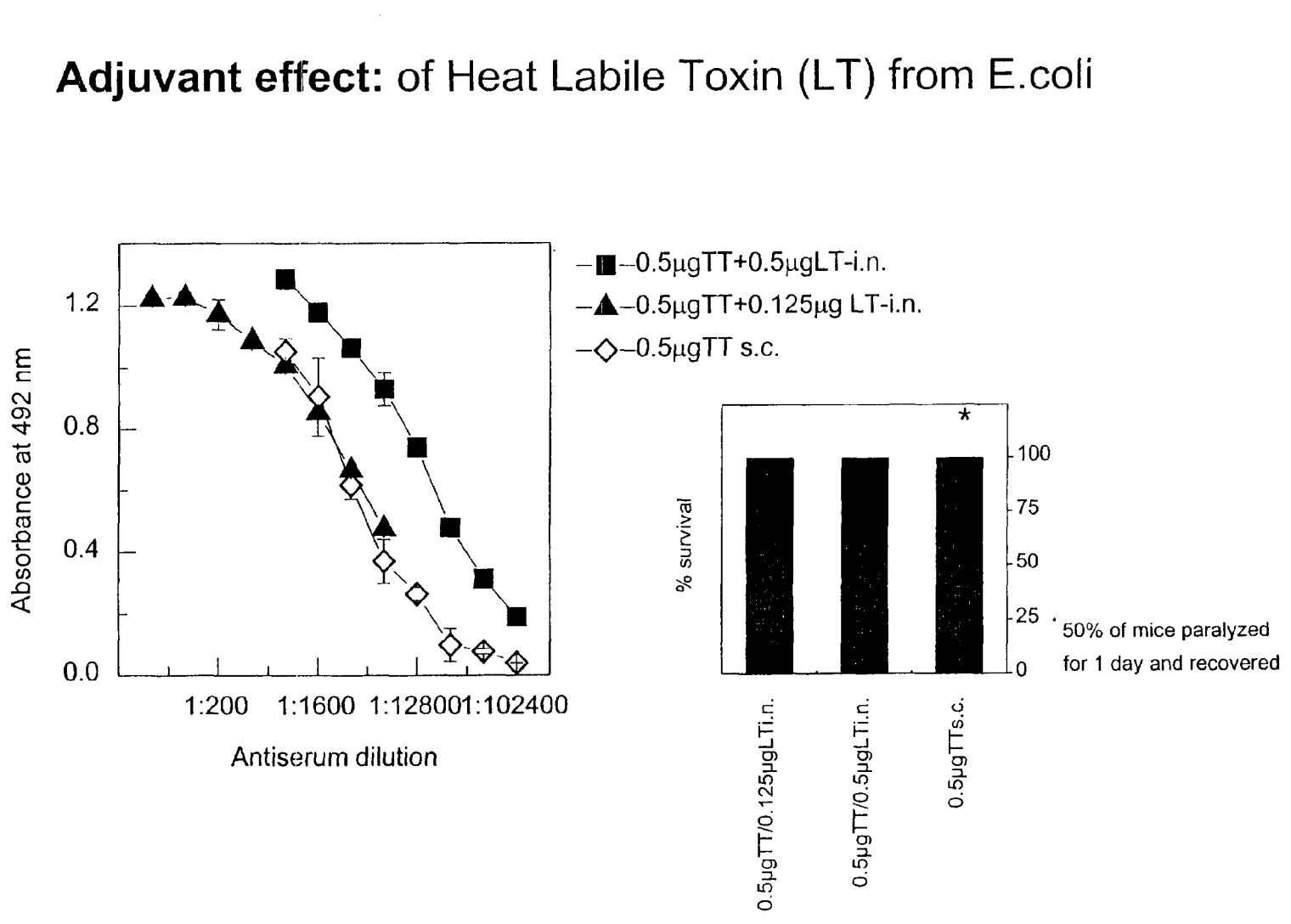

FIG. 14 shows one effect of heat labile toxin from *E. coli* as immuno-adjuvant.

FIG. 15 illustrates the results obtained with a combination of two antigens, tetanus toxoid and cholera toxoid.

The examples illustrate the invention.

EXAMPLES

General Experimental Set-Up and Sample Preparation

Conventional vesicles, liposomes, comprised soy phosphatidylcholine (SPC; Nattermann Phospholipids, Rhone-Poulenc Rorer, Cologne, Germany). The suspension containing 10 w-% of the lipid in form of multilamellar vesicles was prepared by suspending the lipid in a buffer and then extruding the suspension through several polycarbonate membranes (with 800 nm, 400 nm, 200 nm and 100 nm pores, respectively) to narrow down the final vesicle size distribution. If required, as judged on the basis of optical inspection or the dynamic light scattering done after the latter steps, extrusions were repeated several (up to 5) times. In some cases, the vesicles were first extruded to a diameter of app. 50 nm and then frozen and thawed three times to enlarge the vesicles again, owing to inter-vesicle fusion. Subsequently, the formulation was passed through a micro-porous filter (100 nm; Poretics, CA), under pressure, to prepare the final suspension of oligo- or unilamellar vesicles.

Highly adaptable penetrants, used in the described examples, typically had the form of ultradeformable vesicles (Transfersomes™) with one or a few bilayers. They comprised a mixture of phosphatidylcholine and (bio)surfactants (cholate or polysorbate (Tween 80)), and various biologically active ingredients, such as insulin, interferon, interleukin, or GC-SF.

The above mentioned penetrants were prepared by mixing the phospholipid(s) with a suitable membrane-softening agent, such as cholate or polysorbate, as the case may be, either in an aqueous buffer or in ethanol; occasionally chloroform was used. In the latter two cases, which gave similar results, the solvent was evaporated under vacuum (10 Pa, overnight). The resulting lipid film was then hydrated with a buffer (pH around 7) to get a 10 wt-% lipid suspension, by and large. Vesicles were brought to the final, desired size by sequential extrusion as described for liposomes, using mainly filters with smaller pore sizes. The final size of Transfersomes was similar to that of liposomes.

Changing the surfactant-to-lipid ratio is believed to affect the mixed lipid bilayers deformability: the higher the surfactant concentration, the more adaptable is the resulting aggregate, up to the concentration at which the mixed lipid membranes became unstable, owing to the high surfactant concentration. At such point the mixed aggregates revert into micelles which no longer change their shape easily, owing to the low compressibility of the micelle interior. Vesicles without a surfactant or some other edge active ingredient, which are commonly known as liposomes and have at least 10× less flexible membranes than the more deformable mixed lipid vesicles, are a convenient negative control for the latter. The other obvious control are Mixed lipid micelles containing similar ingredients as the corresponding highly adaptable penetrants, but in a different ratio, such that the edge active component (typically, but not necessarily, the surfactant) concentration is above the solubilization concentration value. To prepare said micelles, individual components were mixed in the aqueous phase and permitted them to interact until the mixture became optically clear, that is, solubilised, as judged by optical inspection or absorption measurement at 400 nm to 600 nm.

Experiments Carried Out on Human Volunteers

To test biological activity of insulin carriers in humans, a freshly prepared test formulation was used in the nose of two test subjects. The first was a normoglycaemic (male, 74 kg, 173 cm, 45 years); the second was a C-peptide negative IDDM patient (female, 62 kg, 167 cm, 26 years). The test persons fasted between 6 h and 12 h prior to insulin administration.

To follow the temporal variation of glucose concentration in the blood, 5 μL to 30 μL samples taken, every 10 min to 15 min, from the fingers on both arms. After an initial test period, during which the 'normal' blood glucose concentration and/or its change was determined, a suspension of carriers loaded with insulin (Transfersulin) was sprayed into each nostril, using conventional non-metered sprayer, in a series of 150 μL puffs. Care was taken to minimise the spill-over of test formulation into the throat or the dropping of said formulation from the nose.

Commercial glucometer (Accutrend™, Boehringer-Mannheim) was employed to determine the blood sugar concentration. At each time point, three individual, independent readings were made, except when the standard deviation was so high as to require repeated measurements.

The test formulations were made essentially as described in patent application PCT/EP98/06/50 published as WO 00/24377 and equivalent to U.S. Publication No. 2008/2798151). In brief, a suspension of highly adaptable penetrants with the above mentioned composition and an average diameter of the order of 100 nm to 150 nm was loaded with the drug, based on interfacial adsorption, and used within 24 h after the preparation. The drug-carrier association in the formulation was determined to be between 60% and 70%.

To administer the drug laden suspension into the nose, the preparation was filled into a commercial nebuliser (with a hand-driven pump, vertically oriented spraying nozzle and a puff volume of 150 μL, on the average). One puff was given into each nostril at a time, while the test subject gently sniffed.

The total number of puffs was a function of the application dose (in this case: 2). Immediate spill-over into the throat or partial leakage of the fluid from the nose was reported in 10-20% of cases. No side effects, such as local irritation, sneezing, etc., were observed.

Example 1

28.4 mg/mL phosphatidylcholine from soy-bean 9.5 mg/mL phosphatidylglycerol from soy-bean 62.1 mg/mL Tween 80 phosphate buffer, pH 7.4 human recombinant (hr) insulin, 50 IU/mL (from Actrapid 100 HM™, Novo-Nordisk)

Applied dose: ~5 IU per nostril

Figure 2:
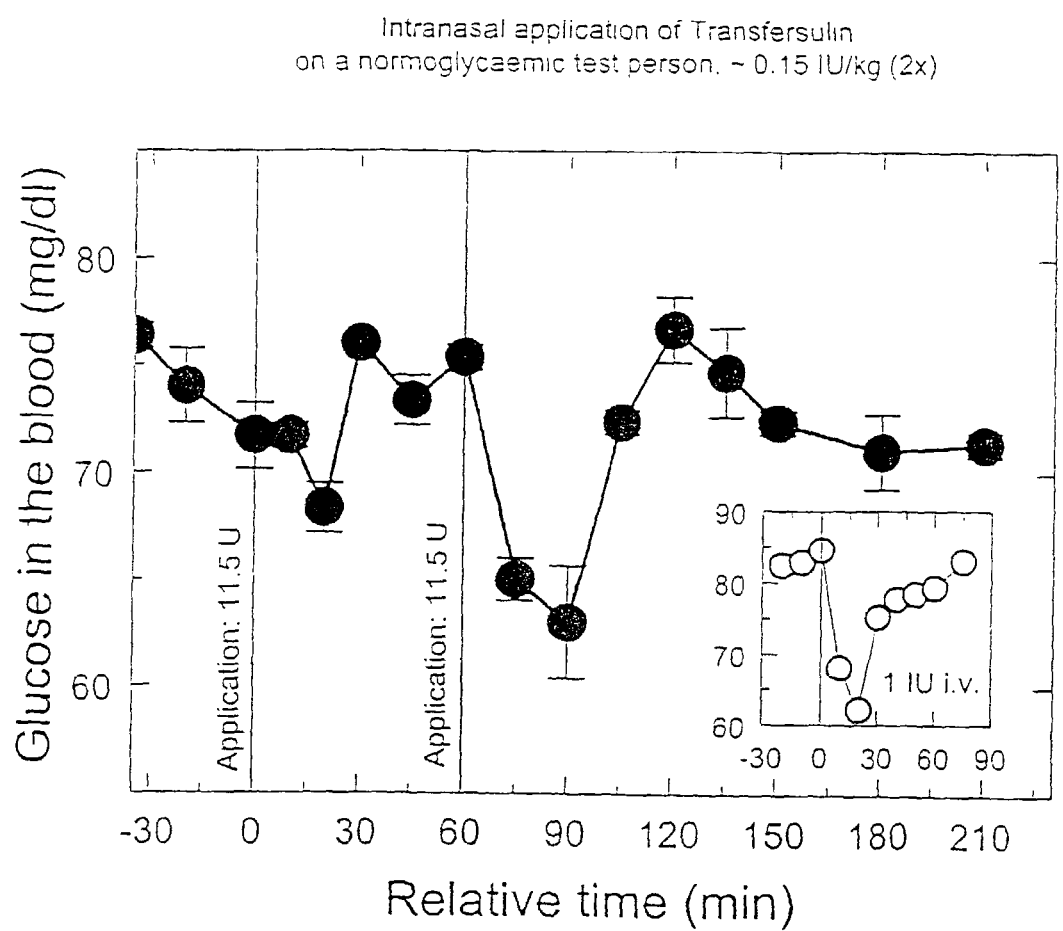
FIG. 2 illustrates the glucodynamics in a healthy human volunteer following intranasal administration of insulin by means of Transfersomes. Inset gives the result of intravenous injection of similar formulation for reference purpose.

Results measured with a healthy subject are shown in FIG. 2. They reveal a transient decrease in the systemic blood glucose concentration after two administrations of the drug in carriers (dosed symbols), with a maximum after 20-30 min and a return to the pre-treatment value after approximately 1 h in either case. The observed change in glucose level corresponds to approximately 8.5% of the decrease was measured in an independent experiment after intravenous injection of the drug (inset: open symbols). The reproducibility remains to be improved, however, the first application, biased by the lack in administration skill having been less successful than the second administration.

No irritation or other unpleasant sensation was reported by the test person after nasal administration of insulin in highly adaptable penetrants.

Example 2

Insulin Loaded, Highly Adaptable Carriers in an IDDM Patient highly adaptable penetrants:
as given in example 1
Applied dose: 25 IU per nostril Test preparation and experiment was performed as described with previous example. The last administration of conventional insulin (Monotard™, Novo-Nordisk), at the dose of 22 IU was done at 10 p.m. on the previous day. Test subject, moreover, was stabilised by using long-acting insulin on the test day prior to nasal administration of the insulin associated with highly adaptable drug carriers.

Figure 1:
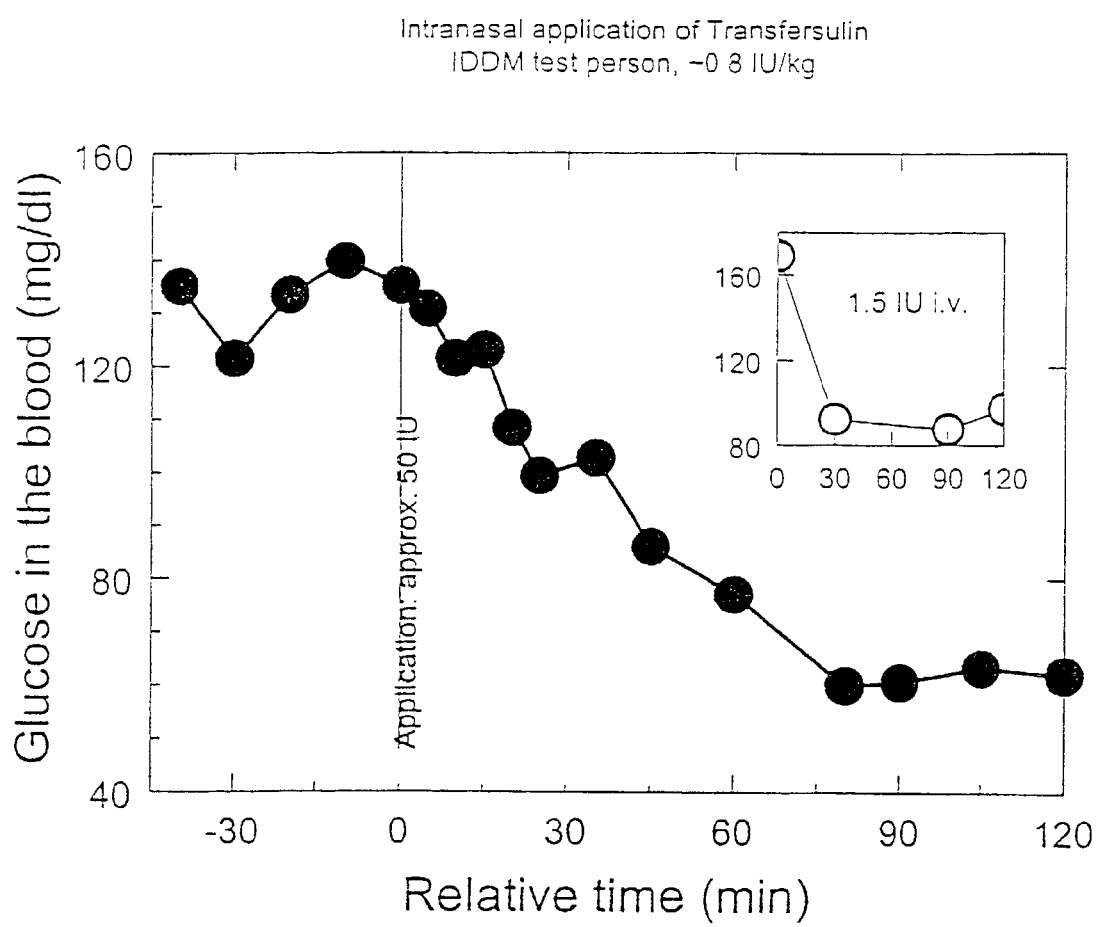
FIG. 1 illustrates the effect of nasal insulin administration by means of carriers in an insulin dependent diabetes mellitus patient, with the result of an i.v. injection of fast-acting insulin (Actrapid, Novo-Nordisk) shown in the inset for reference.

Results of an experiment done with said IDDM patient is illustrated in FIG. 1. Owing to the lack of endogenic insulin production in this test subject, the pre-treatment blood glucose concentration was slightly above the normal, but relatively constant. The change resulting from nasal drug administration with ultra-adaptable carriers, has more a step-like rather than a peak-like shape (closed symbols), completed within 75 min. This is precisely what one would expect for an IDDM patient. The result of an i.v. injection of rapidly acting insulin (Actrapid™, Novo-Nordisk) in the same test person on a different occasion (inset: open symbols) corroborates the conclusion. An estimate of apparent bioavailability of nasal insulin based on these data is around 4% and, consequently, somewhat lower than that reported in example 1. This may have to do with the presumed variability in drug release between different formulations which is illustrated in the following examples.

Nasal administration of carrier-associated insulin, according to the test person, caused no adverse side effect, locally or systemically.

Examples 3-5

Insulin Associated with Suboptimal Carriers

Carriers
as in previous examples, but believed not to release the drug readily owing to the higher affinity of selected insulin batch for the carrier, which makes the drug adsorption irreversible.
Applied doses: 50 IU, 50 IU Results of the test measurements done with several different vesicle suspensions, illustrated in FIGS. 3a and 3b, signal lack of action for the insulin administered nasally with such carriers. The blood glucose concentration in the investigated normoglycaemic test person remains the same before, during and after the drug administration, for several hours at least. This suggests that the mere presence of carriers, or their ingredients, is insufficient to improve the bioavailability of nasally applied macromolecules, such as insulin. To achieve the desired biological effect, the rate of drug release from the carrier must also be adequate, such rate being determined in dedicated ex vivo experiments by using conventional protein binding deassociation techniques.

Animal Experiments

Examples 6-9

Labelled Insulin Delivery Across Nasal Mucosa of Test Mice highly adaptable penetrants:
87.4 mg/mL phosphatidylcholine from soy bean (SPC)

12.6 mg/mL of a 50% ionised cholic acid
phosphate buffer, 50 mM, pH 6.5
hr-Insulin (Actrapid™, Novo-Nordisk) labelled insulin from Amersham
(345 µL contain 1.08 µg insulin and 1.725 mg BSA)

$^{125}$I-labelled insulin (210 µL) was mixed with 210 µL of hr-insulin (Actrapid™ Novo-Nordisk, 100 HM) and purified 2 times by centrifugation to eliminate the non-bound label, which diffuses across the barrier much faster and better than whole drug molecules. 100 µL of the resulting solution was mixed with 150 µL phosphate buffer to yield pH around 7. Protein solution and lipids were processed together, bringing the final vesicle size by repeated extrusion through 100 nm pore filters to values around 150 nm.

Mice of NMRI strain (36 g to 51 g) from a local supplier were kept in suspension cages in groups of 4 to 6. The animals had free access to standard chow and water. Each mouse received 2.5 µL of labelled penetrant suspension containing insulin per nostril. Then, the decrease in total radioactivity was assessed by whole-body camera at least 2 times. At different times the mice were killed and all major organs were taken and measured separately. The carcass was measured in two steps, after organ elimination and then after separation of the head. Radioactivity in excrement and cage was also determined.

Results pertaining to different time-points are given in FIG. 5. They show that substantial amount of nasally administered radioactivity is recovered from the body, even after exclusion of gastro-intestinal tract, especially during the first hours following suspension administration. Values in the blood are in the range of 9% at 0.5 h and 2%, the specific concentration falling from 3%/mL at the beginning to 0.7%/mL at the end. Activity in the nose decreases from 10.4% at 0.5 h to 0.3% at 8 h. Liver values are between 2.3% after 0.5 h, the maximum around 2.8 at 1 h and values above 1% after 4 h. After 8 h, the residuum in the liver is around 0.4%. The relatively high hepatic values are suggestive of passage of particles, that is, penetrants, through the barrier and subsequent uptake in the reticulo-endothelial system.

Corresponding CNS values are 0.1% and 0.03%. Maximum in the brain is measured between the first and second hour with app. 0.11% and 0.14%, respectively, which amounts to around 0.3%/g organ. These, apparently low values compare favourably with the result of more conventional drug delivery into CNS which yields values below 0.5% of injected dose or around 0.15%/g organ, for example, when transferrin-receptor is used to deliver the drug (Pasechnik & Price, 1996). In the case of white-germ agglutinin 0.1% was found in olfactory bulb.

Examples 10-11 highly adaptable penetrants
  87.4 mg/mL phosphatidylcholine from soy bean (SPC)
  12.6 mg/mL of a 50% ionised cholic acid
  phosphate buffer, 50 mM, pH 6.5
  human recombinant insulin (Actrapid™ Novo-Nordisk)
  labelled insulin from Amersham In a related experiment, 345 µL of $^{125}$I-labelled insulin was mixed with 345 µL of cold Actrapid™ (Novo-Nordisk) and purified 2 times, as in previous experiment. After addition of 200 µL phosphate buffer, 150 µL of resulting solution was mixed with the lipids and extruded to final vesicle size. The applied dose was 3 µL per nostril. Mice were killed after 1 h, fixed, cut in thin sections and inspected by the whole-body radiography. Free insulin in solution was used for comparison.

The results of above mentioned experiments (not shown) revealed high label accumulation in the nasal region, as one would expect, substantial spill-over into the GI tract, very high density in the bladder, but also some radioactivity in the liver, which appears to be slightly higher for the carrier-derived than for the free insulin.

Examples 12-13

Labelled Interferon-Gamma Delivery Across Nasal Mucosa of Test Mice highly adaptable penetrants
  86.6 mg/mL phosphatidylcholine from soy bean (SPC)
  13.4 mg/mL Na cholate
  phosphate buffer, 10 mM, pH 7.2 (nominal)
  1 mg IFN-gamma/mL suspension
  (100 µCi/mL suspension, as 3-$^{125}$I-tyrosyl-IFN-gamma)
Applied dose: 5 µL nostril Mice of NMRI strain (36±0.6 g) were housed and taken care of as described with previous examples. Prior to the test formulation application, the animals were sedated as described before. Test formulation then was administered through a fine catheter in two drops of 5 µL, resulting in the total dose of 1 mg lipid. After this, the animals were kept in separate cages to prevent mutual contamination.

Measured radioactivity in the blood was found to correspond to app. 2.5% of the applied dose, liver concentration being at app. 2% and colon concentration around 2.5%, all after 2 h. The highest amount of radioactivity by then was recovered from the stomach (37%) and in the cage plus excrement (32%). See FIG. 6.

In the central nervous system (CNS) 0.06% of total nasally applied dose, as judged by derived radioactivity, was present 1 h after the drug administration by means of highly adaptable, protein-loaded mixed lipid-surfactant vesicles.

Examples 14-19

Cytokine Delivery Across the Nasal Mucosa of Test Mice highly adaptable penetrants
  37.7 mg/mL phosphatidylcholine from soy bean (SPC)
  62.3 mg/mL polysorbate (Tween 80)
  phosphate buffer, 10 mM, pH 6.5
  Tetanus toxoid, as antigen (2 mg/mL)
  Interferon-γ (IFN-γ)
  Granulocyte-monocyte-colony stimulating factor (GM-CSF)
  Interleukin 4 (IL-4)
  Interleukin 12 (IL-12)
Applied dose: 3 µL per nostril Mice of Swiss albino strain (18-20 g) were obtained from The National Institute of Nutrition (Hyderabad, India). They were 8 to 12 weeks old at the time of first immunisation. The antigen alone or in combination with various cytokines, both believed to be at least partly associated with the carriers, was positioned with a sequencing in front of the animal nose and left to be sucked-in by the latter. Blood samples were collected retro-orbitally and tested with specific antibodies directed against the employed antigen by measuring absorbance at 492 nm, after subtraction of blank samples with ELISA.

The results of above mentioned measurements, illustrated in FIG. 4, suggest that the presence of all tested cytokines in vaccination formulation, based on the highly adaptable antigen carriers, increases the serum absorbance compared to that characterizing the non-modulated value, determined after simple immuno-carrier administration. Relative differences are more likely consequences of diverse bio-potency of tested immuno-modulants employed in the present specific experimental system than indicative of variable macromolecular transport rate across the nasal mucosa.

The observed 100% increase in serum absorbance measured for GM-CSF/IL-4 combination is remarkable, as it is known that neither polysorbate nor phosphatidylcholine ex soy-bean can markedly enhance permeation capability on their own. It is therefore reasonable to assume that the observed effect is not simply due to the delivery of antigen molecules (with the molar mass of 150 kDa) across the nasal mucosa but, moreover, testify that at least a proportion of co-administered cytokines has passed the barrier in a biologically active form.

Examples 20-21 highly adaptable penetrants
    as in examples 14-19, except for the absence of cytokines
    Tetanus toxoid antigen (2 mg/mL)
Mixed lipid micelles
    14.8 mg/mL phosphatidylcholine from soy bean (SPC)
    85.2 mg/mL polysorbate (Tween 80)
    phosphate buffer, 10 mM, pH 6.5
    Tetanus toxoid antigen (2 mg/mL)
Applied dose: 3 µL per nostril
    Experiments were done as described with previous examples (14-19).

Immune response in the animals treated with mixed lipid micelles as in Examples 14-19 was clearly inferior to that measured after the nasal application of antigen in the highly adaptable lipid vesicles, despite the fact that the latter contained a smaller amount of Tween 80 than the former. If the surfactant was responsible for the transport of macromolecules across nasal mucosa, owing to its action as skin permeation enhancer, precisely the opposite experimental outcome would have been expected.

This suggests that highly adaptable carriers (mixed lipid vesicles) transport macromolecules across the nasal mucosa by a mechanism other than the drug permeation.

Examples 22-29

Aggregate Size (Stability) Effect

Highly deformable vesicles with NaCh (Transfersomes™)
    89.3 mg phosphatidylcholine from soy bean
    10.7 mg sodium cholate (NaCh)
    0.9 mL phosphate buffer, pH 6.5
(Mixed lipid) Micelles with NaCh, type 1
    65 mg phosphatidylcholine from soy bean
    35 mg sodium cholate
    0.9 mL phosphate buffer, pH 6.5
(Mixed lipid) Micelles with NaCh, type 2
    31.6 mg phosphatidylcholine from soy bean
    68.5 mg sodium cholate
    0.9 mL phosphate buffer, pH 6.5
Highly deformable vesicles with Tw, Transfersomes™ type 1
    37.7 mg phosphatidylcholine from soy bean
    62.3 mg Tween 80 (Tw)
    0.9 mL phosphate buffer, pH 6.5
Highly deformable vesicles with Tw, Transfersomes™, type 2
    64.5 mg phosphatidylcholine from soy bean
    35.5 mg Tween 80
    0.9 mL phosphate buffer, pH 6.5
(Mixed lipid) Micelles with Tw, type 1
    13.2 mg phosphatidylcholine from soy bean
    86.8 mg Tween 80
    0.9 mL phosphate buffer, pH 6.5
(Mixed lipid) Micelles with Tw, type 2
    7 mg phosphatidylcholine from soy bean
    93 mg Tween 80
    0.9 mL phosphate buffer, pH 6.5
    0.10
Lipid vesicles (liposomes)
    65 mg phosphatidylcholine from soy bean (SPC)
    35 mg cholesterol
    0.9 mL phosphate buffer, pH 6.5
Tetanus toxoid (2 mg/mL; home made) used at the dose of
    40 µg (20 µL) TT per mouse and immunisation The medium filtrate from a culture of *Clostridium tetani* grown in vitro was used as an purified antigen. Pure toxoid was purchased from Accurate Antibodies, NY, USA.

To test the effect of aggregate properties in the formulation, three kind of aggregates were prepared: relatively large vesicles (diameter between 100 nm and 200 nm) either comprising a flexible membrane (Transfersomes) or a relatively rigid membrane (liposomes) and much smaller micelles (diameter below 50 nm). The latter were chosen to mimic the more conventional approach of using detergents as nasal mucosa permeation enhancers.

Amongst the eight tested formulations, Transfersomes, on the average, give best results, but absolute titres are always very low, probably owing to the antigen impurity. Mixed lipid micelles are most efficient in creating IgA, but are not really different than the other aggregates in the case of IgG2a and IgM, whilst in the case of Ig2b they are comparable to Transfersomes. The IgG1 level, which is decisive for animal protection, is only significantly elevated when Transfersomes are used to deliver TT across through the nose (see FIG. 7a).

Mixed micelles containing less potent detergents (with lesser skin permeation enhancing capability) are, relatively speaking, less efficient 'immuno-carriers' (see FIG. 7a, the more deformable Transfersomes with a higher Tw content standing clearly out in the case of IgG2a and IgM, are similar to the less deformable Transfersomes with a lower Tw content in the case IgG1 and IgG3, and are as efficient as mixed micelles with Tw in the case of IgA and IgG2b. The smallness of measured values is reason for the concern, however, which can best be overcome by using purer antigen.

Looking at the cumulative titre of all specific anti-TT antibodies in the serum, liposomes are relatively efficient 'immuno-carriers' in the primary and mature response (perhaps owing to the action of non-associated TT), whilst the Tw rich mixed micelles are the worst. NaCh Transfersomes are top performers in the late immune response (cf. FIG. 7c).

Examples 30-35

Antigen Dose and Purity Effect

Highly deformable vesicles (Transfersomes):
    86.3 mg phosphatidylcholine from soy bean (SPC)
    13.7 mg sodium cholate (NaChol)
    +/−0.04 mol-% monophosphoryl Lipid A (LA) relative to SPC
    0.9 mL phosphate buffer, 10 mM, pH 6.5
Tetanus toxoid (TT, from local source, purified by ultrafiltration)
    0 µg, 40 µg or 80 µg TT/mouse/immunisation To obtain partially purified antigen, such filtrate was passed through a 10 kDa cut-off membrane and washed thoroughly with phosphate buffer, pH 6.5; in the process, the culture filtrate was concentrated 15 times.

Dose dependence results are illustrated in FIG. 8a. The TT-specific increase in serum absorbance following TT administration through the nose by means of Transfersomes reveals a positive dose dependence in the primary and late immune response in the absence of LA, the presence of LA reverting this trend. Titre-wise and with regard to specific antibody isotype distribution, similar but not identical picture is obtained (cf. FIGS. 8b and 8c). The survival data are indicative of good protection in every case. Taken together this suggests that the required dose for non-invasive nasal immunisation by means of highly deformable carriers is much lower than that required for a successful non-invasive TT administration through the skin.

Antigen purity effect. Comparison of the data shown in FIGS. 8c and 7a and 7b shows that antigen purity strongly affects the level of murine immune response against tetanus toxin when the toxoid has been applied non-invasively through.

Examples 36-46

Route of Administration

Highly deformable vesicles, NaCh Transfersomes™
  as described with examples 1-8
Tetanus toxoid mixed with NaCh suspension
  20 mg/mL sodium cholate in
  phosphate buffer, pH 7
Tetanus toxoid dose: 40 µg TT per immunisation; 5 µg TT, 10 µg TT, 20 µg TT, 40 µg TT per immunisation.

Using the same experimental procedures as described with previous examples, the antibody-specific serum absorbance the corresponding antibody titre and isotype distribution, and the level of animal protection against tetanus toxin was determined after nasal, oral and subcutaneous antigen administration.

The results are given in FIGS. 9 *a-c*. They reveal that the increase in serum absorbance, ultimately, is comparable after invasive and non-invasive antigen administration (FIG. 9*a*). However, the titre in the former case is significantly lower after the first boost Interestingly, s.c. injection only produces superior results after the second boost, whereas the combination with TT and cholate, which then can act as nasal permeation enhancer in total antibody titre is better at all times. The probable reason for this is the high concentration of IgG2b, as is seen from FIG. 9*c*. Injections elicit most efficiently the IgG1 and IgM type of antibodies.

Animals are well protected by any of above mentioned vaccinations with TT, but only after 2 boosts; in the case of nasal vaccination. In contrast, one boost is sufficient (data not shown). Using 4-8× lower doses of purified TT suffices for protection in the case of nasal vaccination, but not when the antigen is injected (cf. FIG. 10*a*.

Example 47

Low Molecular Weight Adjuvant (Lipid A) Effect

Highly deformable immuno-modulated TT-Transfersomes™:
as in examples 9-14
Tetanus toxoid: 2 mg/mL, with 20 μL or 40 μL corresponding to 40 μg or 80 μg TT per immunisation It is believed that co-administration of immuno-active, typically immunopotentiating, molecules is advantageous for presentation TT associated with the carriers to the body. To substantiate this conclusion specifically the outcome of non-invasive immunopresentation of TT was compared by means of Transfersomes with or without monophosphoryl lipid A (LA), which is a well known immunostimulant known to elicit generation of TNF, for example. For the used, relatively high antigen doses no strong dependence was found, however. In either case substantial titres and a prophylactic immune response was reached, which was not the case with purified TT which profited from the presence of LA.

Examples 48-53

High Molecular Weight Immunomodulators (Cytokines)

Highly deformable vesicles, Tw Transfersomes™:
as described with examples 1-8, plus
various cytokines (Interferon-γ, GM-CSF, IL-4, IL-12)
(0.05 mg IFN-γ; 0.004 mg GM-CSF; 0.004 mg IL-4 per mL, 0.004 mg IL-12 per mL)
Tetanus toxoid, 2 mg/mL, corresponding to 40 μg TT (purified, home prepared) per mouse/immunisation The effect of cytokines was studied individually and in combination. The results are given in FIGS. 11*a* and 11*b*. They suggest that GM-CSF plus IL-4 combination can support the generation of anti-TT antibodies in mice, as can, probably, IFN-γ and perhaps IL-12, and maybe IL-4 (cf. FIG. 11*a*). The strongest effect is seen in the case of IgM and IgA, except in the case of IL-12 usage, which only affects strongly IgG2b generation. The protection relevant IgG1 is increased strongly only by the combination of GM-CSF and IL-4, whereas IgG3 is not affected at all. Intranasal administration works best for IgG1 (Cf. FIG. 11*b*).

Examples 54-58

Combination of Low and High Molecular Weight Adjuvants (LA+IL-12) Effect

Highly deformable vesicles, NaCh Transfersomes™,
as described with examples 1-8, plus
0.4 mg IL-12 per mL immunogen suspension
0.04 mol-% monophosphoryl Lipid A (LA) relative to SPC
Tetanus toxoid (purified), 2 mg/mL, corresponding to 40 μg TT per mouse/immunisation The effect discussed with examples 30-35 was confirmed for a blend low molecular and high molecular weight immunoadjuvants. The results are given in FIG. 12 and show that the immunopotentiation by such a combination is especially strong during the early stage of immune response, the combination in any case being better than LA alone.

Examples 59-71

Bacterial Wall Component, Cholera Toxin, as Adjuvant

Highly deformable vesicles, Transfersomes™ (Tfs):
TfsC
86.3 mg phosphatidylcholine from soy bean (SPC)
13.7 mg sodium cholate (NaChol)
0.9 mL phosphate buffer, 10 mM, pH 6.5
0.1 mL ethanol
TfsT 36 mg phosphatidylcholine from soy bean (SPC)
64 mg Tween 80
0.9 mL phosphate buffer, 10 mM, pH 7
Cholera toxin (CT; Sigma, Neu-Ulm), 2 μg/immunisation, if specified,
Tetanus toxoid (TT, pure; Accurate Antibodies), 2 mg/mL.

Volume doses corresponding to 0 μg TT/mouse/immunisation (negative control), 1 μg TT/mouse, 5 μg TT/mouse, 10 μg TT/mouse, 20 μg TT/mouse, 40 μg TT/mouse (in the absence of CT) and 0.5 μg TT/mouse/immunisation, 1 μg TT/mouse, 5 μg TT/mouse (when using CT) was used intranasally in the type T Transfersomes (TfsT) in both nostrils and at the dose of 0.5 μg TT/mouse/immunisation in the type C Transfersomes (TfsC) in 4-6 Swiss albino mice. Moreover, 20 μg TT/mouse/immunisation in TfsT was injected subcutaneously at the corresponding site in the positive control group. Immunisations were done on days 1, 14, 28.

The protective effect of antigen applied in the nose was good when the antigen dose exceeded 20 μg/immunisation; lower doses yielded insufficient, but detectable protection (cf. FIG. 13). When cholera toxin (CT) was included into the test formulation together with the tetanus toxoid, excellent protection was achieved already at the lowest of tested doses (0.5 μg/immunisation), independent of the ultra-deformable carrier composition. Protection was complete in all test groups containing CT in the formulation applied subcutaneously.

Examples 72-74

Heat Labile Toxin from *E. Coli* (HLT) as Immuno-Adjuvant

Highly deformable vesicles, Transfersomes™:
TfsC
86.3 mg phosphatidylcholine from soy bean (SPC)
13.7 mg sodium cholate (NaChol)
0.9 mL phosphate buffer, 10 mM, pH 6.5
Heat Labile Toxin (HLT, SIGMA, Neu-Ulm), 1 mg/mL plus, if required
Tetanus Toxoid (TT, pure, Accurate Antibodies) 2 mg/mL
or
TfsT
36 mg phosphatidylcholine from soy bean (SPC)
64 mg Tween 80
0.9 mL phosphate buffer, 10 mM, pH7
Heat Labile Toxin (LT, SIGMA, Neu-Ulm), 1 mg/mL, if required,
Tetanus Toxoid (TT, pure, Accurate Antibodies) 2 mg/mL Antigen carriers were prepared and all experiments (with Swiss albino mice) and assays were carried out as described in the previous examples. A series of different HLT doses ranging from approx. 50 ng/application to multi-microgram quantity per application was used in combination with TT concentrations in the range of approx. 100 ng and up to 10 μg per application. In most cases, volume doses corresponding to 0.5 μg TT/mouse/i.n. immunisation and 0.1 to 0.5 μg HLT/mouse/i.n. immunisation and a positive control with 0.5 μg TT for s.c. injection was used for mice immunisation.

As is shown in FIG. 14, anti-TT titres are improved by HLT acting as an adjuvant in comparison with the result of s.c. injection without an adjuvant. The humoral response is dose dependent, i.e. higher anti-TT titres are achieved with the higher dose of HLT. The correlation is not linear, however, but shows rather a maximum (data not shown).

Protection against tetanus toxin challenge is equally efficient for the high and the low dose of immuno adjuvant.

This suggests that adjuvants should be used in the nose in conjunction with Transfersomes at maximum at the dose that is in the low-end range of doses used for conventional invasive (s.c.) immunisations; the minimum dose for immuno-Transfersomes usage in the nose should also be 1-2 orders lower, for the adjuvant tested in this series for most, if not all, immunoadjuvants.

Example 75

Bivalent vaccination with Tetanus Toxoid and Cholera Toxin as antigens

Highly deformable vesicles, Transfersomes™:
86.3 mg phosphatidylcholine from soy bean (SPC)
13.7 mg sodium cholate (NaChol)
0.9 mL phosphate buffer, 10 mM, pH 6.5
Cholera Toxin (CT, SIGMA, Neu-Ulm), ≦1 mg/mL
Tetanus Toxoid (TT, pure, accurate antibodies) 2 mg/mL
or
TfsT
36 mg phosphatidylcholine from soy bean (SPC)
64 mg Tween 80
0.9 mL phosphate buffer, 10 mM, pH7
Cholera Toxin (CT, SIGMA, Neu-Ulm), ≦1 mg/mL
Tetanus Toxoid (TT, pure, accurate antibodies) 2 mg/mL Details on the formulation and its preparation, on vesicle characterisation and on animal experiments as well as the following assays are given in the description of related examples hereinabove.

The main result of this experimental series was that Cholera Toxin, added to the formulation as an adjuvant, can also induce the formation of anti-CT antibodies in practically relevant quantity. This effect can, but does not have to, be achieved using concentrations of CT and TT sufficient to ensure good protection against the challenge with tetanus toxin. FIG. 15 compares anti-TT and anti-CT titres from the same mice immunised with TT and CT within the same carrier. This reveals the potential of Transfersomes™ containing more than one antigen to serve as the basis for at least bivalent vaccines.

LITERATURE

Bagnasco-M; Mariani-G; Passalacqua-G; Motta-C; Bartolomei-M; Falagiani-P; Mistrello-G; Canonica-G W Absorption and distribution kinetics of the major *Parietaria judaica* allergen (Par j 1) administered by noninjectable routes in healthy human beings. J-Allergy-Clin-Immunol. 1997; 100: 122-9

Biberoglu-K; Gursoy-R; Yildiz-A Treatment of estrogen-dependent gynecological disorders with the gonadotropin releasing hormone agonist buserelin. Gynecol-Endocrinol. 1991; 5: 109-22

Bruins-J; Hijman-R; Van-Ree-J M Effect of acute and chronic treatment with desglycinamide-[Arg8]vasopressin in young male and female volunteers. Peptides. 1995; 16: 179-86

Cevc-G Drug delivery across the skin. Exp. Opin. Invest. Drugs (1997) 6: 1887-1937

Cevc-G; Gebauer-D; Schatzlein-A; Blume-G Ultraflexible vesicles, Transfersomes, have an extremely low permeation resistance and transport therapeutic amounts of insulin across the intact mammalian skin. Biochim. Biophys. Acta 1998; 1368: 201-215

Draghia-R; Caillaud-C; Manicom-R; Pavirani-A; Kahn-A; Poenaru-L Gene delivery into the central nervous system by nasal instillation in rats. Gene-Ther. 1995; 2: 418-23

Drejer-K, Baag-A, Bech-K, Hansen-P, Sorensen-A R, Mygind-N. Diab. Med. 1992, 9: 335-340.

Flanagan-B; Pringle-C R; Leppard-K N A recombinant human adenovirus expressing the simian immunodeficiency virus Gag antigen can induce long-lived immune responses in mice. J-Gen-Virol. 1997; 78: 991-7

Gizurarson-S; Bechgaard-E Intranasal administration of insulin to humans. Diabetes-Res-Clin-Pract. 1991 May; 12: 71-84

Ghigo-E; Arvat-E; Gianotti-L; Grottoli-S; Rizzi-G; Ceda-G P; Boghen-M F; Deghenghi-R; Camanni-F Short-term administration of intranasal or oral Hexarelin, a synthetic hexapeptide, does not desensitize the growth hormone responsiveness in human aging. Eur-J-Endocrinol. 1996; 135: 407-12

Harris-A S Review: clinical opportunities provided by the nasal administration of peptides. J-Drug-Target. 1993; 1: 101-16

Huneycutt-B S; Plakhov-I V; Shusterman-Z; Bartido-S M; Huang-A; Reiss-C S; Aoki-C Distribution of vesicular stomatitis virus proteins in the brains of BALB/c mice following intranasal inoculation: an immunohistochemical analysis. Brain-Res. 1994; 635: 81-95

Hussain-A; Hamadi-S; Kagashima-M; Iseki-K; Dittert-L Does increasing the lipophilicity of peptides enhance their nasal absorption? J-Pharm-Sci. 1991; 80: 1180-1

Ichikawa-M; Nakamuta-H; HoshinO-T; Ogawa-Y; Koida-M Anti-osteopenic effect of nasal salmon calcitonin in type 1 osteoporotic rats: comparison with subcutaneous dosing. Biol-Pharm-Bull. 1994; 17: 911-3

Illum-L The nasal delivery of peptides and proteins. Trends-Biotechnol. 1991; 9: 284-9

Illum-L; Davis-S S Intranasal insulin. Clinical pharmacokinetics. Clin-Pharmacokinet. 1992 July; 23: 30-41

Invitti-C; Fatti-L; Carnboni-M G; Porcu-L; Danesi-L; Delitala-G; Effect of chronic treatment with octreotide nasal powder on serum levels of growth hormone, insulin-like growth factor I, insulin-like growth factor binding proteins 1 and 3 in acromegalic patients. Cavagnini-F J-Endocrinol-lnvest. 1996; 19: 548-55

Kida-S; Pantazis-A; Weller-R O. SF drains directly from the subarachnoid space into nasal lymphatics in the rat. Anatomy, histology and immunological significance. Neuropathol. Appl. Neurobiol. 1993; 19: 480-448

Laursen-T; Grandjean-B; Jorgensen-J O; Christiansen-J S Bioavailability and bioactivity of three different doses of nasal growth hormone (GH) administered to GH-deficient patients: comparison with intravenous and subcutaneous administration. Eur-J-Endocrinol. 1996; 135: 309-15

Machida-M; Sano-K; Arakawa-M; Hayashi-M; Awazu-S Absorption of recombinant human granulocyte-colony-stimulating factor (rhG-CSF) from rat nasal mucosa. Pharm-Res. 1993; 10: 1372-7.

Maejima-K; Tamura-K; Taniguchi-Y; Nagase-S; Tanaka-H Comparison of the effects of various fine particles on IgE antibody production in mice inhaling Japanese cedar pollen allergens. J-Toxicol-Environ-Health. 1997; 52: 231-48

Maitani-Y; Machida-Y, Nagai-T Influence of molecular weight and charge on nasal absorption of dextran and DEAE-dextran in rabbits. Int. J. Pharmaceut. 1989; 49: 23-27

McMartin-C; Hutchinson-L E F; Hyde-R; Peterrs-G E. Analysis of structural requirements for the absorption of drugs and macromolecules from the nasal cavity. J. Pharm. Sci. 1987; 76: 535-540

Mori-I; Nakakuki-K; Kimura-Y Temperature-sensitive parainfluenza type 1 vaccine virus directly accesses the central nervous system by infecting olfactory neurons. J-Gen-Virol. 1996; 77: 2121-4

Naumann-E; Bartussek-D; Kaiser-W; Fehm-Wolfsdorf-G Vasopressin and cognitive processes: two event-related potential studies. Peptides. 1991; 12: 1379-84

Pasechnik-V; Price-J Macromolecular drug delivery to the CNS with protein carriers. Exp. Opin. Invest. Drugs 1996, 5: 1255-1276

Paul-A; Cevc-G Non-invasive Administration of Protein Antigens: Transdermal Immunization with Bovine Serum Albumine in Transfersomes. Vaccine Res. 1995; 4: 145-164

Paul, A., Cevc, G. Non-invasive administration of protein antigens. Epicutaneous immunisation with the bovine serum albumin. Vaccine Res. (1995) 4: 145-164.

Perras-B; Molle-M; Born-J; Fehm-H L Sleep and signs of attention during 3 months of intranasal vasopressin: a pilot study in two elderly subjects. Peptides. 1996; 17: 1253-5

Pietrowsky-R; Struben-C; Molle-M; Fehm-H L; Born-J Brain potential changes after intranasal vs. intravenous administration of vasopressin: evidence for a direct nose-brain pathway for peptide effects in humans. Biol-Psychiatry. 1996; 39: 332-40

Pihoker-C; Middleton-R; Reynolds-G A; Bowers-C Y; Badger-T M Diagnostic studies with intravenous and intranasal growth hormone-releasing peptide-2 in children of short stature. J-Clin-Endocrinol-Metab. 1995; 80: 2987-92

Pohl-J; Arnold-H; Schulz-A; Pause-B M; Schulte-H M; Fehm-Wolfsdorf-G Modulation of pain perception in man by a vasopressin analogue. Peptides. 1996; 17: 641-7

Sarkar-M A Drug metabolism in the nasal mucosa. Pharm-Res. 1992; 9: 1-9

Shimoda-N; Maitani-Y; Machida-Y; Nagai-T Effects of dose, pH and osmolarity on intranasal absorption of recombinant human erythropoietin in rats. Biol-Pharm-Bull. 1995; 18: 734-9

Sperber-S J; Doyle-W J; McBride-T P; Sorrentino-J V; Riker-D K; Hayden-F G Otologic effects of interferon beta serine in experimental rhinovirus colds. Arch-Otolaryngol-Head-Neck-Surg. 1992; 118: 933-6

Ting-TY; Gonda-I; Gipps-E M Microparticles of polyvinyl alcohol for nasal delivery. I. Generation by spray-drying and spray-desolvation. Pharm-Res. 1992; 9: 1330-5

Tsume-Y; Taki-Y; Sakane-T; Nadai-T; Sezaki-H; Watabe-K; Kohno-T; Yamashita-S Quantitative evaluation of the gastrointestinal absorption of protein into the blood and lymph circulation. Biol-Pharm-Bull. 1996; 19: 1332-1337

Watanabe-Y; Matsumoto-Y; Yamaguchi-M; Kikuchi-R; Takayama-K; Nomura-H; Maruyama-K; Matsumoto-M Absorption of recombinant human granulocyte colony-stimulating factor (rhG-CSF) and blood leukocyte dynamics following intranasal administration in rabbits. Biol-Pharm-Bull. 1993; 16: 93-5.

Watanabe-Y; Matsumoto-Y; Kikuchi-R; Kiriyama-M; Nakagawa-K; Nomura-H; Maruyama-K; Matsumoto-M Pharmacokinetics and pharmacodynamics of recombinant human granulocyte colony-stimulating factor (rhG-CSF) following intranasal administration in rabbits. J-Drug-Target. 1995; 3: 231-8

Wearley-L L Recent progress in protein and peptide delivery by noninvasive routes. Crit-Rev-Ther-Drug-Carrier-Syst. 1991; 8: 331-94

Westenberg-H G; Hijman-R; Wiegant-V M; Laczi-F; Van-Ree-J M Pharmacokinetics of DGAVP in plasma following intranasal and oral administration to healthy subjects. Peptides. 1994; 15: 1101-4 van-der-Wiel-H E; Lips-P; Nauta-J; Kwakkel-G; Hazenberg-G; Netelenbos-J C; van-der-Vijgh-W J Intranasal calcitonin suppresses increased bone resorption during short-term immobilization: a double-blind study of the effects of intranasal calcitonin on biochemical parameters of bone turnover. J-Bone-Miner-Res. 1993; 8: 1459-65

The invention claimed is:

1. A method for administering a pharmaceutical composition to a patient in need thereof, comprising:
   transnasally administering to the patient a pharmaceutical composition, the pharmaceutical composition comprising:
      an active ingredient; and
      a carrier comprising a penetrant suspended or dispersed in a solvent,
         the penetrant comprising a minute fluid droplet surrounded by a coating of at least one layer of at least two substances, the substances differing by at least a factor of 10 in solubility in an aqueous medium,
         the substances forming homoaggregates of one substance and/or heteroaggregates of the at least two substances, the average diameter of homoaggregates of the more soluble substance or the average diameter of the heteroaggregates of the at least two substances being smaller than the average diameter of homoaggregates of the less soluble substance, and/or
         the more soluble substance solubilizing the droplet and the content of the more soluble substance is up to 99 mol-% of the concentration required to solubilize the droplet or corresponds to up to 99 mol-% of the saturating concentration in an unsolubilized droplet, whichever is higher, and/or
         wherein the elastic deformation energy of the droplet surrounded by the coating is at least five times lower than the deformation energy of red blood cells or of a phospholipid bilayer having fluid aliphatic chains, and wherein the less soluble substance is a lipid and the more soluble substance is a surfactant or more soluble form of the lipid.

2. The method of claim 1, wherein the at least two substances are two forms of a substance.

3. The method of claim 1, wherein the active ingredient is an allergen.

4. The method of claim 1, wherein the active ingredient is an antigen.

5. The method of claim 1, further comprising a compound that is a cytokine or a compound that induces cytokine or anti-cytokine activity.

6. The method of claim 5 wherein the cytokine is IL-4 (interleukin-4), IL-3 (interleukin-3), IL-2 (interleukin-2), TGF (transforming growth factor), IL-6 (interleukin-6), TNF (tumour necrosis factor), IL-1α (interleukin-1α), IL-1β (interleukin-1β), a type I interferon, IFN-alpha (interferon-alpha), IFN-β (interferon-β), IL-12 (interleukin-12), IFN-gamma (interferon-gamma), TNF-β (tumour necrosis factor-β), IL-5 (interleukin-5) or IL-10 (interleukin-10).

7. The method of claim 5 wherein the compound with anti-cytokine activity is an anti-cytokine antibody or active fragment thereof.

8. The method of claim 5 wherein the compound that is a cytokine or induces cytokine or anti-cytokine activity and the active ingredient are associated with the penetrant.

9. The method of claim 1, wherein the less soluble substance is a lipid, and the more soluble substance is a surfactant.

10. The method of claim 1, wherein the less soluble substance is a lipid, and the more soluble substance is a more soluble form of the lipid.

11. The method of claim 1, wherein the more soluble substance solubilizes the penetrating droplet and is present in concentration not exceeding 99 mol % of the concentration required to disintegrate the droplet or not exceeding 99 mol % of the saturating concentration in the unsolubilized droplet, whichever is higher.

12. The method of claim 1, wherein the less soluble substance is a polar lipid and the more soluble substance is a surfactant.

13. The method of claim 1, wherein the less soluble substance is a polar lipid and the more soluble substance is a polar lipid.

14. The method of claim 1, wherein the average diameter of the penetrant is between 25 nm and 500 nm.

15. The method of claim 1, wherein the average diameter of the penetrant is between 30 nm and 250 nm.

16. The method of claim 1, wherein the average diameter of the penetrant is between 35 nm and 200 nm.

17. The method of claim 1, wherein the average diameter of the penetrant is between 40 nm and 150 nm.

18. The method of claim 1, wherein the concentration of penetrant is 0.001 to 20 weight-% of total dry mass in the pharmaceutical composition.

19. The method of claim 1, wherein the concentration of penetrant is between 0.01 w-% and 15 w-% of total dry mass in the pharmaceutical composition.

20. The method of claim 1, wherein the concentration of penetrant is between 0.1 w-% and 12.5 w-% of total dry mass in the pharmaceutical composition.

21. The method of claim 1, wherein the concentration of penetrant is between 0.5 w-% and 10 w-% of total dry mass in the pharmaceutical composition.

22. The method of claim 1, wherein the solvent is a supporting medium.

23. The method of claim 22, wherein the supporting medium is a biocompatible solution having an osmotic activity of a monovalent electrolyte with concentration in the range between 1 mM and 500 mM.

24. The method of claim 22, wherein the supporting medium is a biocompatible solution having an osmotic activity of a monovalent electrolyte with concentration in the range between 10 mM and 400 mM.

25. The method of claim 22, wherein the supporting medium is a biocompatible solution having an osmotic activity of a monovalent electrolyte with concentration in the range between 50 mM and 300 mM.

26. The method of claim 22, wherein the supporting medium is a biocompatible solution having an osmotic activity of a monovalent electrolyte with concentration in the range between 100 mM and 200 mM.

27. The method of claim 22, wherein the supporting medium is a biocompatible solution.

28. The method of claim 22, wherein the supporting medium is a biocompatible buffer with pH of between 4 and 10.

29. The method of claim 1, wherein the active ingredient concentration is between 0.001 and 40 weight-% of total penetrant mass.

30. The method of claim 1, wherein the active ingredient concentration is between 0.01 w-% and 30 w-% of total penetrant mass.

31. The method of claim 1, wherein the active ingredient concentration is between 0.1 w-% and 25 w-% of total penetrant mass.

32. The method of claim 1, wherein the active ingredient concentration is between 0.5 w-% and 15 w-% of total penetrant mass.

33. The method of claim 1, wherein the applied penetrant dose is between 0.01 mg and 15 mg per nostril.

34. The method of claim 1, wherein the pharmaceutical composition is administered using a metered delivery device.

35. The method of claim 1, wherein the penetrants are in suspension and further comprising loading the penetrants with the active ingredient within 24 hours prior to transnasal administration.

36. The method of claim 1, wherein a target site of the active ingredient is a nervous system.

37. The method of claim 36 wherein the target site is a brain.

38. The method of claim 1, wherein the pharmaceutical composition is a vaccine.

39. The method of claim 38, wherein the vaccine further comprises an adjuvant.

40. The method of claim 39, wherein the adjuvant is lipopolysaccharide, or an extract of a microorganism.

41. The method of claim 38, wherein the vaccine comprises MPL (monophosphoryl lipid A) and IL-12 (interleukin-12) or GM-CSF (granulocyte macrophage colony stimulating factor) and IL-4 (interleukin-4).

42. The method of claim 38, wherein at least two doses of vaccine are administered.

43. The method of claim 38, wherein the vaccine is administered as a booster vaccination.

44. The method of claim 42, wherein the time interval between subsequent vaccinations is between 2 weeks and 5 years.

45. A method for administering a pharmaceutical composition to a patient in need thereof, comprising:

transnasally administering to the patient a pharmaceutical composition, wherein the pharmaceutical composition is for the treatment of infective diseases, endocrine disorders, adrenal disorders, gastrointestinal disorders, hemorrhagic diseases, musculoskeletal and connective tissue disorders, neurological disorders, ontological disorders, psychiatric disorders, and/or for use in the field of gynecology, and/or for use in the field of immunology, the pharmaceutical composition comprising:

an active ingredient; and a carrier comprising a penetrant suspended or dispersed in a solvent, the penetrant comprising a minute fluid droplet surrounded by a coating of at least one layer of at least two substances, the substances differing by at least a factor of 10 in solubility in an aqueous medium, the substances forming homoaggregates of one substance and/or heteroaggregates of the at least two substances, the average diameter of homoaggregates of the more soluble substance or the average diameter of the heteroaggregates of the at least two substances being smaller than the average diameter of homoaggregates of the less soluble substance, and/or the more soluble substance solubilizing the droplet and the content of the more soluble substance is up to 99 mol-% of the concentration required to solubilize the droplet or corresponds to up to 99 mol-% of the saturating concentration in an unsolubilized droplet, whichever is higher, and/or wherein the elastic deformation energy of the droplet surrounded by the coating is at least five times lower than the deformation energy of red blood cells or of a phospholipid bilayer having fluid aliphatic chains, and wherein the less soluble substance is a lipid and the more soluble substance is a surfactant or more soluble form of the lipid.

46. The method of claim 45, wherein the active ingredient is an antigen.

47. The method of claim 45, wherein the active ingredient is an allergen.

48. The method of claim 1, wherein the active ingredient is a polypeptide or a protein.

49. The method of claim 1, wherein the active ingredient comprises at least one of the group consisting of insulin, IFN-gamma (interferon-gamma), Tetanus toxoid, GM-CSF (granulocyte macrophage colony stimulating factor), IL-4 (interleukin-4), IL-12 (interleukin-12), monophosphoryl lipid A, Cholera toxin, and Heat Labile toxin.

50. The method of claim 1, wherein the active ingredient is an immunologically active substance.

51. The method of claim 1, wherein the less soluble substance comprises a phospholipid.

52. The method of claim 51, wherein the phospholipid has the chemical formula:

where $R_1$ and $R_2$ is a $C_{10-20}$-acyl or -alkyl or a partly unsaturated fatty acid residue, and where $R_3$ is hydrogen, 2-trimethylamino-1-ethyl, 2-amino-1-ethyl, $C_{1-4}$-alkyl, $C_{1-5}$-alkyl substituted with carboxy, $C_{2-5}$-alkyl substituted with hydroxy, $C_{2-5}$-alkyl substituted with carboxy and hydroxy, or $C_{2-5}$-alkyl substituted with carboxy and amino, inositol, sphingosine, or salts of said substances.

53. The method of claim 52, wherein the unsaturated fatty acid residue is an oleoyl-, palmitoeloyl-, elaidoyl-, linoleyl-, linolenyl-, linolenoyl-, arachidoyl-, vaccinyl-, lauroyl-, myristoyl-, palmitoyl-, or stearoyl chain.

54. The method of claim 51, wherein the lipid is at least one of the group consisting of phosphatidylcholine, phosphatidylethanolamine, phosphatidylglycerol, phosphatidylinositol, phosphatidic acid, phosphatidylserine, and sphingophospholipid.

55. The method of claim 1, wherein the lipid comprises soybean phosphatidylcholine.

56. The method of claim 1, wherein the less soluble substance is soybean phosphatidylcholine; the more soluble substance is Tween-80, sodium cholate or cholic acid; and the active ingredient is a peptide or protein.

* * * * *